(12) United States Patent
Yuan et al.

(10) Patent No.: US 9,586,880 B2
(45) Date of Patent: Mar. 7, 2017

(54) SMALL MOLECULE INHIBITORS OF NECROPTOSIS

(71) Applicant: President and Fellows of Harvard College, Cambridge, MA (US)

(72) Inventors: Junying Yuan, Newton, MA (US); Emily P. Hsu, Munich (DE)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/033,176

(22) Filed: Sep. 20, 2013

(65) Prior Publication Data

US 2014/0024657 A1 Jan. 23, 2014

Related U.S. Application Data

(63) Continuation of application No. 13/141,545, filed as application No. PCT/US2009/069483 on Dec. 23, 2009, now abandoned.

(60) Provisional application No. 61/140,615, filed on Dec. 23, 2008.

(51) Int. Cl.

| C07D 233/02 | (2006.01) |
|---|---|
| C07C 35/37 | (2006.01) |
| C07D 209/08 | (2006.01) |
| C07D 211/90 | (2006.01) |
| C07D 215/08 | (2006.01) |
| C07D 231/06 | (2006.01) |
| C07D 231/12 | (2006.01) |
| C07D 231/56 | (2006.01) |
| C07D 277/46 | (2006.01) |
| C07D 307/52 | (2006.01) |
| C07D 333/20 | (2006.01) |
| C07D 403/06 | (2006.01) |
| C07D 403/12 | (2006.01) |
| C07D 405/06 | (2006.01) |
| C07D 417/12 | (2006.01) |
| C07D 495/04 | (2006.01) |
| C07D 498/08 | (2006.01) |
| C07C 33/38 | (2006.01) |
| C07D 211/78 | (2006.01) |
| C07D 277/18 | (2006.01) |

(52) U.S. Cl.
CPC .............. *C07C 35/37* (2013.01); *C07C 33/38* (2013.01); *C07D 209/08* (2013.01); *C07D 211/78* (2013.01); *C07D 211/90* (2013.01); *C07D 215/08* (2013.01); *C07D 231/06* (2013.01); *C07D 231/12* (2013.01); *C07D 231/56* (2013.01); *C07D 233/02* (2013.01); *C07D 277/18* (2013.01); *C07D 277/46* (2013.01); *C07D 307/52* (2013.01); *C07D 333/20* (2013.01); *C07D 403/06* (2013.01); *C07D 403/12* (2013.01); *C07D 405/06* (2013.01); *C07D 417/12* (2013.01); *C07D 495/04* (2013.01); *C07D 498/08* (2013.01)

(58) Field of Classification Search
CPC .................................................... C07D 233/02
See application file for complete search history.

(56) References Cited

U.S. PATENT DOCUMENTS

| 3,577,420 A | 5/1971 | Hess et al. |
|---|---|---|
| 3,932,430 A | 1/1976 | Habeck et al. |
| 4,016,037 A | 4/1977 | Mitsugi et al. |
| 4,110,536 A * | 8/1978 | Havera et al. ................ 544/139 |
| 4,177,054 A | 12/1979 | Arndt et al. |
| 4,332,952 A | 6/1982 | Schnur |
| 4,618,609 A | 10/1986 | Alker et al. |
| 4,837,165 A | 6/1989 | Hawke |
| 5,108,914 A | 4/1992 | Wagner et al. |

(Continued)

FOREIGN PATENT DOCUMENTS

| CN | 1897928 A | 1/2007 |
|---|---|---|
| CN | 101265254 A | 9/2008 |

(Continued)

OTHER PUBLICATIONS

Compound Summary for CID 3928273, access May 30, 2015 and created Sep. 12, 2005.*

(Continued)

*Primary Examiner* — Rebecca Anderson
*Assistant Examiner* — Karen Cheng
(74) *Attorney, Agent, or Firm* — Choate, Hall & Stewart LLP; Brenda H. Jarrell; Nishat A. Shaikh

(57) ABSTRACT

Compounds having the following structure (VI-A):

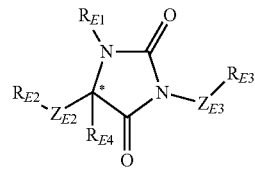

or any pharmaceutically acceptable salt or solvate thereof, or any stereoisomer thereof, wherein $R_{E1}$, $R_{E2}$, $R_{E3}$, $R_{E4}$, $Z_{E2}$ and $Z_{E3}$ are as disclosed herein, are provided. Pharmaceutical compositions comprising the compounds, and methods for use of the compounds for treating disorders associated with necrosptosis are also provided.

30 Claims, No Drawings

(56) References Cited

U.S. PATENT DOCUMENTS

| | | |
|---|---|---|
| 5,334,606 A | 8/1994 | MacLeod |
| 5,593,697 A | 1/1997 | Barr et al. |
| 5,693,643 A | 12/1997 | Gilbert et al. |
| 6,194,444 B1 | 2/2001 | Tsubata et al. |
| 6,300,349 B1 | 10/2001 | Margolin |
| 6,355,664 B1 | 3/2002 | Kelly et al. |
| 6,521,649 B1 | 2/2003 | Kuroda et al. |
| 6,541,630 B1 | 4/2003 | Atherall et al. |
| 6,756,394 B1 | 6/2004 | Yuan et al. |
| 6,797,708 B2 | 9/2004 | McKew et al. |
| 6,846,839 B1 | 1/2005 | Tang et al. |
| 6,887,993 B1 | 5/2005 | Tian et al. |
| 7,253,201 B2 | 8/2007 | Yuan et al. |
| 7,491,743 B2 | 2/2009 | Cuny et al. |
| 8,143,300 B2 | 3/2012 | Cuny et al. |
| 8,278,344 B2 | 10/2012 | Cuny et al. |
| 8,324,262 B2 | 12/2012 | Yuan et al. |
| 8,658,689 B2 | 2/2014 | Cuny et al. |
| 8,741,942 B2 | 6/2014 | Cuny et al. |
| 9,108,955 B2 | 8/2015 | Cuny et al. |
| 2002/0013350 A1 | 1/2002 | Nishiguchi et al. |
| 2002/0155172 A1 | 10/2002 | Yuan et al. |
| 2003/0083386 A1 | 5/2003 | Yuan et al. |
| 2003/0191134 A1 | 10/2003 | Shapiro et al. |
| 2004/0259904 A1 | 12/2004 | Tong et al. |
| 2005/0038053 A1 | 2/2005 | Hirvelae et al. |
| 2005/0119260 A1 | 6/2005 | Cuny et al. |
| 2005/0131044 A1 | 6/2005 | Yuan et al. |
| 2005/0288282 A1 | 12/2005 | Delorme et al. |
| 2006/0019952 A1 | 1/2006 | Distefano et al. |
| 2006/0198893 A1 | 9/2006 | Lindfors |
| 2007/0037752 A1 | 2/2007 | Ansorge et al. |
| 2007/0099936 A1 | 5/2007 | Bian et al. |
| 2007/0197551 A1 | 8/2007 | Sato et al. |
| 2008/0045541 A1 | 2/2008 | Gielen-Haertwig et al. |
| 2008/0234270 A1 | 9/2008 | Canne Bannen et al. |
| 2009/0099186 A1 | 4/2009 | Beigelman et al. |
| 2009/0099242 A1 | 4/2009 | Cuny et al. |
| 2009/0163545 A1 | 6/2009 | Goldfarb |
| 2010/0087453 A1 | 4/2010 | Yuan et al. |
| 2010/0190836 A1 | 7/2010 | Yuan et al. |
| 2010/0317701 A1 | 12/2010 | Cuny et al. |
| 2011/0144169 A1 | 6/2011 | Cuny et al. |
| 2012/0122889 A1 | 5/2012 | Yuan et al. |
| 2012/0149702 A1 | 6/2012 | Cuny et al. |
| 2012/0309795 A1 | 12/2012 | Cuny et al. |
| 2013/0158024 A1 | 6/2013 | Yuan et al. |
| 2014/0024657 A1 | 1/2014 | Yuan et al. |
| 2014/0024662 A1 | 1/2014 | Yuan et al. |
| 2014/0128437 A1 | 5/2014 | Cuny et al. |
| 2014/0323489 A1 | 10/2014 | Yuan et al. |
| 2016/0024098 A1 | 1/2016 | Yuan et al. |
| 2016/0102053 A1 | 4/2016 | Cuny et al. |
| 2016/0168128 A1 | 6/2016 | Yuan et al. |

FOREIGN PATENT DOCUMENTS

| | | |
|---|---|---|
| CN | 101304976 A | 11/2008 |
| EP | 0343643 B1 | 11/1989 |
| EP | 0545478 A1 | 6/1993 |
| EP | 1275646 A1 | 1/2003 |
| EP | 1447401 A1 | 8/2004 |
| GB | 2080803 A | 2/1982 |
| GB | 2128184 A | 4/1984 |
| JP | 49-66678 A | 6/1974 |
| JP | 55023994 A | 2/1980 |
| JP | 61022081 A | 1/1986 |
| JP | 2019363 A | 1/1990 |
| JP | 5004910 A | 1/1993 |
| JP | H05-262725 A | 10/1993 |
| JP | 2002-330785 A | 11/2002 |
| JP | 2003-198785 A | 7/2003 |
| JP | 2006-527226 A | 11/2006 |
| JP | 2007-508349 A | 4/2007 |
| JP | 2007-529422 A | 10/2007 |
| JP | 2008-517061 A | 5/2008 |
| WO | WO-90/04183 A1 | 4/1990 |
| WO | WO-92/04045 A1 | 3/1992 |
| WO | WO-96/30393 A1 | 10/1996 |
| WO | WO-98/02162 A1 | 1/1998 |
| WO | WO-98/39303 A1 | 9/1998 |
| WO | WO-01/28493 A2 | 4/2001 |
| WO | WO-01/85718 A1 | 11/2001 |
| WO | WO-02/02568 | 1/2002 |
| WO | WO-02/02568 A1 | 1/2002 |
| WO | WO-0244157 A2 | 6/2002 |
| WO | WO-03/037898 A1 | 5/2003 |
| WO | WO-2004/070050 A2 | 8/2004 |
| WO | WO-2004/093871 A1 | 11/2004 |
| WO | WO-2005/028664 A2 | 3/2005 |
| WO | WO-2005/032527 A2 | 4/2005 |
| WO | WO 2005/037257 A2 | 4/2005 |
| WO | WO-2005/072412 A2 | 8/2005 |
| WO | WO-2005/077344 A2 | 8/2005 |
| WO | WO-2006/044826 A2 | 4/2006 |
| WO | WO-2006/086358 A2 | 8/2006 |
| WO | WO-2007/047146 A2 | 4/2007 |
| WO | WO-2007/047604 A2 | 4/2007 |
| WO | WO-2007/059905 A2 | 5/2007 |
| WO | WO-2007/075772 A2 | 7/2007 |
| WO | WO-2007/087906 A1 | 8/2007 |
| WO | WO-2008/006883 A2 | 1/2008 |
| WO | WO-2008/045406 A2 | 4/2008 |
| WO | WO-2008/063667 A1 | 5/2008 |
| WO | WO-2008/147962 A1 | 12/2008 |
| WO | WO-2009/023272 A1 | 2/2009 |
| WO | WO-2009/086303 A2 | 7/2009 |
| WO | WO-2009/109983 A1 | 9/2009 |
| WO | WO-2010/075290 A1 | 7/2010 |
| WO | WO-2010/075561 A1 | 7/2010 |
| WO | WO-2014/152182 A1 | 9/2014 |
| WO | WO-2016/094846 A1 | 6/2016 |

OTHER PUBLICATIONS

Caplus DN 111:232814, published Feb. 26, 1991.*
Bralia et al., "Reaction of L-tryptophan with alkyl isocyanates." Heterocycles. 26(1):95-100 (1987).
Ooms et al., "Exploration of the pharmacophore of 3-alkyl-5-arylimidazolidinediones as new CB1 cannabinoid receptor ligands and potential antagonists: synthesis, lipophilicity, affinity and molecular modeling." J Med Chem. 45(9):1748-56 (2002).
Toniolo, "Optical rotatory properties of methylisothiocyanate-amino acid adducts." Tetrahedron. 26:5479-88 (1970).
Communication for Australian Patent Application No. 2004315596, dated Oct. 27, 2011 (3 pages).
Extended European Search Report for European Application No. 10011481.8, dated Oct. 4, 2011 (8 pages).
Partial European Search Report for European Application No. 10011481.8-, dated Jun. 7, 2011 (6 pages).
Argast et al., "Inhibition of RIP2/RICK/CARDIAK activity by pyridinyl imidazole inhibitors of p38 MAPK." Mol Cell Biochem. 268(1-2):129-40 (2005).
Boeijen, "Combinatorial chemistry of hydantoins." Bioorganic & Medical Chem Lett. 8(17):2375-80 (1998).
Borner et al., "Apoptosis without caspases: an inefficient molecular guillotine?" Cell Death Differ. 6(6):497-507 (1999).
Burk et al., "A convenient asymmetric synthesis of alpha-1-arylalkylamines through the enantioselective hydrogenation of enamides." J Am Chem Soc. 118:5142-3 (1996).
Buyukbingol et al., "Studies on the synthesis and structure-activity relationships of 5-(3'-indolal)-2-thiohydantoin derivatives as aldose reductase enzyme inhibitors." Farmaco. 49(6):443-7 (1994).
CAS RN: 160448-59-9 (2 pages), 1996.
CAS RN: 21753-16-2, 58667-71-3, 56612-92-1, 62943-91-0 (2 pages), 1978.
CAS RN: 317384-05-7, 317384-06-8, 325153-33-1 (2 pages), 2000.
Chem. Abstr. 52: 2956a-f, Ichihara,K., "The acid diazo reaction and 5- or 7-hydroxyindole derivatives: oxidation of the benzene moiety

(56) References Cited

OTHER PUBLICATIONS of indolelactic acid, indolepropionic acid, and indolylethylamine, etc., by liver extract," J Biochem. 44:649-59 (1957).
Chi et al., "Oncogenic ras triggers cell suicide through the activation of a caspase- independent cell death program in human cancer cells." Oncogene. 18(13):2281-90 (1999).
Cryns et al., "Proteases to die for." Genes Dev. 12(11):1551-70 (1998).
Degterev et al., "Chemical inhibitor of nonapoptotic cell death with therapeutic potential for ischemic brain injury," Nat Chem Biol. 1(2):112-9 (2005).
Edman, "Method for determination of the amino acid sequence in peptides." Acta Chem Scand. 4:283-93 (1950).
Eldadah et al., "Caspase pathways, neuronal apoptosis, and CNS injury," J Neurotrauma. 17(10):811-29 (2000).
El-Rayyes et al.,"Heterocycles. part VIII. synthesis of new substituted benz[g]indazoles," J Heterocyclic Chem. 23:135-40 (1986).
Fiers et al., "More than one way to die: apoptosis, necrosis and reactive oxygen damage." Oncogene. 18(54):7719-30 (1999).
Fujiwara et. al., "$^{13}$C nuclear magnetic resonance studies on the conformation of substituted hydantoins." J Chem Soc Perkin Trans 2. 1573-7 (1980).
Gulati et al., "A new synthesis of 5-bromoaplysinopsin, 6-bromoaplysinopsin and 3'-demethylaplysinopsin and their biological activities." Indian J Chem. 33B(1):10-6 (1994).
Hera et al., "Inhibition of interleukin 1beta converting enzyme family proteases reduces ischemic and excitotoxic neuronal damage." Proc Natl Acad Sci U.S.A. 94(5):2007-12 (1997).
Herceg et al., "Failure of poly(ADP-ribose) polymerase cleavage by caspases leads to induction of necrosis and enhanced apoptosis." Mol Cell Biol. 19(7):5124-33 (1999).
Hirsch et al., "The apoptosis-necrosis paradox. apoptogenic proteases activated after mitochondrial permeability transition determine the mode of cell death." Oncogene. 15(13):157-381 (1997).
Holler et al., "Fas triggers an alternative, caspase-8-indepdendent cell death pathway using the kinase RIP as effector molecule." Nature Immunol. 1(6):489-95 (2000).
Horwell et al., "Conformationally constrained amino-acids: synthesis of novel β, β-, 2,3-, and 3,4-cyclised tryptophans." Tetrahedron Lett. 39(47):8729-32 (1998).
Inglis et al., "The identification of tryptophan residues in proteins as oxidised derivatives during amino acid sequence determinations." FEBS Letters. 104(1):115-8 (1979).
Jagtap et al., "Structure-activity relationship study of tricyclic necroptosis inhibitors." J Med Chem. 50(8):1886-95 (2007).
Janin et al., "Methyl orthocarboxylates as methylating agents of heterocycles." Eur J Org Chem. 1763-9 (2002).
Kaul et al., "Pathways to neuronal injury and apoptosis in HIV-associated dementia." Nature. 410(6831):988-94 (2001).
Kawahara et al., "Caspase-independent cell killing by fas-associated protein with death domain." J Cell Biol. 143(5)1353-60 (1998).
Khodair, "A convenient synthesis, of glycosylated hydantoins as potential antiviral agents." Phosphorus Sulfur Silicon Relat Elem. 122:9-26 (1997).
Khwaja et al., "Resistance to the cytotoxic effects of tumor necrosis factor alpha can be overcome by inhibition of a FADD/Caspase-dependent signaling pathway." J Biol Chem. 274(51):36817-23 (1999).
Kitanaka et al., "Caspase-independent programmed cell death with necrotic morphology." Cell Death Differ. 6(6):508-15 (1999).
Kazlauskas et. al., "Aplysinopsin, a new tryptophan derivative from a sponge." Tetrahedron Lett. 1:61-4 (1977).
Leist et al., "Inhibition of mitochondrial ATP generation by nitric oxide switches apoptosis to necrosis." Exp Cell Res. 249(2):396-403 (1999).
Lewis et al., "Tryptophan-derived NK1 antagonists: conformationally constrained heterocyclic bioisosteres of the ester linkage." J Med Chem. 38:923-33 (1995).
Li et al., "Induction of necrotic-like cell death by tumor necrosis factor alpha and caspase inhibitors: novel mechanism for killing virus-infected cells." J Virol. 74(16):7470-7 (2000).
Luschen et al., "Sensitization to death receptor cytotoxicity by inhibition of fas-associated death domain protein (FADD)/caspase signaling. requirement of cell cycle progression." J Biol Chem. 275(32):24670-8 (2000).
Chem. Abstr., Abstract No. 46: 961c-g, Marchant, R.H., "Synthesis of 5- and 7-methoxytryptophan and of some derivatives." J Chem Soc. 1808-11 (1951).
Martin et al., "Neurodegeneration in excitotoxicity, global cerebral ischemia, and target deprivation: A perspective on the contributions of apoptosis and necrosis." Brain Res Bull. 46(4):281-309 (1998).
Matsumura et al., "Necrotic death pathway in fas receptor signaling." J Cell Biol. 151(6):1247-55 (2000).
McCarthy et al., "Inhibition of ced-3/ICE-related proteases does not prevent cell death induced by oncogenes, DNA damage, or the Bcl-2 homologue bak." J Cell Biol. 136(1):215-27 (1997).
McMurray, "Huntington's disease: new hope for therapeutics." Trends Neurosci. 24(11 Suppl):S32-8 (2001).
Molina et al., "A simple and general entry to aplysinopsine-type alkaloids by tandem aza-wittig/heterocumulene-mediated annelation." Tet Lett. 33(31):4491-4 (1992).
Nicotera et al., "Apoptosis and necrosis: different execution of the same death." Biochem Soc Symp. 66:69-73 (1999).
Nowak, "Application of allylisothiocyanate in synthesis of 3-allyl-2-thiohydantoins from amino acids and in the degradation of proteins," Roczniki Chemii. 47(12):2377-8 (1973).
Nowak, "Allyl Isothiocyanate in the synthesis of 3-allyl-2-thiohydantoins from amino acids and in the degradation of proteins." Roczniki Chemii. 47(12):2377-8 (1973) (Abstract only).
Park et al., "Diastereoselective synthesis of hydantoin- and isoxazoline-substituted dispirocyclobutanoids." J Org Chem. 65(11):3520-4 (2000).
Polniaszek et al., "Stereoselective nucleophilic additions to the carbon-nitrogen double bond. 3. chiral acyliminium ions." J Org Chem. 55(1):215-23 (1990).
Polverino et al., "Selective activation of caspases during apoptotic induction in HL-60 cells." J Biol Chem. 272(11):7013-21 (1997).
Raghupathi et al., "Apoptosis after traumatic brain injury," J Neurotrauma. 17(10):927-38 (2000).
Rahman et al., "Synthesis and biological studies of thiohydantoins." Bangladesh J Bio Sci. 5(1):28-30 (1976).
Sané et al., "Caspase inhibition in camptothecin-treated U-937 cells is coupled with a shift from apoptosis to transient G1 arrest followed by necrotic cell death." Cancer Res. 59(15):3565-9 (1999).
Selkoe, "Translating cell biology into therapeutic advances in alzheimer's disease." Nature. 399(6738 Suppl):A23-A31 (1999).
Selic et al., "A simple stereoselective synthesis of aplysinopsin analogs." Hely Chim Acta. 83(10):2802-11 (2000).
Suzuki et al., "Proton nuclear magnetic resonance studies on methylthiohydantoins, thiohydantoins, and hydantoins of amino acids." Can J Biochem. 55(5):521-7 (1977).
Chem. Abstr., Abstract No. 47: 9273c-I, Swan, J.M., "Thiohydantoins. I. Preparation of some 2-thiohydantoins from amino acids and acylamino acids." Australian Journal of Scientific Research, Series A: Physical Sciences p. A5:711-20 (1952).
Syntichaki et al., "Death by necrosis. Uncontrollable catastrophe, or is there order behind the chaos?" EMBO Rep. 3(7):604-9 (2002).
Szöllösy et al., "Fused heterocycles. Park 4. Synthesis and stereochemistry of hexahydrobenzo[6,7]Cyclohepta[1,2-c]Pyrazoles." J Chem Soc Perkin Trans. 2:489-93 (1991).
Takahashi et al., "Antimutagenic properties of 3, 5-disubstituted 2-thiohydantoins." J Agric Food Chem, 46:5037-42 (1998).
Talanian of al., "Caspases as targets for anti-inflammatory and anti-apoptotic drug discovery," Med Chem. 43(18):3351-71 (2000).
Teng et al.,"Structure-activity relationship study of novel necroptosis inhibitors," Bioorg Med Chem Lett. 15(22):5039-44 (2005).
Vercammen et al., "Dual signaling of the fas receptor: initiation of both apoptotic and necrotic cell death pathways." J Exp Med. 188(5):919-30(1998).

(56) References Cited

OTHER PUBLICATIONS

Vercammen et al., "Inhibition of caspases increases the sensitivity of L929 cells to necrosis mediated by tumor necrosis factor." J Exp Med. 187(9):1477-85 (1998).
Vila et al., "Engineered modeling and the secrets of Parkinson's disease," Trends Neurosci. 24(11 Suppl):S49-55 (2001).
Waterfield et al., "Amino acid sequence analysis with methyl isothiocyanate. Resolution of the methylthiohydantoins by gas-liquid partition chromatography." Biochemistry. 9(4):832-9 (1970).
Woo, "Gas chromatographic determination of methylthiohydantoin amino acid as N(O)-Butyldimethylsilyl derivatives in amino acid sequencing with methylisothiocyanate." J Korean Agric Chem Soc. 35(2):132-8 (1992).
Wyllie et al., "Cell death: the significance of apoptosis." Int Rev Cytol. 68:251-306 (1980).
Yuan et al., "Apoptosis in the nervous system." Nature. 407(6805):802-9 (2000).
Examiner's Report for Australian Patent Application No. 2004315596, dated Feb. 17, 2010, including CAS Registry Nos. 21753-16-2 (Nov. 16, 1984), 61159-99-7 (Nov. 16, 1984), 109063-48-1 (Jun. 11, 1987), 159308-51-7 (Dec. 2, 1994), 160448-59-9 (Jan. 27, 1995), and 428442-42-6 (Jun. 11, 2002) (4 pages).
European Patent Office Communication for European Application No. 04821344.1, dated Mar. 3, 2008 (4 pages).
European Patent Office Communication for European Application No. 04821344.1, dated May 10, 2010 (5 pages).
Notice of Reasons for Rejection for Japanese Patent Application No. 2006-524953, mailed Nov. 25, 2010 (7 pages).
International Search Report for International Application No. PCT/US2006/048583, dated Dec. 8, 2008 (4 pages).
International Preliminary Report on Patentability for International Application No. PCT/US2006/048583, date of mailing Jan. 13, 2009 (7 pages).
Written Opinion of the International Search Authority for International Application No. PCT/US2006/048583, mailed Dec. 8, 2008 (13 pages).
International Search Report for International Application No. PCT/US2009/069483, mailed May 5, 2010 (4 pages).
Office Action pertaining to U.S. Appl. No. 09/688,015, mailed May 30, 2001 (7 pages).
Office Action pertaining to U.S. Appl. No. 09/688,015, mailed Mar. 7, 2002 (5 pages).
Office Action pertaining to U.S. Appl. No. 09/688,015, mailed Nov. 5, 2002 (6 pages).
Office Action pertaining to U.S. Appl. No. 10/880,377, mailed Mar. 17, 2006 (10 pages).
Office Action pertaining to U.S. Appl. No. 10/880,377, mailed Jul. 20, 2006 (8 pages).
Office Action pertaining to U.S. Appl. No. 10/930,690, mailed Mar. 29, 2007 (12 pages).
Office Action in Australian Patent Application No. 2012201058, dated Sep. 20, 2012 (5 pages).
English Translation of Office Action for Japanese Patent Application No. 2011-116383, mailed Feb. 26, 2013 (6 pages).
Office Action for U.S. Appl. No. 12/077,320, dated May 2, 2011 (10 pages).
Office Action for U.S. Appl. No. 13/401,561, dated Apr. 15, 2013 (8 pages).
International Search Report for International Patent Application No. PCT/US2000/28475, dated Apr. 5, 2001 (4 pages).
International Search Report for International Patent Application No. PCT/US2004/028270, dated Jan. 18, 2006 (7 pages).
International Preliminary Report on Patentability for International Patent Application No. PCT/US2004/028270, dated Feb. 28, 2006 (8 pages).
Official Action for Japanese Application No. 2014-230271, dated Nov. 24, 2015 (7 pages).
Extended European Search Report for European Application No. 15001699.6, mailed Feb. 5, 2016 (16 pages).

Maki et al., "Fluorescence polarization assay for inhibitors of the kinase domain of receptor interacting protein 1," Anal Biochem. 427(2):164-74 (2012).
U.S. Appl. No. 13/589,867.
Bhatia, Apoptosis versus necrosis in acute pancreatitis, Am. J. Physiol. Gastrointest. Liver Physiol. 286:G189-G196 (2004).
Bisson et al., Binding properties of the C-terminal domain of VIAF, Chem Biol Drug Des. 72(5):331-336, 2008.
Bryn et al, 1999, SSCI, Inc., 2nd Edition, Ch. 10 Polymorphs, p. 232-247.
CAS Nos. 385385-70-6, 433702-79-5, 433702-79-5, 306281-11-8, 440340-55-6, 889957-34-0, and 877969-45-4, cited as Document 025 in the search report received in connection with European Patent Application No. 09835866.6, dated Mar. 15, 2013.
Christofferson et al, 2010, Current Opinion in Cell Biology, vol. 22, p. 263-268.
English Translation of the First Office Action for Chinese Patent Application No. 200980156914.4, dated Feb. 26, 2013.
Extended European Search Report from European Application No. 09835866.6, dated Jul. 18, 2012.
Faden, Neuroprotection and traumatic brain injury: theoretical option or realistic proposition, Curr. Opin. Neurol. 15:707-712 (2002).
Ferrell et al. In Pathology of the Liver, 4fh Edition; MacSween, R. N. M.; Burt, A. D.; Portmann, B. C.; Ishak, K. G.; Scheuer, P. J.; Anthony, P. P.; Eds.; Churchill Livingstone: London, 2002; p. 314. Exhibit I.
Gennarelli et al. In Textbook of Traumatic Brain Injury; Silver, J. M.; McAllister, T.W.; Yudofsky, S.C.; Eds.; American Psychiatric Publishing Inc.: Washington DC, 2005; p. 27-50. Exhibit F.
Giglio et al. Cerebral radiation necrosis, Neurologist, 9:180-188 (2003). Exhibit J.
Gravier et al., Thieno [2,3-d] pyrimidin-4(3H)-one Derivatives and 1,2-dihydrogenated Homologues: Synthesis, Enhanced In Vitro Antiaggregant Activity for Reduced Compounds, Pharmazie. 47(10): 757-757.1992.
Gryglewski, 2000, Journal of Physiology and Pharmacology, vol. 51, No. 4, p. 683-693.
Hahnen et al, 2008, Expert Opin. Investig. Drugs, vol. 17, p. 169-184.
Hitomi et al, 2008, Cell, vol. 135, p. 1311-1323.
International Preliminary Report on Patentability from International Application No. PCT/US2009/069483, issued Jun. 29, 2011.
International Search Report from International Application No. PCT/US2009/069483, mailed May 5, 2010.
Kaplowitz. Cell death at the millennium. Implications for liver diseases, Clin. Liver Dis. 4:1-22 (2000).
Kaplowitz. Mechanisms of liver cell injury, J. Hepatol. 32 (Suppl. 1), 39-47 (2000). Exhibit G.
Lo et al. Mechanisms, challenges and opportunities in stroke, Nat. Rev. Neurosci 4, 399-415 (2003). Exhibit C.
Malhi et al. Apoptosis and necrosis in the liver: a tale of two deaths, J. Hepatology, 43 (Suppl. 1):S31-S44 (2006). Exhibit H.
Manhas et al., Heterocyclic Compounds. 4. Synthesis and Antiinflammatory Activity of Some Substituted Thienopvrimidones, J. Med. Chem. 15(1): 106-107, 1972.
Mareninova et al. Cell death in pancreatitis. Caspases protect from necrotizing pancreatitis, J Biol. Chem. 281:3370-3381 (2006). Exhibit 0.
Martin et al. Neurodegeneration in excitotoxicity, global cerebral ischemia, and target deprivation: a perspective on the contributions of apoptosis and necrosis, Brain Res. Bull. 46:281-309 (1998). Exhibit P.
Max Robra et al., Chimie Organique. Synthese de tetrahydro-5.6. 7.8 benzo-(1)thieno-[2.3-cl] pyrimidines, C.R. Acad. Sc. Paris 276: 93-95, 1973.
McCully et al. Differential contribution of necrosis and apoptosis in myocardial ischemia-reperfusion injury, Am. J. Physiol. Heart Circ. Physiol. 286: H1923-H1935 (2004). Exhibit D.
Miyaguchi et al. Laryngeal necrosis after combined chemotherapy and radiation therapy, J Laryngol Otol,111:763-750 (1997) Exhibit L.

(56) References Cited

OTHER PUBLICATIONS

Osborne et al., Retinal ischemia: mechanisms of damage and potential therapeutic strategies, Prog. Retin. Eye Res.23:91-147 (2004). Exhibit E.
Ramesh et al. TNFR2-mediated apoptosis and necrosis in cisplatin-induced acute renal failure, Am. J. Physiol Renal Physiol. 285:F610-F618 (2003). Exhibit K.
Rosai. In Rosai and Ackerman's Surgical Pathology, 9th Edition; Mosby: New York, 2004; vol. 1, p. 1063-1067. Exhibit M.
Search Report issued in European Patent Application No. 09835866.6, dated Mar. 15, 2013.
Vanden Berghe et al., Necroptosis, necrosis, and secondary necrosis converge on similar cellular disintegration features, Cell Death and Differentiation, 17:922-930 (2010).
Wang et al., Structure-activity Relationship Analysis of a Novel Necroptosis Inhibitor, Necrostatin-5, Bioorg. Med. Chem. Lett. 17(5): 1455-1465, 2007.
Written Opinion from International Application No. PCT/US2009/069483, dated Apr. 29, 2010 (date of completion of search) and May 5, 2010 (date of mailing of report).
Wrobleski et al. Necrotizing pancreatitis: pathophysiology, diagnosis, and acute care management, AACN Clin. Issues 10:464-477 (1999). Exhibit N.
Yamaguchi et al., 3,4-Dihydrothienopyrimidines. II. 1) Synthesis and Sodium Borohydride Reduction of 2-Substituted 4-Chloro- and 4-Unsubstituted-thieno[2,3-cl]pyrimidines, Chem. Pharm. Bull. 30(1): 326-332, 1982.
Zheng et al., Structure-activity Relationship Study of a Novel Necroptosis Inhibitor, Necrostatin-7, Bioora. Med. Chem. Lett. 18(18): 4932-4935, 2008.

\* cited by examiner

SMALL MOLECULE INHIBITORS OF NECROPTOSIS

CROSS-REFERENCE TO RELATED APPLICATIONS

This application is a continuation of U.S. application Ser. No. 13/141,545, filed Sep. 9, 2011, which is the U.S. National Stage of International Application No. PCT/US2009/069483, filed Dec. 23, 2009, which claims benefit of U.S. Provisional Application No. 61/140,615, filed Dec. 23, 2008, each of which is hereby incorporated by reference.

STATEMENT AS TO FEDERALLY SPONSORED RESEARCH

This invention was made with government support under UO1 NS050560 awarded by the National Institutes of Health. The U.S. government has certain rights to this invention.

FIELD OF THE INVENTION

The invention relates to compounds and to cell death, in particular through necrosis and necroptosis, and regulation thereof by small molecules.

BACKGROUND OF THE INVENTION

In many diseases, cell death is mediated through apoptotic and/or necrotic pathways. While much is known about the mechanisms of action that control apoptosis, control of necrosis is not as well understood. Understanding the mechanisms regulating both necrosis and apoptosis in cells is essential to being able to treat conditions, such as neurodegenerative diseases, stroke, coronary heart disease, kidney disease, and liver disease. A thorough understanding of necrotic and apoptotic cell death pathways is also crucial to treating AIDS and the conditions associated with AIDS, such as retinal necrosis.

Cell death has traditionally been categorized as either apoptotic or necrotic based on morphological characteristics (Wylie et al., *Int. Rev. Cytol.* 68: 251 (1980)). These two modes of cell death were also initially thought to occur via regulated (caspase-dependent) and non-regulated processes, respectively. More recent studies, however, demonstrate that the underlying cell death mechanisms resulting in these two phenotypes are much more complicated and, under some circumstances, interrelated. Furthermore, conditions that lead to necrosis can occur by either regulated caspase-independent or non-regulated processes.

One regulated caspase-independent cell death pathway with morphological features resembling necrosis, called necroptosis, has recently been described (Degterev et al., *Nat. Chem. Biol.* 1:112 (2005)). This manner of cell death can be initiated with various stimuli (e.g., TNF-α and Fas ligand) and in an array of cell types (e.g., monocytes, fibroblasts, lymphocytes, macrophages, epithelial cells and neurons). Necroptosis may represent a significant contributor to and, in some cases, predominant mode of cellular demise under pathological conditions involving excessive cell stress, rapid energy loss, and massive oxidative species generation, where the highly energy-dependent apoptosis process is not operative.

The identification and optimization of low molecular weight molecules capable of inhibiting necroptosis will assist in elucidating its role in disease patho-physiology and could provide compounds (i.e., necrostatins) for anti-necroptosis therapeutics. The discovery of compounds that prevent caspase-independent cell death (e.g., necrosis or necroptosis) would also provide useful therapeutic agents for treating or preventing conditions in which necrosis occurs. These compounds and methods would be particularly useful for the treatment of neurodegenerative diseases, ischemic brain and heart injuries, and head trauma.

SUMMARY OF THE INVENTION

The invention features a series of heterocyclic derivatives that inhibit tumor necrosis factor alpha (TNF-α) induced necroptosis. The invention further features pharmaceutical compositions featuring necrostatins. The compounds and compositions of the invention may also be used to treat disorders where necroptosis is likely to play a substantial role.

In a first aspect, the invention features a compound having a structure according to the following formula:

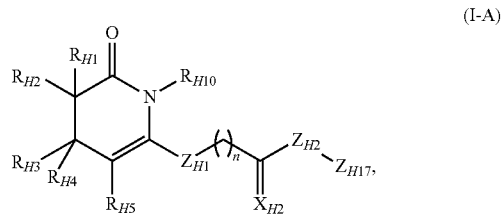

(I-A)

where each $R_{H1}$, $R_{H2}$, $R_{H3}$, $R_{H4}$, $R_{H5}$, $R_{H10}$, $R_{H17}$, $X_{H2}$, $Z_1$, $Z_{H2}$, and n is as defined for Formula (I), $X_{H2}$ is selected, independently, from O, S, or $NR_{H9}$;

each $R_{H1}$, $R_{H2}$, $R_{H3}$, $R_{H4}$, and $R_{H5}$ is selected, independently from H, halogen, cyano, nitro, azido, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted aryl, optionally substituted heterocyclyl, optionally substituted heteroaryl, —C(=O)$R_{H12}$, —C(=O)O$R_{H12}$, —C(=O)N$R_{H12}R_{H13}$, —C(=S)$R_{H12}$, —C(=S)N$R_{H12}R_{H13}$, —C(=N$R_{H14}$)$R_{H12}$, —C(=N$R_{H14}$)N$R_{H12}R_{H13}$, or —[$Z_{H1}$—(C$R_{H15}R_{H16}$)$_n$—{C(=$X_{H2}$)}$_n$—$Z_{H2}$—$R_{17}$], or $R_{H1}$ and $R_{H3}$ combine to form a carbon-carbon double bond;

each $Z_{H1}$ and $Z_{H2}$ is selected, independently, from a single bond, O, S, or $NR_{H11}$;

each $R_{H9}$, $R_{H10}$, $R_{H11}$, $R_{H12}$, $R_{H13}$, $R_{H14}$, $R_{H15}$, $R_{H16}$, and $R_{H17}$, is selected, independently from H, optionally substituted $C_{1-6}$ alkyl, optionally substituted $C_{3-10}$ cycloalkyl, optionally substituted aryl, optionally substituted heterocyclyl, or optionally substituted heteroaryl;

n is an integer between 0-6; and o is 0 or 1; and when $R_{H1}$ is H, $R_{H2}$ is H or $CO_2Me$, $R_{H3}$ is H, $R_{H4}$ is unsubstituted phenyl or phenyl substituted with 1, 2, or 3 substituents selected from methoxy, chloro, or fluoro, $R_{H5}$ is CN, $R_{H10}$ is H, $Z_{H1}$ is S, n is 1, $X_{H2}$ is O, and $Z_{H2}$ is NH, $R_{H17}$ is not H, methyl, methoxy, unsubstituted 2-thiazolyl, unsubstituted phenyl, 4-methoxyphenyl, 4-methylphenyl, 2-ethoxyphenyl, 4-isopropylphenyl, 4-fluorophenyl, or 2,4,6-trimethylphenyl, or any pharmaceutically acceptable salt or solvate thereof, or any stereoisomer thereof.

In some embodiments, the compound has a structure according to Formula (I-B)

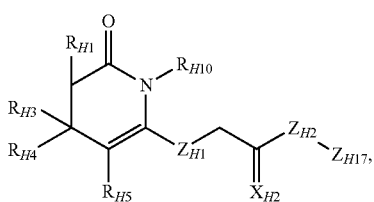

(I-B)

where each $R_{H1}$ and $R_{H3}$ is selected, independently, from H, halogen, cyano, nitro, azido, optionally substituted $C_{1-6}$ alkyl, optionally substituted $C_{3-10}$ cycloalkyl, optionally substituted aryl, optionally substituted heterocyclyl, optionally substituted heteroaryl, —C(=O)$R_{H12}$, —C(=O)OR$_{H12}$, or —C(=O)NR$_{H12}$R$_{H13}$, or $R_{H1}$ and $R_{H3}$ combine to form a carbon-carbon double bond;

each $R_{H4}$ and $R_{H17}$ is selected, independently, from optionally substituted aryl or optionally substituted heteroaryl;

$R_{H5}$ is selected from H, CN, —C(=O)OR$_{H12}$, or —C(=O)NR$_{H12}$R$_{H13}$;

each $R_{H10}$, $R_{H11}$, $R_{H12}$, and $R_{H13}$ is selected from H, optionally substituted $C_{1-6}$ alkyl, optionally substituted $C_{3-10}$ cycloalkyl, optionally substituted aryl, optionally substituted heterocyclyl, or optionally substituted heteroaryl;

$Z_{H1}$ is selected from a single bond or S;
$Z_{H2}$ is selected from a single bond or NR$_{H11}$; and
$X_{H2}$ is O or S;

or any pharmaceutically acceptable salt or solvate thereof, or any stereoisomer thereof.

In other embodiments, the compound has the following structure:

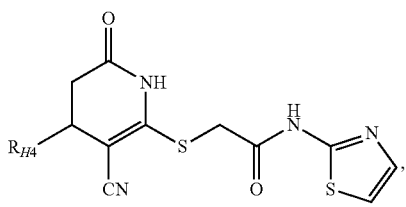

(I-C)

or any pharmaceutically acceptable salt or solvate thereof, or any stereoisomer thereof.

In some embodiments, $R_{H1}$ and $R_{H3}$ are H.
In some embodiments, $R_{H5}$ is CN.
In some embodiments, $R_{H10}$ is H.
In some embodiments, $Z_{H1}$ is S.
In some embodiments, $Z_{H2}$ is NH,
In some embodiments, $R_{H4}$ is unsubstituted phenyl or phenyl having 1, 2, 3, 4, or 5 substituents. In further embodiments, the phenyl includes 1, 2, or 3 substituents selected from F, Cl, or OR$_{H18}$, where each $R_{H18}$ is, independently, selected from H or optionally substituted $C_{1-6}$ alkyl. In certain embodiments, the phenyl is 2-fluorophenyl, 2-chlorophenyl, 4-fluorophenyl, 4-chlorophenyl, 2-methoxyphenyl, 3,4,5-trimethoxyphenyl, or 3,4-dimethoxyphenyl.

In some embodiments, $R_{H17}$ is optionally substituted heteroaryl. In certain embodiments, heteroaryl selected from furan, thiophene, pyrrole, 1,2,3-thiadiazole, 1,2,4-thiadiazole, 1,2,3-oxadiazole or 1,2,5-oxadiazole, oxazole, benzoxazole, isoxazole, isothiazole, pyrazole, thiazole, benzthiazole, 1,2,4-triazole, 1,2,3-triazole, benzotriazole, pyridine, pyrimidine, pyrazines, quinoline, isoquinoline, purine, pyrazine, pteridine, 1,2,3-triazine, 1,2,4-triazine, 1,3,5-triazine, indole, 1,2,4,5-tetrazine, benzo[b]thiophene, benzo[c]thiophene, benzofuran, isobenzofuran, and benzimidazole.

In a second aspect, the invention features a compound having a structure according to the following formula

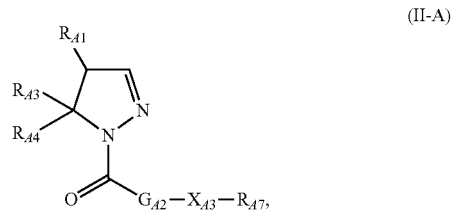

(II-A)

where each $R_{A1}$, $R_{A3}$, and $R_{A4}$ is selected, independently, from H, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl, or $R_{A1}$ and $R_{A4}$ combine to form a carbon-carbon double bond;

$G_{A2}$ is absent or —(CR$_{A11}$R$_{A12}$)$_n$—;
$X_{A3}$ is absent or is O, S, or NR$_{A8}$;

each $R_{A8}$ and $R_{A13}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl, —COR$_{A14}$, —CO$_2$R$_{A14}$, or —CONR$_{A14}$R$_{A15}$;

each $R_{A9}$, $R_{A10}$, $R_{A11}$, and $R_{A12}$ is selected, independently, from H, halogen, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl;

each $R_{A7}$, $R_{A14}$ and $R_{A15}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl; and each m and n is, independently, 1, 2, or 3; and where when one of $R_{A1}$ and $R_{A4}$ is H and the other is selected from H or CO$_2$Et, and $R_{A3}$ is unsubstituted phenyl, $G_{A2}$-$X_{A3}$—$R_{A7}$ is not NHC$_6$H$_5$, NH(p-C$_6$H$_4$F), NH(p-C$_6$H$_4$OH), NH(p-C$_6$H$_4$OMe), NH(3-OH-4-C$_1$-C$_6$H$_4$), —CH$_2$(O-p-C$_6$H$_4$Me), —CH$_2$(4-ethylpiperazinyl), —CH$_2$S (2-phenyltetrazolyl), —CH$_2$S(4-chlorophenyl), —CH$_2$S(2-benzothiazolyl), —CH$_2$S(2-(N-methylimidazolyl)), —CH$_2$S(4,6-dimethylquinazolinyl), adamantyl, or optionally substituted oxiranyl; and where when $R_{A1}$ and $R_{A4}$ are each H and $R_{A3}$ is 4-methoxyphenyl, $G_{A2}$-$X_{A3}$—$R_{A7}$ is not optionally substituted oxiranyl;

or any pharmaceutically acceptable salt or solvate thereof, or any stereoisomer thereof.

In some embodiments, $R_{A1}$ and $R_{A4}$ are H.
In some embodiments, $R_{A3}$ is unsubstituted phenyl.

In some embodiments, $R_{A3}$ is phenyl having 1, 2, 3, 4, or 5 substituents.

In some embodiments, $G_{A2}$ is absent.

In certain embodiments, $X_{A3}$ is absent and $R_{A7}$ is optionally substituted $C_{3-10}$ cycloalkyl, optionally substituted heterocyclyl, optionally substituted aryl, or optionally substituted heteroaryl.

In other embodiments, $X_{A3}$ is $NR_{A8}$ and $R_{A7}$ is optionally substituted $C_{3-10}$ cycloalkyl, optionally substituted heterocyclyl, optionally substituted aryl, or optionally substituted heteroaryl.

In some embodiments, $G_{A2}$ is $CH_2$.

In some embodiments, $X_{A3}$ is S and $R_{A7}$ is optionally substituted $C_{3-10}$ cycloalkyl, optionally substituted heterocyclyl, optionally substituted aryl, or optionally substituted heteroaryl.

In some embodiments, $X_{A3}$ is absent and $R_{A7}$ is optionally substituted $C_{3-10}$ cycloalkyl, optionally substituted heterocyclyl, optionally substituted aryl, or optionally substituted heteroaryl.

In a third aspect, the invention features compounds according to the following formula

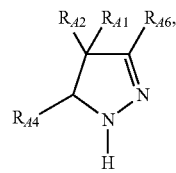

(II-C)

where each $R_{A1}$, $R_{A2}$, $R_{A4}$, and $R_{A6}$ is selected, independently, from H, —C(=O)—$X_{A3}$—$R_{A7}$, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl, or $R_{A1}$ and $R_{A4}$ combine to form a carbon-carbon double bond;

each $X_{A3}$ is, independently, absent, —O—, or —$NR_{A8}$—, each $R_{A8}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl, —$COR_{A14}$, —$CO_2R_{A14}$, or —$CONR_{A14}R_{A15}$;

each $R_{A7}$, $R_{A14}$ and $R_{A15}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl; and wherein when $R_{A1}$ and $R_{A4}$ combine to form a carbon-carbon double bond and $R_{A2}$ is H, $R_{A6}$ is not 4-chlorophenyl, 4-methoxyphenyl, or 4-(NHCO$_2^t$Bu)phenyl; and where when $R_{A1}$ is H, $R_{A4}$ is H or CO$_2$Et, $R_{A2}$ is unsubstituted phenyl, $R_{A6}$ is not —C(=O)-(unsubstituted phenyl) or —C(=O)-(4-methylphenyl); and where when $R_{A1}$ is H, $R_{A4}$ is —C(=O)-(unsubstituted phenyl), $R_{A2}$ is 4-chlorophenyl, $R_{A6}$ is not CO$_2$Et;

or any pharmaceutically acceptable salt or solvate thereof, or any stereoisomer thereof.

In some embodiments, $R_{A5}$ is H; each $R_{A1}$, $R_{A2}$, $R_{A4}$, and $R_{A6}$ is selected, independently, from H, optionally substituted aryl, optionally substituted heteroaryl, —C(=O)—$X_{A3}$—$R_{A7}$, or $R_{A1}$ and $R_{A4}$ combine to form a carbon-carbon double bond; each $R_{A7}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl; and each $X_{A3}$ is, independently, absent, —O—, or —$NR_{A8}$—, or any pharmaceutically acceptable salt or solvate thereof, or any stereoisomer thereof.

In certain embodiments, $R_{A1}$ and $R_{A4}$ combine to form a carbon-carbon double bond.

In other embodiments, $R_{A6}$ is optionally substituted aryl or optionally substituted heteroaryl.

In some embodiments, $R_{A6}$ is a phenyl group having a substituent at the 4-position.

In certain embodiments, $R_{A1}$ and $R_{A4}$ are each H, $R_{A2}$ is optionally substituted aryl or optionally substituted heteroaryl, and $R_{A6}$ is —C(=O)—$X_{A3}$—$R_{A7}$.

In other embodiments, $R_{A2}$ is unsubstituted phenyl.

In a fourth aspect, the invention features a compound having a structure according to the following formula:

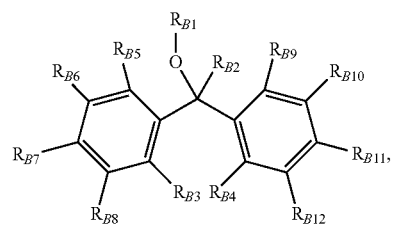

(III)

where $R_{B1}$ is selected from H, optionally substituted $C_{1-6}$ alkyl, —C(=O)$R_{B18}$, —C(=O)O$R_{B18}$, or —C(=O)N$R_{B18}R_{B19}$;

$R_{B2}$ is selected from H, optionally substituted $C_{1-6}$ alkyl, optionally substituted $C_{2-6}$ alkenyl, or optionally substituted $C_{2-6}$ alkynyl;

each $R_{B3}$ and $R_{B4}$ is selected, independently from H, optionally substituted $C_{1-6}$ alkyl, or $R_{B3}$ and $R_{B4}$ combine to form a bridging group having the structure —(CH$_2$)$_n$—(CR$_{B13}$=CR$_{B14}$)$_o$—(CH$_2$)$_p$—;

each n, o, and p is, independently, 0 or 1;

each $R_{B5}$, $R_{B6}$, $R_{B7}$, $R_{B8}$, $R_{B9}$, $R_{B10}$, $R_{B11}$, and $R_{B12}$ is selected, independently, from H, halogen, —CN, —NO$_2$, —N$_3$, —$R_{B13}$, —O$R_{B13}$, —S$R_{B13}$, —N$R_{B13}R_{B14}$, —C(O)$R_{B15}$, —C(=O)O$R_{B15}$, —C(=O)N$R_{B15}R_{B16}$, —OC(=O)$R_{B15}$, —OC(=O)O$R_{B15}$, —OC(=O)N$R_{B15}R_{B16}$, —N$R_{B15}$C(=O)$R_{B15}$, —N$R_{B15}$C(=O)O$R_{B16}$, —N$R_{B15}$C(=O)N$R_{B16}R_{B17}$, —C(=S)$R_{B15}$, —C(=S)N$R_{B15}R_{B16}$, —N$R_{B15}$C(=S)$R_{B16}$, —N$R_{B15}$C(=S)N$R_{B16}R_{B17}$, —C(=N$R_{B13}$)N$R_{B15}R_{B16}$, —N$R_{B15}$C(=N$R_{B13}$)$R_{B16}$, —N$R_{B15}$C(=N$R_{B13}$)N$R_{B16}R_{B17}$;

each $R_{B13}$ and $R_{B14}$ is selected, independently, from H, optionally substituted $C_{1-6}$ alkyl, optionally substituted $C_{3-10}$ cycloalkyl, optionally substituted aryl, optionally substituted heteroaryl, —C(=O)$R_{B18}$, —C(=O)O$R_{B18}$, or —C(=O)N$R_{B18}R_{B19}$;

each $R_{B15}$, $R_{B16}$, $R_{B17}$, $R_{B18}$, and $R_{B19}$ is selected, independently, from H, optionally substituted $C_{1-6}$ alkyl, optionally substituted $C_{3-10}$ cycloalkyl, optionally substituted aryl, or optionally substituted heteroaryl;

where when each n, o, and p is 0, $R_{B3}$ and $R_{B4}$ combine to form a single bond, and where $R_{B1}$ is not H or CH$_3$ when $R_{B5}$, $R_{B6}$, $R_{B7}$, $R_{B8}$, $R_{B9}$, $R_{B10}$, $R_{B11}$, and $R_{B12}$ are each H, $R_{B2}$ is ethyl, ethenyl, 2-haloethenyl, ethynyl, haloethynyl, propynyl, or —C≡C—C(OH)(CH$_3$)$_2$, and when $R_{B3}$ and $R_{B4}$ are each H or combine to form a bond, —CH$_2$CH$_2$— or —CH=CH—;

where $R_{B1}$ is not H when $R_{B5}$, $R_{B6}$, $R_{B7}$, $R_{B8}$, $R_{B10}$, and $R_{B11}$ are each H, at least one of $R_{B9}$ or $R_{B12}$ is fluoro, $R_{B2}$ is ethynyl, and when $R_{B3}$ and $R_{B4}$ combine to form —CH$_2$CH$_2$—;

wherein $R_{B1}$ is not H when $R_{B5}$, $R_{B7}$, $R_{B9}$, and $R_{B11}$ are H and one or two of $R_{B6}$, $R_{B8}$, $R_{B10}$, and $R_{B12}$ is halogen, nitro, or methyl;

or any pharmaceutically acceptable salt or solvate thereof, or any stereoisomer thereof.

In some embodiments, $R_{B1}$ is H.

In some embodiments, $R_{B2}$ is $C_{1-3}$ alkyl.

In certain embodiments, $R_{B2}$ is $C_{1-3}$ alkenyl.

In other embodiments, $R_{B2}$ is ethynyl.

In some embodiments, $R_{B3}$ and $R_{B4}$ are each H.

In certain embodiments, the compound has the following structure

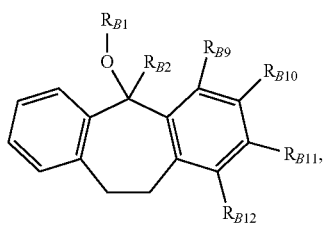

(III-A)

where $R_{B2}$ is ethyl, ethenyl, or ethynyl and each $R_{B9}$, $R_{B10}$, $R_{B11}$, and $R_{B12}$ is selected, independently, from H and halogen, or any pharmaceutically acceptable salt or solvate thereof, or any stereoisomer thereof. In some embodiments, $R_{B10}$ or $R_{B12}$ is fluoro.

In some embodiments, the compound has the following structure:

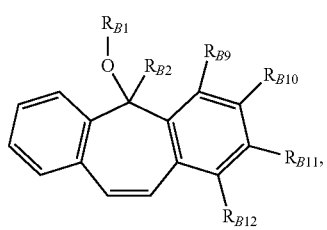

(III-B)

where $R_{B2}$ is ethyl, ethenyl, or ethynyl and each $R_{B9}$, $R_{B10}$, $R_{B11}$, and $R_{B12}$ is selected, independently, from H and halogen, or any pharmaceutically acceptable salt or solvate thereof, or any stereoisomer thereof.

In a fifth aspect, the invention features a structure according to the following formula

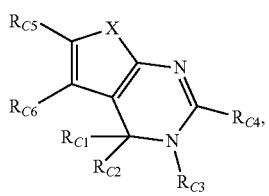

where each $R_{C1}$, $R_{C2}$, and $R_{C3}$ is selected, independently, from H, optionally substituted $C_{1-6}$ alkyl, —Y—$R_{C7}$, or $R_{C1}$ and $R_{C2}$ combine to form a (=O) or a (=S) group, or $R_{C1}$ and $R_{C3}$ combine to form a carbon-nitrogen double bond;

$R_{C4}$ is selected from H, halogen, —CN, optionally substituted $C_{1-6}$ alkyl, optionally substituted $C_{3-10}$ cycloalkyl, optionally substituted heterocyclyl, optionally substituted aryl, optionally substituted heteroaryl, or —C(=O)Z$R_{C8}$, each $R_{C5}$ and $R_{C6}$ is selected, independently, from H, optionally substituted $C_{1-6}$ alkyl, or $R_{C5}$ and $R_{C6}$ combine to form an optionally substituted $C_{3-10}$ cycloalkyl, optionally substituted heterocyclyl, optionally substituted aryl, or optionally substituted heteroaryl;

each $R_{C7}$, $R_{C8}$, $R_{C9}$, $R_{C10}$, $R_{C11}$, and $R_{C12}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl;

X is —CR$_{C11}$=CR$_{C12}$—, O, S, or NR$_{C9}$;

Y is, independently, a single bond, (CR$_{C8}$R$_{C9}$)$_n$, O, S, or NR$_{C10}$; and Z is a single bond, O, S, or NR$_{C10}$;

n is an integer between 0-4; and where when X is S, $R_{C1}$ and $R_{C2}$ combine to form a (=O) group, $R_{C4}$ is H, and $R_{C5}$ and $R_{C6}$ combine to form unsubstituted cyclopentyl, $R_{C3}$ is not —CH$_2$—$R_{C7}$, where $R_{C7}$ is unsubstituted phenyl, unsubstituted naphthyl, unsubstituted 8-quinolyl, unsubstituted 2-oxoquinolyl, or phenyl having 1 or 2 substituents selected from F, OMe, Me, CN, or Cl; and wherein when X is S, $R_{C1}$ and $R_{C2}$ combine to form a (=O) group, $R_{C4}$ is H, and $R_{C5}$ and $R_{C6}$ are each CH$_3$, $R_{C3}$ is not —CH$_2$—$R_{C7}$, where $R_{C7}$ is unsubstituted phenyl; and where when X is CH=CH, $R_{C1}$ and $R_{C2}$ combine to form a (=O) group, $R_{C4}$ is H, and $R_{C5}$ and $R_{C6}$ are H, $R_{C3}$ is not —CH$_2$(4-halophenyl);

or any pharmaceutically acceptable salt or solvate thereof, or any stereoisomer thereof.

In some embodiments, each $R_{C5}$ and $R_{C6}$ is optionally substituted $C_{1-6}$ alkyl.

In other embodiments, the compound has a structure according to the following formula:

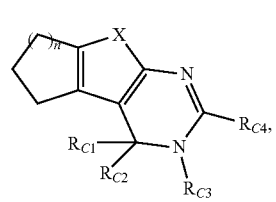

(IV-A)

wherein X, $R_{C1}$, $R_{C2}$, $R_{C3}$, and $R_{C4}$ are as defined for Formula (IV) and n is an integer between 0-3, or any pharmaceutically acceptable salt or solvate thereof, or any stereoisomer thereof.

In some embodiments, $R_{C1}$ and $R_{C7}$ combine to form a (=O) group.

In other embodiments, X is S.

In some embodiments, n is 1.

In certain embodiments, $R_{C3}$ is —Y—$R_{C5}$.

In other embodiments, $R_{C3}$ is —(CH$_2$)-(optionally substituted aryl).

In a sixth aspect, the invention features a compound having a structure according to the following formula

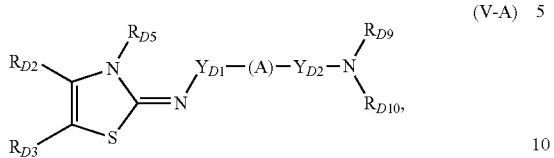

(V-A)

where
each $Y_{D1}$ and $Y_{D2}$ is selected, independently, from —C(=O)— or —S(=O)$_2$—;

A is phenyl having 0, 1, 2, 3, or 4 additional substituents;

$R_{D2}$ and $R_{D3}$ are selected, independently from H, halogen, CN, NC, N$_3$, NO$_2$, —COR$_{D13}$, —CO$_2$R$_{D11}$, —CONR$_{D13}$R$_{D14}$, optionally substituted C$_{1-6}$ alkyl, optionally substituted C$_{3-10}$ cycloalkyl, optionally substituted heterocyclyl, optionally substituted aryl, or optionally substituted heteroaryl;

each $R_{D5}$, $R_{D9}$, $R_{D10}$, $R_{D13}$, and $R_{D14}$ is selected, independently, from H, optionally substituted C$_{1-6}$ alkyl, optionally substituted C$_{3-10}$ cycloalkyl, optionally substituted heterocyclyl, optionally substituted aryl, or optionally substituted heteroaryl, or $R_{D9}$ and $R_{D10}$ combine to form a heterocyclyl; and where when $R_{D2}$, $R_{D3}$, and $R_{D5}$ are H, $Y_{D1}$ is —(C=O)—, $Y_{D2}$ is —(SO$_2$)—, and $R_{D9}$ and $R_{D10}$ are each ethyl or $R_{D9}$ is methyl and $R_{D10}$ is CH$_2$(2-tetrahydrofuran), and A is phenyl having 0 additional substituents, $Y_{D1}$ and $Y_{D2}$ are not para to each other, or any pharmaceutically acceptable salt or solvate thereof, or any stereoisomer thereof.

In some embodiments, $Y_{D1}$ and $Y_{D2}$ are ortho or meta to each other.

In other embodiments, $Y_{D1}$ and $Y_{D2}$ are para to each other.

In some embodiments, the compound has a structure according to the following formula

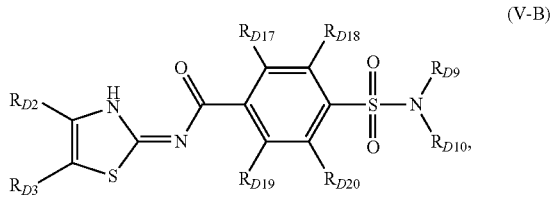

(V-B)

where
each $R_{D2}$, $R_{D3}$, $R_{D17}$, $R_{D18}$, $R_{D19}$, and $R_{D20}$, is selected, independently from H, halogen, CN, NC, N$_3$, NO$_2$, —COR$_{D13}$, —CO$_2$R$_{D13}$, —CONR$_{D13}$R$_{D14}$, optionally substituted C$_{1-6}$ alkyl, optionally substituted aryl, or optionally substituted heteroaryl; and each $R_{D9}$ and $R_{D10}$ is selected, independently, from H, optionally substituted C$_{1-6}$ alkyl, optionally substituted C$_{3-10}$ cycloalkyl, or optionally substituted aryl, or $R_{D9}$ and $R_{D10}$ combine to form a heterocyclyl;

or any pharmaceutically acceptable salt or solvate thereof, or any stereoisomer thereof.

In some embodiments, $R_{D17}$, $R_{D18}$, $R_{D19}$, and $R_{D20}$ are H.

In some embodiments, $R_{D2}$ and $R_{D3}$ are H.

In other embodiments, $R_{D9}$ and $R_{D10}$ are each optionally substituted C$_{1-6}$ alkyl.

In a seventh aspect, the invention features a compound having a structure according to

(VI-A)

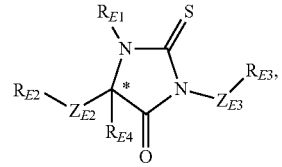

(VI-B)

where
each $Z_{E2}$ and $Z_{E3}$ is selected, independently, from a single bond, —(CR$_{E6}$R$_{E7}$)$_n$—, —C(=O)—, or $R_{E1}$ and $Z_{E2}$—R$_{E2}$ combine to form a double bond;

each $R_{E1}$, $R_{E2}$, and $R_{E4}$ is selected, independently, from H, optionally substituted C$_{1-6}$ alkyl, optionally substituted C$_{3-10}$ cycloalkyl, optionally substituted heterocyclyl, optionally substituted aryl, or optionally substituted heteroaryl;

$R_{E3}$ is selected from optionally substituted C$_{3-10}$ cycloalkyl, optionally substituted heterocyclyl, optionally substituted aryl, or optionally substituted heteroaryl;

each $R_{E6}$ and $R_{E7}$ is selected, independently, from H or optionally substituted C$_{1-6}$ alkyl; and each n is an integer between 1-6; and where when $R_{E1}$ and $R_{E4}$ are H, $Z_{E2}$ and $Z_{E3}$ are each CH$_2$, and $R_{E2}$ is unsubstituted 3-indolyl, $R_{E3}$ is not 4-chlorophenyl or CH$_2$CH$_2$O(p-C$_6$H$_4$F), or any pharmaceutically acceptable salt or solvate thereof, or any stereoisomer thereof.

In some embodiments, the compound has a structure according to

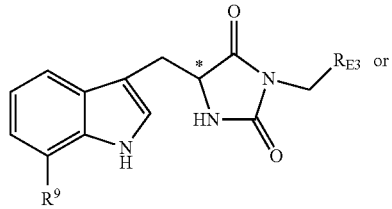

(VI-D-3)

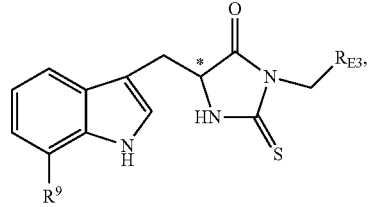

(VI-D-4)

where
$R_{E3}$ is optionally substituted aryl or optionally substituted heteroaryl; and $R^9$ is H, halogen, CN, NO$_2$, OR$^{13}$, NR$^{13}$R$^{14}$, COR$^{15}$, CO$_2$R$^{15}$, or optionally substituted C$_{1-6}$ alkyl;

each $R^{13}$ and $R^{14}$ is selected, independently, from H, $COR^{16}$, $CO_2R^{16}$, optionally substituted $C_{1-6}$ alkyl, optionally substituted $C_{3-10}$ cycloalkyl, optionally substituted heterocyclyl, optionally substituted aryl, or optionally substituted heteroaryl; and, each $R^{15}$ and $R^{16}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl;

or any pharmaceutically acceptable salt or solvate thereof, or any stereoisomer thereof.

In some embodiments, $R_{E3}$ is optionally substituted aryl.

In some embodiments, $R_{E3}$ is unsubstituted $C_{3-10}$ cycloalkyl, unsubstituted heterocyclyl, unsubstituted aryl, or unsubstituted heteroaryl.

In other embodiments, $R_{E3}$ is substituted $C_{3-10}$ cycloalkyl, substituted heterocyclyl, substituted aryl, or substituted heteroaryl. In other embodiments, the substituted $C_{3-10}$ cycloalkyl, substituted heterocyclyl, substituted aryl, or substituted heteroaryl includes 1, 2, 3, 4, or 5 substituents selected, independently, from the group consisting of: $C_{1-6}$ alkyl, $C_{2-6}$ alkenyl, $C_{2-6}$ alkynyl, cycloalkyl, cycloalkenyl, heterocyclyl, aryl, heteroaryl, —$N_3$, —OR', —NR'C(=O)R'', —C(=O)NRR', —NRR', —OC(=O)NR'R'', —NRC(=O)OR', —OH, and —NC), wherein each R or R' is selected, independently, from H, $C_{1-6}$ alkyl, $C_{2-6}$ alkenyl, $C_{2-6}$ alkynyl, cycloalkyl, heterocyclyl, aryl, or heteroaryl.

In still other embodiments, $R_{E3}$ is substituted aryl or substituted heteroaryl. In some embodiments, $R_{E3}$ is substituted phenyl. In some embodiments, the substituted phenyl is substituted with at least one halogen. In other embodiments, the substituted phenyl is substituted with 1, 2, 3, 4, or 5 substituents selected, independently, from the group consisting of: $C_{1-6}$ alkyl, $C_{2-6}$ alkenyl, $C_{2-6}$ alkynyl, cycloalkyl, cycloalkenyl, heterocyclyl, aryl, heteroaryl, —$N_3$, —OR', —NR'C(=O)R'', —C(=O)NRR', —NRR', —OC(=O)NR'R'', —NRC(=O)OR', —OH, and —NC), wherein each R or R' is selected, independently, from H, $C_{1-6}$ alkyl, $C_{2-6}$ alkenyl, $C_{2-6}$ alkynyl, cycloalkyl, heterocyclyl, aryl, or heteroaryl.

In some embodiments, the stereocenter marked by the asterisk in the compound of Formula (VI) has the (R)-configuration. In other embodiments, the stereocenter marked by the asterisk has the (S)-configuration.

In any of the embodiments described herein, one or both of —$Z_{E3}$ and $R_{E3}$ does not include substituents selected from the group consisting of: halogen (e.g., F, Cl, Br, or I); nitro (—$NO_2$), cyano (—CN), acyloxy(=OC(=O)R'), acyl (—C(=O)R'), carboxylic acid (—$CO_2H$), carboxylic ester (—$CO_2R'$), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, cycloalkyl, heterocyclyl, aryl, or heteroaryl, as described herein.

In an eighth aspect, the invention features a compound having a structure according to the following formula,

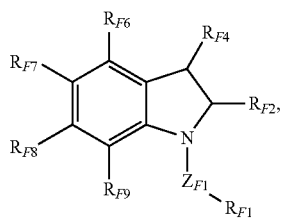

(VII-A)

where $Z_{F1}$ is selected from a single bond, —($CH_2$)—, —C(=O)—, or —S(=O)$_2$—;

$R_{F1}$ is selected from H, $OR_{F14}$, optionally substituted $C_{3-10}$ cycloalkyl, optionally substituted heterocyclyl, optionally substituted aryl, or optionally substituted heteroaryl;

$R_{F2}$ and $R_{F4}$ are each H, or $R_{F2}$ and $R_{F4}$ combine to form a carbon-carbon double bond;

each $R_{F6}$, $R_{F7}$, $R_{F8}$, and $R_{F9}$ is selected, independently, from H, halogen, CN, NC, $N_3$, $NO_2$, $OR_{F12}$, $SR_{F12}$, $NR_{F12}R_{F13}$, —$COR_{F12}$, —$CO_{2 F12}$, —$CONR_{F12}R_{F13}$, optionally substituted $C_{1-6}$ alkyl, optionally substituted $C_{3-10}$ cycloalkyl, optionally substituted heterocyclyl, optionally substituted aryl, or optionally substituted heteroaryl; and each $R_{F12}$, $R_{F13}$, and $R_{F14}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl; and where when $R_{F2}$, $R_{F4}$, $R_{F6}$, $R_{F7}$, $R_{F8}$, and $R_{F9}$ are each H and $Z_{F1}$ is —C(=O)—, $R_{F1}$ is not -(unsubstituted 1,4-benzodioxane) or —$CH_2$—O-(unsubstituted phenyl), or —$CH(CH_3)O$(o-tolyl);

or any pharmaceutically acceptable salt or solvate thereof, or any stereoisomer thereof.

In some embodiments, $R_{F2}$ and $R_{F4}$ are each H.

In other embodiments, $R_{F6}$, $R_{F7}$, $R_{F8}$, and $R_{F9}$ are H.

In certain embodiments, $Z_{F1}$ is —C(=O)—. In further embodiments, $R_{F1}$ is optionally substituted heterocyclyl, optionally substituted aryl, or optionally substituted heteroaryl.

In a ninth aspect, the invention features a compound having a structure according to the following formula

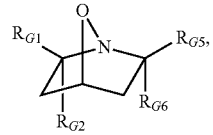

(VIII-A)

where each $R_{G1}$, $R_{G2}$, $R_{G5}$, and $R_{G6}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl, or $R_{G1}$ and $R_{G2}$, or $R_{G5}$ and $R_{G6}$ combine to form an optionally substituted cycloalkyl or heterocyclyl; and where when $R_{G1}$ is unsubstituted phenyl and $R_{G2}$ is H, $R_{G5}$ and $R_{G6}$ do not combine to form unsubstituted cyclopentyl;

or any pharmaceutically acceptable salt or solvate thereof, or any stereoisomer thereof.

In some embodiments, $R_{G1}$ or $R_{G5}$ is phenyl having 0, 1, 2, 3, 4, or 5 substituents. In certain embodiments, $R_{G1}$ is unsubstituted phenyl.

In some embodiments, $R_{G2}$ or $R_{G6}$ is phenyl having 0, 1, 2, 3, 4, or 5 substituents.

In other embodiments, $R_{G1}$ and $R_{G2}$, or $R_{G5}$ and $R_{G6}$ combine to form an optionally substituted cycloalkyl. In certain embodiments, the cycloalkyl is cyclopropyl, cyclobutyl, cyclopentyl, or cyclohexyl.

In a tenth aspect, the invention features a pharmaceutical composition including a pharmaceutically acceptable excipient and any compound of Formulas (I)-(VIII), or any of Compounds (1)-(7), (13)-(26), (27)-(33), (48)-(57), and (58)-(70), or any pharmaceutically acceptable salt or solvate thereof, or stereoisomer thereof.

In an eleventh aspect, the invention features a method of treating a condition in a subject, with the method including the step of administering the compound of any compound of Formulas (I)-(VIII), or any of Compounds (1)-(7), (13)-(26), (27)-(33), (48)-(57), and (58)-(70), or any pharmaceutically acceptable salt or solvate thereof, or stereoisomer thereof, to said subject in a dosage sufficient to decrease necroptosis.

In some embodiments, the condition is a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, or any condition in which alteration in cell proliferation, differentiation or intracellular signaling is a causative factor.

In some embodiments, the condition is a neurodegenerative disease of the central or peripheral nervous system.

In some embodiments, the condition is hepatic or brain ischemic injury, or ischemic injury during organ storage, head trauma, septic shock, or coronary heart disease.

In some embodiments, the condition is stroke.

In some embodiments, the condition is myocardial infarction.

In a twelfth aspect, the invention features a method of decreasing necroptosis, where the method includes contacting a cell with any compound of Formulas (I)-(VIII), or any of Compounds (1)-(7), (13)-(26), (27)-(33), (48)-(57), and (58)-(70)), or any pharmaceutically acceptable salt or solvate thereof, or stereoisomer thereof.

In a thirteenth aspect, the invention features a kit including (a) a pharmaceutical composition comprising any compound of Formulas (I)-(VIII), or any of Compounds (1)-(7), (13)-(26), (27)-(33), (48)-(57), and (58)-(70), or any pharmaceutically acceptable salt or solvate thereof, or stereoisomer thereof; and (b) instructions for the use of the pharmaceutical composition of (a) to treat a condition in a subject.

In any of the compositions, methods, and kits of the invention, the compound can be selected from the group consisting of:

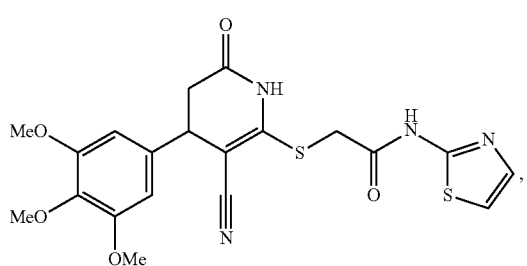

-continued

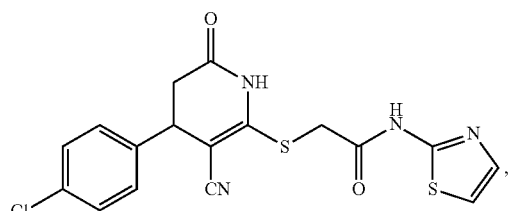

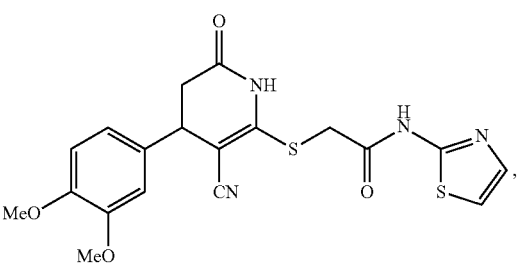

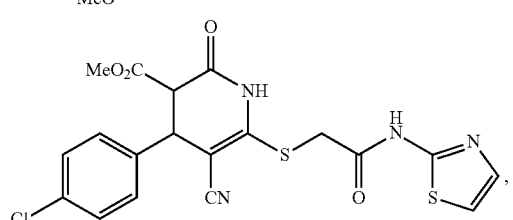

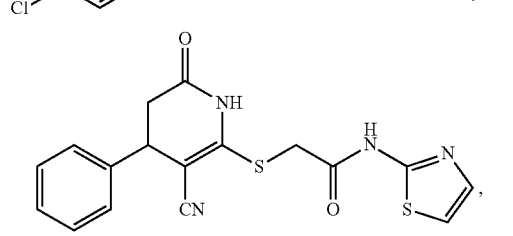

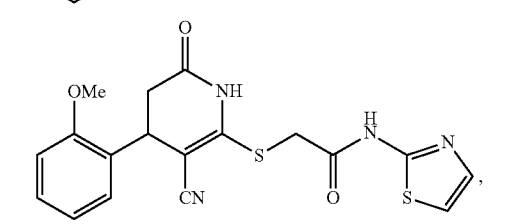

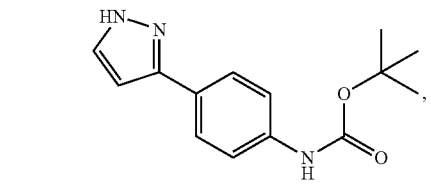

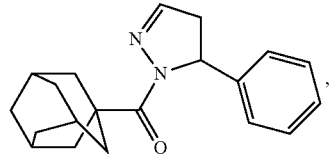

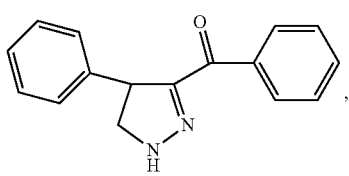

15
-continued
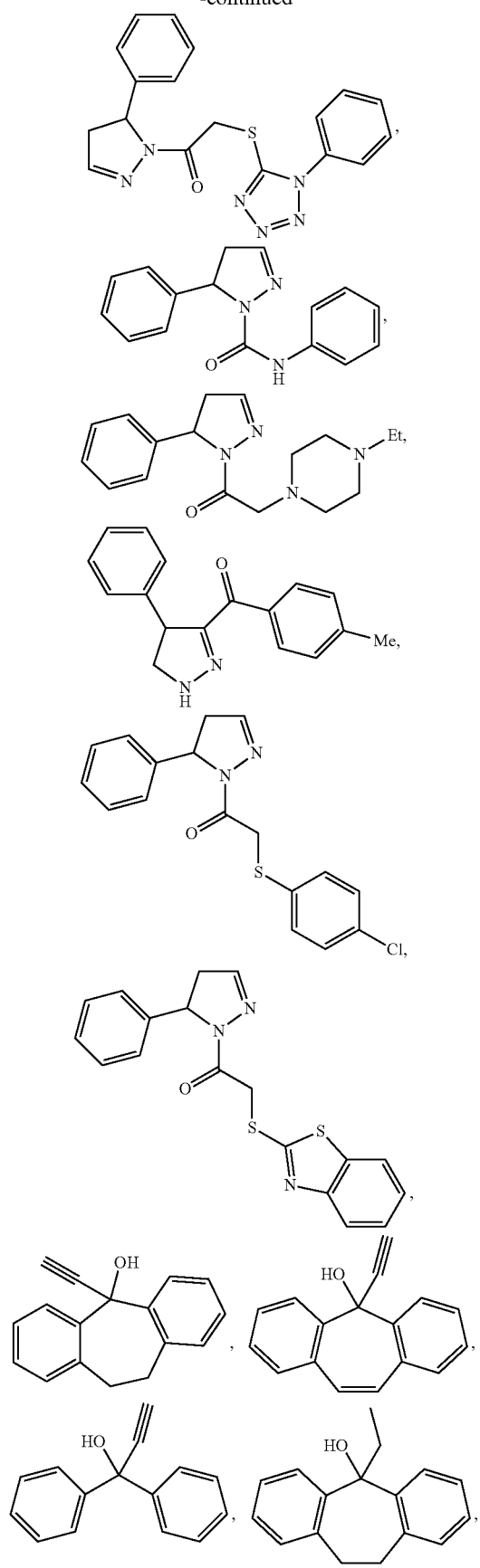
16
-continued
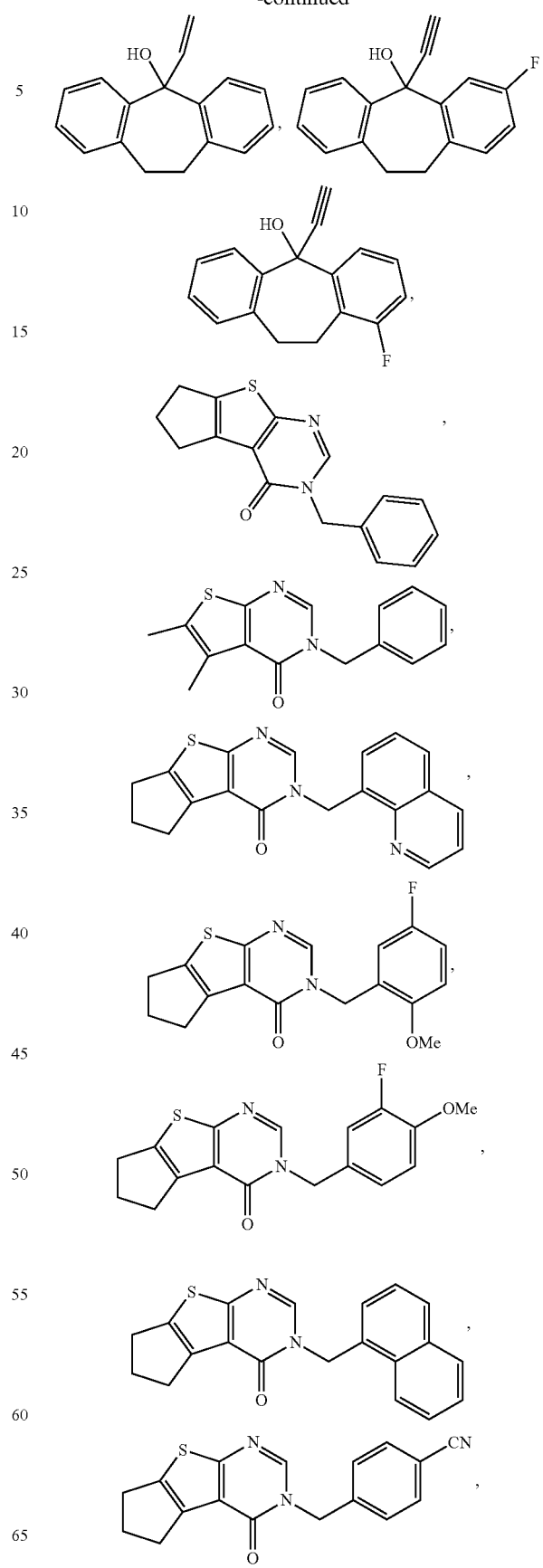

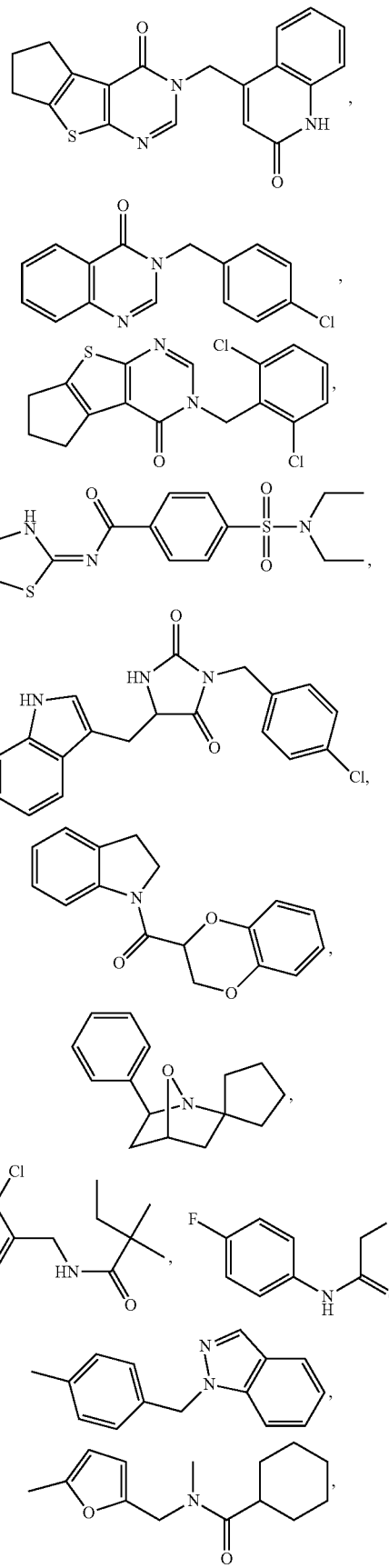

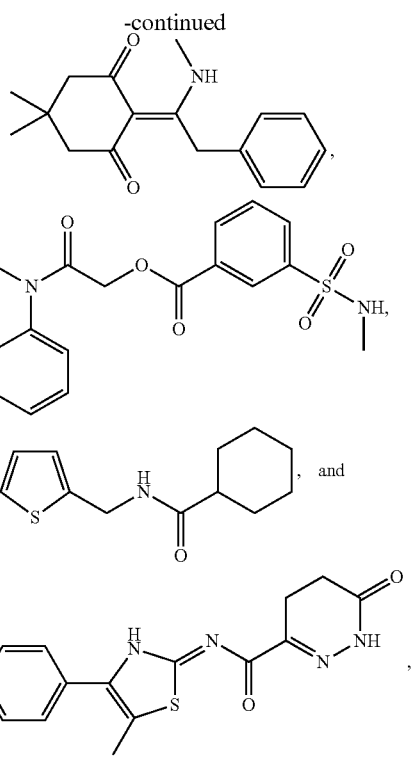

or any pharmaceutically acceptable salt or solvate thereof, or stereoisomer thereof.

By "$C_{1-4}$ alkaryl" is meant a $C_{1-4}$ alkyl group having an optionally substituted aryl or an optionally substituted heteroaryl located at any position of the carbon chain. The $C_{1-4}$ alkyl group may be linear or branched and may also be substituted with, for example, 1, 2, 3, 4, or 5 additional substituents as described herein.

By "alkoxy" is meant a group having the structure —O(optionally substituted $C_{1-6}$ alkyl), where the optionally substituted $C_{h6}$ alkyl may be branched, linear, or cyclic. The $C_{1-6}$ alkyl may be substituted or unsubstituted. A substituted $C_{1-6}$ alkyl can have, for example, 1, 2, 3, 4, 5, or 6 substituents located at any position. Exemplary alkoxy groups include, but are not limited to, methoxy, ethoxy, propoxy, isopropoxy, tert-butoxy, and the like.

By "$C_{2-6}$ alkenyl" or "alkenyl" is meant an optionally substituted unsaturated $C_{2-6}$ hydrocarbon group having one or more carbon-carbon double bonds. Exemplary $C_{2-6}$ alkenyl groups include, but are not limited to —CH=CH (ethenyl), propenyl, 2-propenyl, 2-methyl-1-propenyl, 1-butenyl, 2-butenyl, and the like. A $C_{2-6}$ alkenyl may be linear or branched and may be unsubstituted or substituted. A substituted $C_{2-6}$ alkenyl may have, for example, 1, 2, 3, 4, 5, or 6 substituents located at any position.

By "$C_{1-6}$ alkyl" or "alkyl" is meant an optionally substituted $C_{1-6}$ saturated hydrocarbon group. An alkyl group may be linear, branched, or cyclic ("cycloalkyl"). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Substituted alkyl groups may have, for example, 1, 2, 3, 4, 5, or 6 substitutents located at any position. Exemplary substituted alkyl groups include, but are not limited to, optionally substituted $C_{1-4}$ alkaryl groups.

By "C$_{2-6}$ alkynyl" or "alkynyl" is meant an optionally substituted unsaturated C$_{2-6}$ hydrocarbon group having one or more carbon-carbon triple bonds. Exemplary C$_{2-6}$ alkynyl groups include, but are not limited to ethynyl, 1-propynyl, and the like By "amino" is meant a group having a structure —NR'R", where each R' and R" is selected, independently, from H, optionally substituted C$_{1-6}$ alkyl, optionally substituted cycloalkyl, optionally substituted heterocyclyl, optionally substituted aryl, optionally substituted heteroaryl, or R' and R" combine to form an optionally substituted heterocyclyl. When R' is not H or R" is not H, R' and R" may be unsubstituted or substituted with, for example, 1, 2, 3, 4, 5, or 6 substituents.

By "aryl" is meant is an optionally substituted C$_6$-C$_{14}$ cyclic group with [4n+2]π electrons in conjugation and where n is 1, 2, or 3. Non-limiting examples of aryls include heteroaryls and, for example, benzene, naphthalene, anthracene, and phenanthrene. Aryls also include bi- and tri-cyclic ring systems in which a non-aromatic saturated or partially unsaturated carbocyclic ring (e.g., a cycloalkyl or cycloalkenyl) is fused to an aromatic ring such as benzene or napthalene. Exemplary aryls fused to a non-aromatic ring include indanyl, tetrahydronaphthyl. Any aryls as defined herein may be unsubstituted or substituted. A substituted aryl may be optionally substituted with, for example, 1, 2, 3, 4, 5, or 6 substituents located at any position of the ring.

By "aryloxy" is meant a group having the structure —O(optionally substituted aryl), where aryl is as defined herein.

By "azido" is meant a group having the structure —N$_3$.

By "carbamate" or "carbamoyl" is meant a group having the structure —OCONR'R" or —NR'CO$_2$R", where each R' and R" is selected, independently, from H, optionally substituted C$_{1-6}$ alkyl, optionally substituted cycloalkyl, optionally substituted heterocyclyl, optionally substituted aryl, optionally substituted heteroaryl, or R' and R" combine to form an optionally substituted heterocyclyl. When R' is not H or R" is not H, R' and R" may be unsubstituted or substituted with, for example, 1, 2, 3, 4, 5, or 6 substituents.

By "carbonate" is meant a group having a the structure —OCO$_2$R', where R' is selected from H, optionally substituted C$_{1-6}$ alkyl, optionally substituted cycloalkyl, optionally substituted heterocyclyl, optionally substituted aryl, or optionally substituted heteroaryl. When R' is not H, R may be unsubstituted or substituted with, for example, 1, 2, 3, 4, 5, or 6 substituents.

By "carboxamido" or "amido" is meant a group having the structure —CONR'R" or —NR'C(=O)R", where each R' and R" is selected, independently, from H, optionally substituted C$_{1-6}$ alkyl, optionally substituted cycloalkyl, optionally substituted heterocyclyl, optionally substituted aryl, optionally substituted heteroaryl, or R' and R" combine to form an optionally substituted heterocyclyl. When R' is not H or R" is not H, R' and R" may be unsubstituted or substituted with, for example, 1, 2, 3, 4, 5, or 6 substituents.

By "carboxylic group" is meant a group having the structure —CO$_2$R', where R' is selected from H, optionally substituted C$_{1-6}$ alkyl, optionally substituted cycloalkyl, optionally substituted heterocyclyl, optionally substituted aryl, or optionally substituted heteroaryl. When R' is not H, R may be unsubstituted or substituted with, for example, 1, 2, 3, 4, 5, or 6 substituents.

By "cyano" is meant a group having the structure —CN.

By "C$_{3-10}$ cycloalkyl" or "cycloalkyl" is meant an optionally substituted, saturated or partially unsaturated 3- to 10-membered monocyclic or polycyclic (e.g., bicyclic, or tricyclic) hydrocarbon ring system. Where a cycloalkyl is polycyclic, the constituent cycloalkyl rings may be fused together, form a spirocyclic structure, or the polycyclic cycloalkyl may be a bridged cycloalkyl (e.g., adamantyl or norbonanyl). Exemplary cycloalkyls induce cyclopropyl, cyclobutyl, cyclopentyl, cyclohexyl, and cycloheptyl. Cycloalkyls may be unsubstituted or substituted. A substituted cycloalkyl can have, for example, 1, 2, 3, 4, 5, or 6 substituents.

By "cycloalkenyl" is meant a non-aromatic, optionally substituted 3- to 10-membered monocyclic or bicyclic hydrocarbon ring system having at least one carbon-carbon double bound. For example, a cycloalkenyl may have 1 or 2 carbon-carbon double bonds. Cycloalkenyls may be unsubstituted or substituted. A substituted cycloalkenyl can have, for example, 1, 2, 3, 4, 5, or 6 substituents. Exemplary cycloalkenyls include, but are not limited to, cyclopropenyl, cyclobutenyl, cyclopentenyl, cyclopentadienyl, cyclohexenyl, 1,3-cyclohexadienyl, 1,4-cyclohexadienyl, and the like.

By "effective amount" or "therapeutically effective amount" of an agent, as used herein, is that amount sufficient to effect beneficial or desired results, such as clinical results, and, as such, an effective amount depends upon the context in which it is being applied. For example, in the context of administering an agent that is an inhibitor of necroptosis, an effective amount of an agent is, for example, an amount sufficient to achieve a reduction in necroptosis as compared to the response obtained without administration of the agent.

By "ester" is meant a group having a structure selected from —OCOR', where R' is selected from H, optionally substituted C$_{1-6}$ alkyl, optionally substituted cycloalkyl, optionally substituted heterocyclyl, optionally substituted aryl, or optionally substituted heteroaryl. When R' is not H, R may be unsubstituted or substituted with, for example, 1, 2, 3, 4, 5, or 6 substituents.

By "halogen" or "halo" is meant fluorine (—F), chlorine (—Cl), bromine (—Br), or iodine (—I).

By "heteroaryl" is mean an aryl group that contains 1, 2, or 3 heteroatoms in the cyclic framework. Exemplary heteroaryls include, but are not limited to, furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, benzoxazole, isoxazole, isothiazole, pyrazole, thiazole, benzthiazole, triazole (e.g., 1,2,4-triazole or 1,2,3-triazole), benzotriazole, pyridines, pyrimidines, pyrazines, quinoline, isoquinoline, purine, pyrazine, pteridine, triazine (e.g, 1,2,3-triazine, 1,2,4-triazine, or 1,3,5-triazine)indoles, 1,2,4,5-tetrazine, benzo[b]thiophene, benzo[c]thiophene, benzofuran, isobenzofuran, and benzimidazole. Heteroaryls may be unsubstituted or substituted. Substituted heteroaryls can have, for example, 1, 2, 3, 4, 5, or 6 substitutents.

By "heterocyclic" or "heterocyclyl" is meant an optionally substituted non-aromatic, partially unsaturated or fully saturated, 3- to 10-membered ring system, which includes single rings of 3 to 8 atoms in size, and polycyclic ring systems (e.g., bi- and tri-cyclic ring systems) which may include an aryl (e.g., phenyl or naphthyl) or heteroaryl group that is fused to a non-aromatic ring (e.g., cycloalkyl, cycloalkenyl, or heterocyclyl), where the ring system contains at least one heterotom. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized or substituted. In certain embodiments, the term heterocylic refers to a non-aromatic 5-, 6-, or 7-membered monocyclic ring wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Where a heterocycle is polycyclic, the constituent rings may be fused together, form a spirocyclic structure, or the polycyclic heterocycle may be a bridged heterocycle (e.g., quinuclidyl or. Exemplary heterocyclics include, but are not limited to, aziridinyl, azetindinyl, 1,3-diazatidinyl, pyrrolidinyl, piperidinyl, piperazinyl, thiranyl, thietanyl, tetrahydrothiophenyl, dithiolanyl, tetrahydrothiopyranyl, oxiranyl, oxetanyl, tetrahydrofuranyl, tetrahydropyranyl, pyranonyl, 3,4-dihydro-2H-pyranyl, chromenyl, 2H-chromen-2-onyl, chromanyl, dioxanyl (e.g., 1,3-dioxanyl or 1,4-dioxanyl), 1,4-benzodioxanyl, oxazinyl, oxathiolanyl, morpholinyl, thiomorpholinyl, thioxanyl, quinuclidinyl, and also derivatives of said exemplary heterocyclics where the heterocyclic is fused to an aryl (e.g., a benzene ring) or a heteroaryl (e.g., a pyridine or pyrimidine) group. Any of the heterocyclic groups described herein may be unsubstituted or substituted. A substituted heterocycle may have, for example, 1, 2, 3, 4, 5, or 6 substituents.

By "ketone" or "acyl" is meant a group having the structure —COR', where R' is selected from H, optionally substituted $C_{1-6}$ alkyl, optionally substituted cycloalkyl, optionally substituted heterocyclyl, optionally substituted aryl, or optionally substituted heteroaryl. When R' is not II, R may be unsubstituted or substituted with, for example, 1, 2, 3, 4, 5, or 6 substituents.

By "nitro" is meant a group having the structure —$NO_2$.

A "pharmaceutically acceptable excipient" as used herein refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66:1-19. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvates," as used herein, refers to compounds that retain non-covalent associations to residual solvent molecules in the solid state. For example, solvates may be prepared by crystallization, recrystallization, or precipitation from a solution that includes organic solvents, water, or a mixture thereof. Solvates include, but are not limited to, compounds that include solvent molecules in the crystal lattice following recrystallization. The molecular stoichiometry of solvation can vary from, for example, 1:1 solvent:compound to 10:1 solvent:compound. These ratios can include a mixture of associated solvent molecules. Exemplary, non-limiting examples of solvents that can form solvates with the compounds of the invention include water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, or any combination thereof.

By "pharmaceutical composition" is meant a composition containing a compound of the invention, formulated with a pharmaceutically acceptable excipient, and manufactured or sold with the approval of a governmental regulatory agency as part of a therapeutic regimen for the treatment of disease in a mammal. Excipients consisting of DMSO are specifically excluded. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or any other formulation described herein.

By "stereoisomer" is meant a diastereomer, enantiomer, or epimer of a compound. A chiral center in a compound may have the S-configuration or the R-configuration. Enantiomers may also be described by the direction in which they rotate polarized light (i.e., (+) or (−)). Diastereomers of a compound include stereoisomers in which some, but not all, of the chiral centers have the opposite configuration as well as those compounds in which substituents are differently oriented in space (for example, trans versus cis).

Where a group is substituted, the group may be substituted with 1, 2, 3, 4, 5, or 6 substituents. Optional substituents include, but are not limited to: $C_{1-6}$ alkyl, $C_{2-6}$ alkenyl, $C_{2-6}$ alkynyl, cycloalkyl, cycloalkenyl, heterocyclyl, aryl, heteroaryl, halogen; azido(—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2H$), carboxylic ester (—$CO_2R'$), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, cycloalkyl, heterocyclyl, aryl, or heteroaryl. A substituted group may have, for example, 1, 2, 3, 4, 5, 6, 7, 8, or 9 substituents. In some embodiments, each hydrogen in a group may be replaced by a substituent group (e.g., perhaloalkyl groups such as —$CF_3$ or —$CF_2CF_3$ or perhaloaryls such as —$C_6F_5$). In other embodiments, a substitutent group may itself be further substituted by replacing a hydrogen of said substituent group with another substituent group such as those described herein. Substituents may be further substituted with, for example, 1, 2, 3, 4, 5, or 6 substituents as defined herein. For example, a lower $C_{1-6}$ alkyl or an aryl substituent group (e.g., heteroaryl, phenyl, or naphthyl) may be further substituted with 1, 2, 3, 4, 5, or 6 substituents as described herein.

DETAILED DESCRIPTION OF THE INVENTION

We have discovered a series of heterocyclic derivatives that inhibit tumor necrosis factor alpha (TNF-α)-induced necroptosis. The heterocyclic compounds of the invention include, for example, compounds of Formulas (I)-(VIII), or any pharmaceutically acceptable salt or solvate thereof, or any stereoisomer thereof, and are shown to inhibit TNF-α induced necroptosis in FADD-deficient variant of human Jurkat T cells. Still other useful necrostatins include Compounds (1)-(45). Compounds of the invention can be synthesized according to methods known in the art or by the methods provided in the examples below. Pharmaceutical compositions including the compounds of the invention are also described. The invention also features kits and methods of treatment featuring the compounds and compositions of the invention.

Compounds of Formula (I)

Certain compounds of the invention can be described by Formula (I):

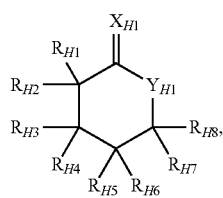

(I)

where each $X_{H1}$ and $X_{H2}$ is selected, independently, from O, S, or $NR_{H9}$;

$Y_{H1}$ is selected, independently, from O, S, or $NR_{H10}$;

each $R_{H1}$, $R_{H2}$, $R_{H3}$, $R_{H4}$, $R_{H5}$, $R_{H6}$, $R_{H7}$, and $R_{H8}$, is selected, independently, from H, halogen, cyano, nitro, azido, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted aryl, optionally substituted heterocyclyl, optionally substituted heteroaryl, —C(=O)$R_{H12}$, —C(=O)O$R_{H12}$, —C(=O)N$R_{H12}R_{H13}$, —C(=S)$R_{H12}$, —C(=S)N$R_{H12}R_{H13}$, —C(=N$R_{H14}$)$R_{H12}$, —C(=N$R_{H14}$)N$R_{H12}R_{H13}$, or —[$Z_{H1}$—(C$R_{H15}R_{H16}$)$_n$—{C(=$X_{H2}$)}$_o$—$Z_{H2}$—$R_{H17}$], or $R_{H1}$ and $R_{H3}$, or $R_{H5}$ and $R_{H7}$ combine to form a carbon-carbon double bond;

each $Z_{H1}$ and $Z_{H2}$ is selected, independently, from a single bond, O, S, or $NR_{H1}$ each $R_{H9}$, $R_{H10}$, $R_{H11}$, $R_{H12}$, $R_{H13}$, $R_{H14}$, $R_{H15}$, $R_{H16}$, and $R_{H17}$, is selected, independently from H, optionally substituted $C_{1-6}$ alkyl, optionally substituted $C_{3-10}$ cycloalkyl, optionally substituted aryl, optionally substituted heterocyclyl, or optionally substituted heteroaryl;

n is an integer between 0-6; and o is 0 or 1;

or any pharmaceutically acceptable salt or solvate thereof, or any stereoisomer thereof.

Certain compounds of the invention can be described by Formula (I-A):

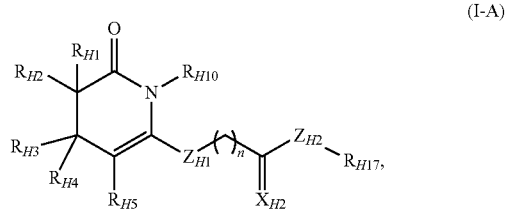

(I-A)

where each $R_{H1}$, $R_{H2}$, $R_{H3}$, $R_{H4}$, $R_{H5}$, $R_{H10}$, $R_{H17}$, $X_{H2}$, $Z_{H1}$, $Z_{H2}$, and n is as defined for Formula (I), or by Formula (I-B)

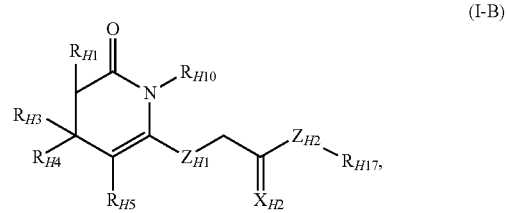

(I-B)

where each $R_{H1}$ and $R_{H3}$ is selected, independently, from H, halogen, cyano, nitro, azido, optionally substituted $C_{1-6}$ alkyl, optionally substituted $C_{3-10}$ cycloalkyl, optionally substituted aryl, optionally substituted heterocyclyl, optionally substituted heteroaryl, —C(=O)$R_{H12}$, —C(=O)O$R_{H12}$, or —C(=O)N$R_{H12}R_{H13}$, or $R_{H1}$ and $R_{H3}$ combine to form a carbon-carbon double bond;

each $R_{H4}$ and $R_{H17}$ is selected, independently, from optionally substituted aryl or optionally substituted heteroaryl;

$R_{H5}$ is selected from H, CN, —C(=O)O$R_{H12}$, or —C(=O)N$R_{H12}R_{H13}$;

each $R_{H10}$, $R_{H11}$, $R_{H12}$, and $R_{H13}$ is selected from H, optionally substituted $C_{1-6}$ alkyl, optionally substituted $C_{3-10}$ cycloalkyl, optionally substituted aryl, optionally substituted heterocyclyl, or optionally substituted heteroaryl;

$Z_{H1}$ is selected from a single bond or S;
$Z_{B2}$ is selected from a single bond or $NR_{H11}$; and
$X_{H2}$ is O or S;
or any pharmaceutically acceptable salt or solvate thereof, or any stereoisomer thereof.

In some embodiments of Formula (I), the compound has a structure according to the following formula:

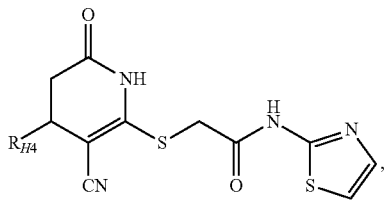

(I-C)

where $R_{H4}$ is as according to Formula (I-A) or (I-B).

In some embodiments of Formula (I), when $R_{H1}$ is H, $R_{H2}$ is H or $CO_2Me$, $R_{H3}$ is H, $R_{H4}$ is unsubstituted phenyl or phenyl substituted with 1, 2, or 3 substituents selected from methoxy, ethoxy, methyl, isopropyl, chloro, or fluoro, $R_{H5}$ is CN, $R_{H6}$ and $R_{H8}$ is H, $R_{H10}$ is H, $X_{H1}$ is O, $Y_{H1}$ is NH, and $R_{H7}$ is $-[S-(CH_2)-\{C(=O)\}_0-Z_{H2}-R_{17}]$, $Z_{H2}-R_{H17}$ is not $OCH_3$ or $NH-R_{H17}$, where $R_{H17}$ is H, unsubstituted 2-thiazolyl, unsubstituted phenyl, 4-methoxyphenyl, 4-fluorophenyl, or 2,4,6-trimethylphenyl.

Compounds of Formulas (I), (I-A), (I-B), and (I-C) can be prepared according to methods known in the art. An exemplary method of synthesis that can be used is shown in Scheme 1 and is based on protocols disclosed in *Russian Chemical Bulletin*, 48(12): 2308-2311 (1999) and in *Chemistry of Heterocyclic Compounds*, 38(10): 1269-1275 (2002). In Scheme 1, R' and R" can be, for example, an optionally substituted aryl or an optionally substituted heteroaryl group. Still other substituent patterns can be obtained by variation of the thioamide starting material that is condensed with the aldehyde.

Scheme 1

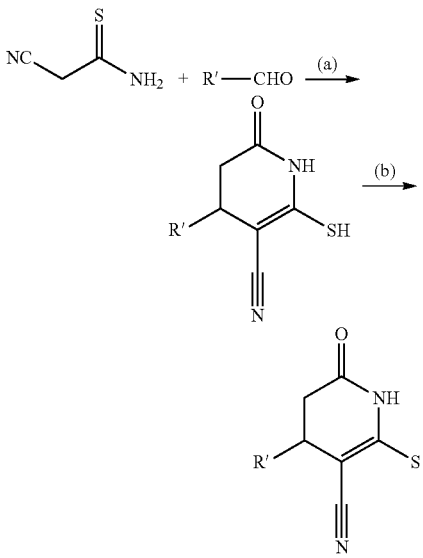

a) Meldrum's acid, N-Methylmorpholine, EtOH, rt, 12 h;
b) 2-Chloro-N-R''-acetamide, EtOH, $H_2O$, reflux, 2 min.

Compounds of Formula (I) (e.g., (I-A), (I-B), or (I-C)) or any pharmaceutically acceptable salt or solvate thereof, or any stereoisomer thereof, can also be used as described herein (e.g., in pharmaceutical compositions, as inhibitors of necroptosis, in methods of treatment, and in kits). Exemplary compounds useful in the methods, compositions, and kits of the invention, include but are not limited to those shown in Table 1. Other compounds of Formula I are shown in Table 2. In some embodiments, Formulas (I), (I-A), (I-B), or (I-C) do not include any of Compounds (1)-(12).

TABLE 1

| Compound | Structure |
| --- | --- |
| (1) | 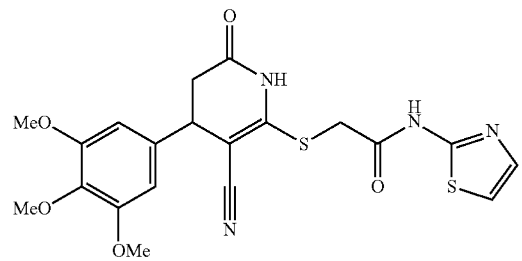 [SMILES: COc1cc(C2CC(=O)NC(SCC(=O)Nc3nccs3)=C2C#N)cc(OC)c1OC] |
| (2) | 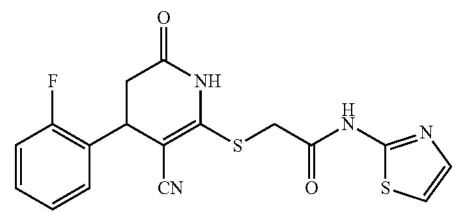 [SMILES: N#CC1=C(SCC(=O)Nc2nccs2)NC(=O)CC1c1ccccc1F] |
| (3) | 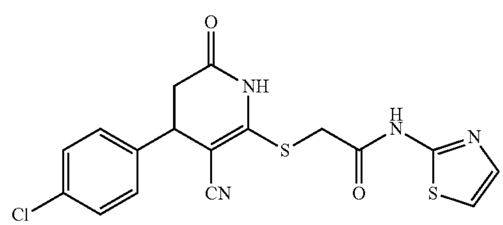 [SMILES: N#CC1=C(SCC(=O)Nc2nccs2)NC(=O)CC1c1ccc(Cl)cc1] |
| (4) | 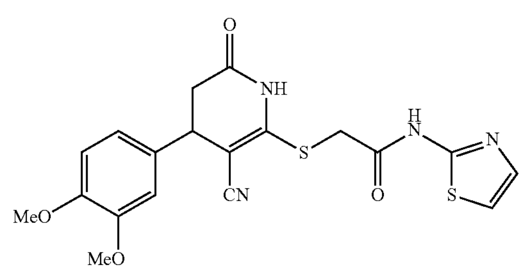 [SMILES: COc1ccc(C2CC(=O)NC(SCC(=O)Nc3nccs3)=C2C#N)cc1OC] |
| (5) | 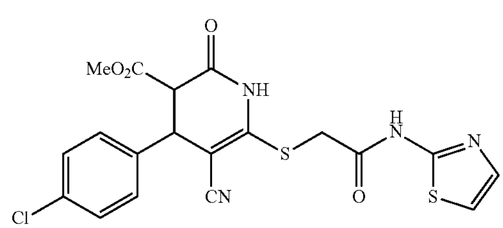 [SMILES: COC(=O)C1C(=O)NC(SCC(=O)Nc2nccs2)=C(C#N)C1c1ccc(Cl)cc1] |

TABLE 1-continued
| Compound | Structure |
|---|---|
| (6) | 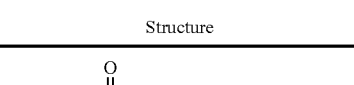 |
| (7) | |
TABLE 2
| Compound | Structure |
|---|---|
| (8) | 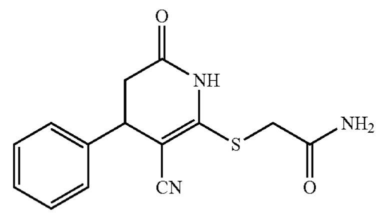 [SMILES: N#CC1=C(SCC(N)=O)NC(=O)CC1c1ccccc1] |
| (9) | 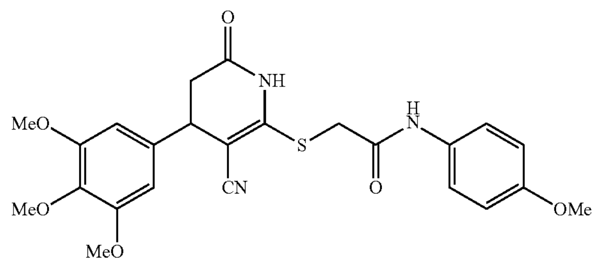 [SMILES: COc1ccc(NC(=O)CSC2=C(C#N)C(c3cc(OC)c(OC)c(OC)c3)CC(=O)N2)cc1] |
| (10) | 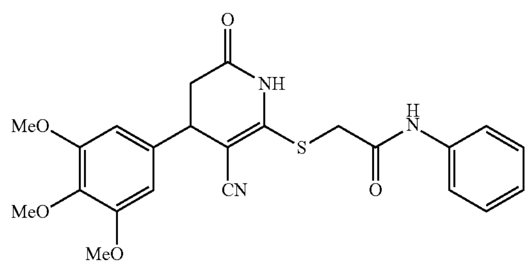 [SMILES: COc1cc(C2CC(=O)NC(SCC(=O)Nc3ccccc3)=C2C#N)cc(OC)c1OC] |
| (11) | 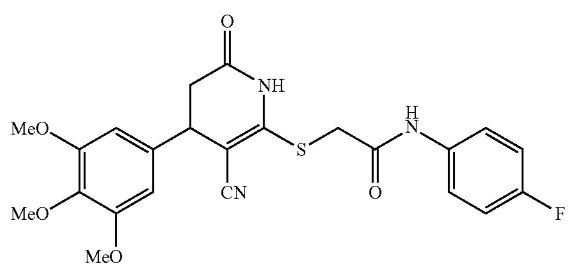 [SMILES: COc1cc(C2CC(=O)NC(SCC(=O)Nc3ccc(F)cc3)=C2C#N)cc(OC)c1OC] |
| (12) | 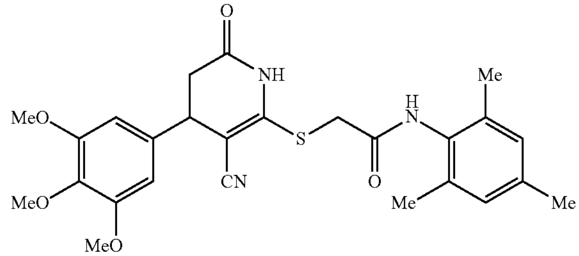 [SMILES: COc1cc(C2CC(=O)NC(SCC(=O)Nc3c(C)cc(C)cc3C)=C2C#N)cc(OC)c1OC] |

Compounds of Formula (II)

Select compounds of the invention can be described by Formula (II)

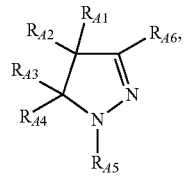

(II)

where each $R_{A1}$, $R_{A2}$, $R_{A3}$, $R_{A4}$, $R_{A5}$, and $R_{A6}$ is selected, independently, from H, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, optionally substituted heteroaryl, or a group having the structure —$X_{A1}$-$G_{A1}$-$X_{A2}$—C(=$Y_{A1}$)-$G_{A2}$-$X_{A3}$—$R_{A7}$, or $R_{A1}$ and $R_{A4}$ combine to form a carbon-carbon double bond;

each $X_{A1}$, $X_{A2}$, and $X_{A3}$ is, independently, absent or selected from —O—, —S—, or —$NR_{A8}$—;

$G_{A1}$ is absent or —$(CR_{A9}R_{A10})_m$—;

$G_{A2}$ is absent or —$(CR_{A11}R_{A12})_n$—;

$Y_{A1}$ is O, S, or $NR_{A13}$;

each $R_{A8}$ and $R_{A13}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl, —$COR_{A14}$, —$CO_2R_{A14}$, or —$CONR_{A14}R_{A15}$;

each $R_{A9}$, $R_{A10}$, $R_{A11}$, and $R_{A12}$ is selected, independently, from H, halogen, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl;

each $R_{A7}$, $R_{A14}$ and $R_{A15}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl; and each m and n is, independently, 1, 2, or 3;

or any pharmaceutically acceptable salt or solvate thereof, or any stereoisomer thereof.

In some embodiments of Formula (II), when $R_{A1}$ and $R_{A4}$ combine to form a carbon-carbon double bond, $R_{A2}$ is H, $R_{A3}$ is $CH_3$, and $R_{A6}$ is $CO_2H$, $R_{A5}$ is not $CH_2$(2-chlorophenyl).

In some embodiments of Formula (II), when $R_{A1}$ and $R_{A4}$ combine to form a carbon-carbon double bond, $R_{A2}$ is H, $R_{A6}$ is $CH_3$ or $^tBu$, and $R_{A3}$ is NHC(=O)$NHR_{A7}$, $R_{A7}$ is not chlorophenyl or dichlorophenyl.

Certain compounds of Formula (II) may be described further according to Formula (II-A)

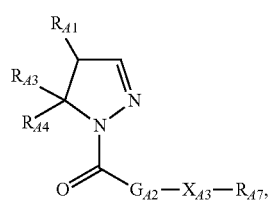

(II-A)

where each $R_{A1}$, $R_{A3}$, $R_{A4}$, and $R_{A7}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl, or $R_{A1}$ and $R_{A4}$ combine to form a carbon-carbon double bond;

$G_{A2}$ is absent or is —$(CR_{A11}R_{A12})_n$—;

$X_{A3}$ is absent or is O, S, or $NR_{A8}$;

each $R_{A11}$, $R_{A12}$, and $R_{A8}$ is selected, independently, from H or optionally substituted $C_{1-6}$ alkyl; and n is 1 or 2;

or according to Formula (II-B)

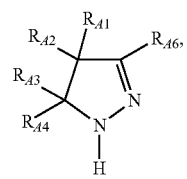

(II-B)

where $R_{A5}$ is H;

each $R_{A1}$, $R_{A2}$, $R_{A3}$, $R_{A4}$, and $R_{A6}$ is selected, independently, from H, optionally substituted aryl, optionally substituted heteroaryl, —C(=O)—$X_{A3}$—$R_{A7}$, or $R_{A1}$ and $R_{A4}$ combine to form a carbon-carbon double bond;

each $R_{A7}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl; and each $X_{A3}$ is, independently, absent, —O—, or —$NR_{A8}$—, or any pharmaceutically acceptable salt or solvate thereof or any stereoisomer thereof.

In some embodiments of Formula (II) (e.g., (II-A) and (II-B)), when one of $R_{A1}$ and $R_{A4}$ is H and the other is selected from H or $CO_2Et$, and $R_{A3}$ is unsubstituted phenyl, $G_{A2}$-$X_{A3}$—$R_{A7}$ is not $NHC_6H_5$, $NH(p-C_6H_4F)$, $NH(p-C_6H_4OH)$, $NH(p-C_6H_4OMe)$, $NH(3-OH-4-C_1-C_6H_4)$, —$CH_2(O-p-C_6H_4Me)$, —$CH_2$(4-ethylpiperazinyl), —$CH_2S$ (2-phenyltetrazolyl), —$CH_2S$(4-chlorophenyl), —$CH_2S$(2-benzothiazolyl), —$CH_2S$(2-(N-methylimidazolyl)), —$CH_2S$(4,6-dimethylquinazolinyl), adamantyl, or optionally substituted oxiranyl.

Other compounds of Formula (II) include compounds of Formula (II-C):

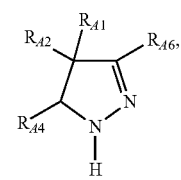

(II-C)

where each $R_{A1}$, $R_{A2}$, $R_{A4}$, and $R_{A6}$ is selected, independently, from H, —C(=O)—$X_{A3}$—$R_{A7}$, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl, or $R_{A1}$ and $R_{A4}$ combine to form a carbon-carbon double bond;

each $X_{A3}$ is, independently, absent, —O—, or —$NR_{A8}$—, each $R_{A8}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl, —$COR_{A14}$, —$CO_2R_{A14}$, or —$CONR_{A14}R_{A15}$; and each $R_{A7}$, $R_{A14}$ and $R_{A15}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl.

In some embodiments of Formula (II-C), wherein when $R_{A1}$ and $R_{A4}$ combine to form a carbon-carbon double bond and $R_{A2}$ is H, $R_{A6}$ is not 4-chlorophenyl, 4-methoxyphenyl, or 4-(NHCO$_2^t$Bu)phenyl. In other embodiments, when $R_{A1}$ is H, $R_{A4}$ is H or CO$_2$Et, $R_{A2}$ is unsubstituted phenyl, $R_{A6}$ is not —C(=O)-(unsubstituted phenyl) or —C(=O)-(4-methylphenyl). In still other embodiments, when $R_{A1}$ is H, $R_{A4}$ is —C(=O)-(unsubstituted phenyl), $R_{A2}$ is 4-chlorophenyl, $R_{A6}$ is not CO$_2$Et.

Compounds of Formula (II) (e.g., (II-A)-(II-C)) can be prepared according to methods known in the art. Exemplary methods of synthesis are shown in Schemes 2-5.

Scheme 2

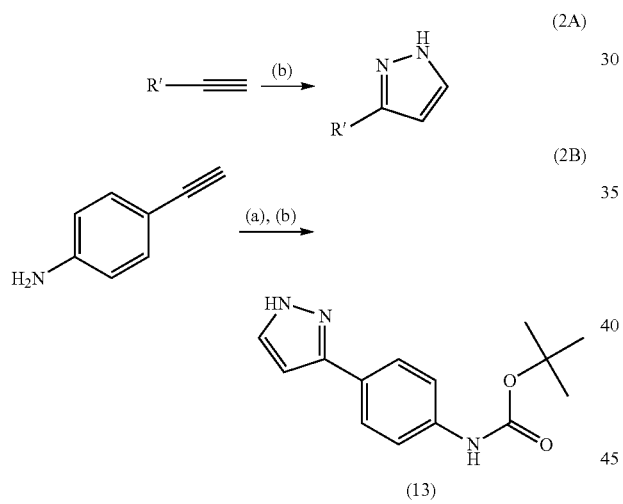

a) Boc$_2$O, THF, 3 h, reflux; b) trimethylsilyl diazomethane, DMF, 100° C., 60 h.

Scheme 2A shows a method that can be used to prepare pyrazole compounds of Formula (II). Terminal alkynes can be reacted with trimethylsilyldiazomethane (TMS-diazomethane) to afford compounds of Formula (II) where $R_{A1}$ and $R_{A4}$ combine to form a carbon-carbon double bond and R' can be, for example, optionally substituted aryl or optionally substituted heteroaryl. Scheme 2B shows the preparation of Compound (13) using the method in Scheme 2A in which the aniline —NH$_2$ group is protected prior to the reaction with TMS-diazomethane.

Scheme 3

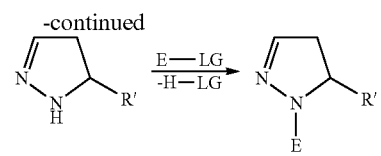

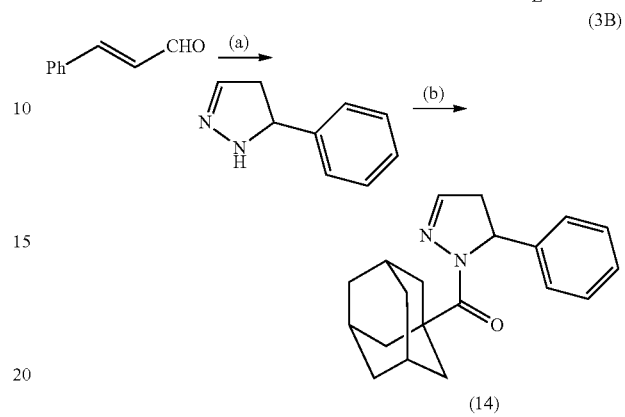
a) N$_2$H$_4$, EtOH; b) 1-Adamantane carbonyl chloride, heat, 5 min.

Scheme 3A depicts another method that can be used to synthesize pyrazoline compounds of Formula (II) according to methods described in *J. Chem. Soc.* 4686-90 (1952) and *J. Med. Chem.* 2127-2137 (2006). For example, substituted acroleins (e.g., R' can be optionally substituted aryl or optionally substituted heteroaryl) can be treated with ethanolic hydrazine (Step (a)) to afford a pyrazoline intermediate. The pyrazoline can then be treated with an electrophilic compound having a suitable leaving group (e.g., alkyl halides, acid cholorides. or acid anhydrides) and an optional chemical promoter to afford N-substituted pyrazolines. Scheme 3B shows a method that can be used to prepare Compound (14) where an acid chloride can be used in Step (b) as shown.

Scheme 4

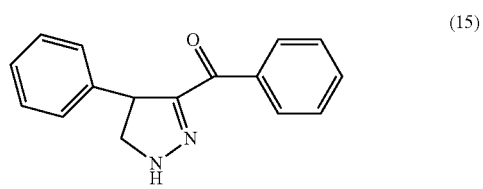

Scheme 4 shows Compound (15) which can be prepared according to the procedure described in *J. Am. Chem. Soc.*, page 165 (1943). This method can also be used to prepare other pyrazoline compounds of Formula (II), where $R_{A6}$ is —C(=O)—$R_{A7}$ and $R_{A2}$ and $R_{A7}$ are, independently, optionally substituted aryl or optionally substituted heteroaryl.

Scheme 5

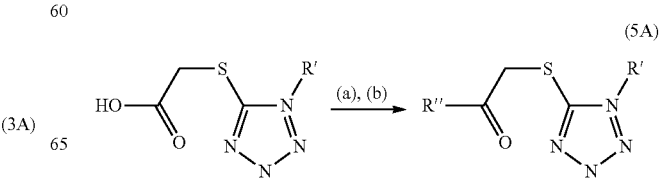

-continued (5B)

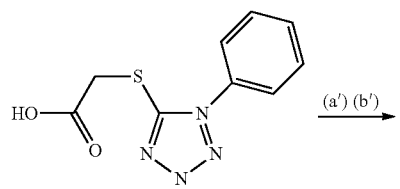

a) PCl$_5$, CHCl$_3$, Toluene, 3.5 h; b) R″, 70° C.

Scheme 5A depicts a method by which tetrazole compounds of Formula (II) can be prepared using methods described in WO2005115147 and in *J. Med. Chem.*, 4686-90 (1952). For example, a tetrazole compound that includes a carboxylic acid group can be activated (e.g., treatment with PCl$_5$ as in Step (a)) and subsequently treated with a nucleophile R″ as in Step (b). Scheme 5B shows that 5-Phenyl-4,5-dihydro-1H-pyrazole can be used as the nucleophile in step (b′) to afford Compound (16).

Compounds of Formula (II) (e.g., (II-A) and (II-B) and compounds (13)-(16)), or any pharmaceutically acceptable salt or solvate thereof, or any stereoisomer thereof, can also be used as described herein (e.g., in pharmaceutical compositions, as inhibitors of necroptosis, in methods of treatment, and in kits). Additional exemplary compounds useful in, for example, the methods, compositions, and kits of the invention, include but are not limited to those shown in Table 3. Other compounds of Formula (II) are shown in Table 4. In some embodiments, Formula (II), (II-A), and (II-B) do not include any of compounds (13)-(26).

TABLE 3

| Compound | Structure |
|---|---|
| (17) | 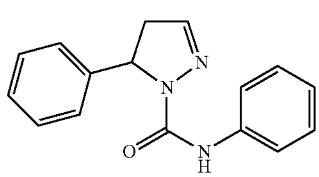 [SMILES: O=C(Nc1ccccc1)N1N=CCC1c1ccccc1] |
| (18) | 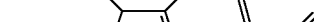 |

TABLE 3-continued

| Compound | Structure |
|---|---|
| (19) | 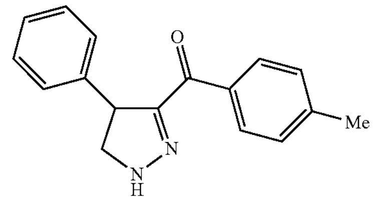 [SMILES: Cc1ccc(C(=O)C2=NNCC2c2ccccc2)cc1] |
| (20) | 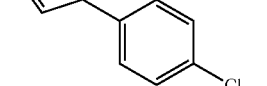 |
| (21) | 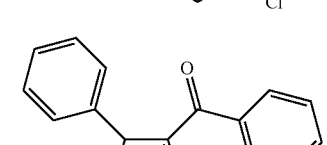 |

TABLE 4

| Compound | Structure |
|---|---|
| (22) | 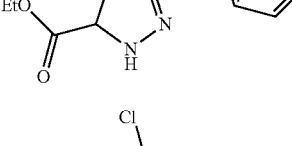 |
| (23) | 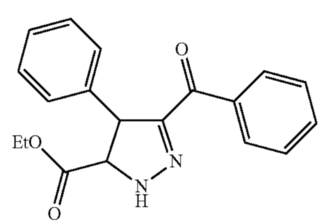 [SMILES: CCOC(=O)C1NN=C(C(=O)c2ccccc2)C1c1ccccc1] |
| (24) | 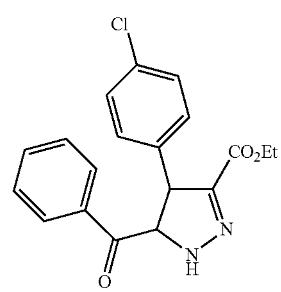 [SMILES: CCOC(=O)C1=NNC(C(=O)c2ccccc2)C1c1ccc(Cl)cc1] |

TABLE 4-continued

| Compound | Structure |
|---|---|
| (25) | 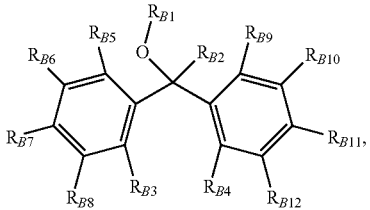 |
| (26) | 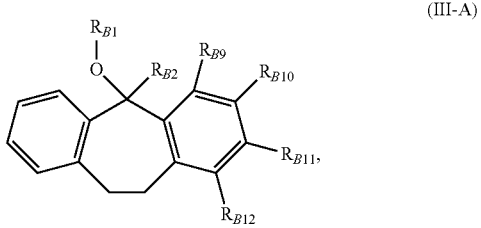 |

Compounds of Formula (III)

Select compounds of the invention can be described by Formula (III)

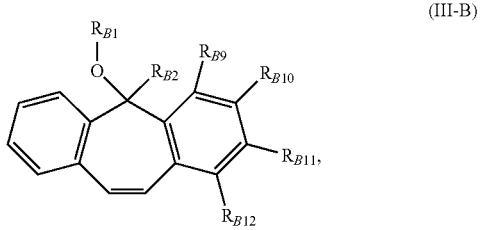

(III)

where $R_{B1}$ is selected from H, optionally substituted $C_{1-6}$ alkyl, —C(═O)$R_{B18}$, —C(═O)O$R_{B18}$, or —C(═O)N$R_{B18}R_{B19}$;

$R_{B2}$ is selected from H, optionally substituted $C_{1-6}$ alkyl, optionally substituted $C_{2-6}$ alkenyl, or optionally substituted $C_{2-6}$ alkynyl;

each $R_{B3}$ and $R_{B4}$ is selected, independently from H, optionally substituted $C_{1-6}$ alkyl, or $R_{B3}$ and $R_{B4}$ combine to form a bridging group having the structure —(CH$_2$)$_n$—(CR$_{B13}$═CR$_{B14}$)$_o$—(CH$_2$)$_p$—;

each n, o, and p is, independently, 0 or 1;

each $R_{B5}$, $R_{B6}$, $R_{B7}$, $R_{B8}$, $R_{B9}$, $R_{B10}$, $R_{B11}$, and $R_{B12}$ is selected, independently, from H, halogen, —CN, —NO$_2$, —N$_3$, —$R_{B13}$, —O$R_{B13}$, —S$R_{B13}$, —N$R_{B13}R_{B14}$, —C(═O)$R_{B15}$, —C(═O)O$R_{B15}$, —C(═O)N$R_{B15}R_{B16}$, —OC(═O)$R_{B15}$, —OC(═O)O$R_{B15}$, —OC(═O)N$R_{B15}R_{B16}$, —N$R_{B15}$C(═O)$R_{B15}$, —N$R_{B15}$C(═O)O$R_{B16}$, —N$R_{B15}$C(═O)N$R_{B16}R_{B17}$, —C(═S)$R_{B15}$, —C(═S)N$R_{B15}R_{B16}$, —N$R_{B15}$C(═S)$R_{B16}$, —N$R_{B15}$C(═S)N$R_{B16}R_{B17}$, —C(═N$R_{B13}$)N$R_{B15}R_{B16}$, —N$R_{B15}$C(═N$R_{B13}$)$R_{B16}$, —N$R_{B15}$C(═N$R_{B13}$)N$R_{B16}R_{B17}$;

each $R_{B13}$ and $R_{B14}$ is selected, independently, from H, optionally substituted $C_{1-6}$ alkyl, optionally substituted $C_{3-10}$ cycloalkyl, optionally substituted aryl, optionally substituted heteroaryl, —C(═O)$R_{B18}$, —C(═O)O$R_{B18}$, or —C(═O)N$R_{B18}R_{B19}$;

each $R_{B15}$, $R_{B16}$, $R_{B17}$, $R_{B18}$, and $R_{B19}$ is selected, independently, from H, optionally substituted $C_{1-6}$ alkyl, optionally substituted $C_{3-10}$ cycloalkyl, optionally substituted aryl, or optionally substituted heteroaryl; and where when each n, o, and p is 0, $R_{B3}$ and $R_{B4}$ combine to form a single bond, or any pharmaceutically acceptable salt or solvate thereof, or any stereoisomer thereof.

Select compounds of Formula (III) can also be described by Formula (III-A)

(III-A)

where $R_{B1}$ is as described in Formula (III), $R_{B2}$ is ethyl, ethenyl, or ethynyl and each $R_{B9}$, $R_{B10}$, $R_{B11}$, and $R_{B12}$ is selected, independently, from H and halogen, or any pharmaceutically acceptable salt or solvate thereof, or any stereoisomer thereof.

In some embodiments, $R_{B1}$ is H.

Still other compounds of Formula (III) are described by Formula (III-B)

(III-B)

where $R_{B1}$ is as described in Formula (III), $R_{B2}$ is ethyl, ethenyl, or ethynyl and each $R_{B9}$, $R_{H10}$, $R_{B11}$, and $R_{B12}$ is selected, independently, from H and halogen, or any pharmaceutically acceptable salt or solvate thereof, or any stereoisomer thereof.

In some embodiments, $R_{B1}$ is H.

In some embodiments of Formula (III), $R_{B1}$ is not H or CH$_3$ when $R_{B5}$, $R_{B6}$, $R_{B7}$, $R_{B8}$, $R_{B9}$, $R_{B10}$, $R_{B11}$, and $R_{B12}$ are each H, $R_{B2}$ is ethyl, ethenyl, ethynyl, propynyl, 2-haloethynyl, —(C≡CC(—OH)(CH$_3$)$_2$), and when $R_{B3}$ and $R_{B4}$ are each H or combine to form a bond, —CH$_2$CH$_7$— or —CH═CH—. In other embodiments of Formula (III), $R_{B1}$ is not H when $R_{B5}$, $R_{B6}$, $R_{B7}$, $R_{B8}$, $R_{B10}$, and $R_{B11}$ are each H, at least one of $R_{B9}$ or $R_{B12}$ is fluoro, $R_{B7}$ is ethynyl, and when $R_{B3}$ and $R_{B4}$ combine to form —CH$_7$CH$_2$—. In still other embodiments of Formula (III), $R_{B1}$ is not H when $R_{B6}$, $R_{B7}$, $R_{B8}$, $R_{B10}$, and $R_{B11}$ are H and one or two of $R_{B6}$, $R_{B8}$, $R_{B10}$, and $R_{B12}$ is halogen, nitro, or methyl.

Scheme 6

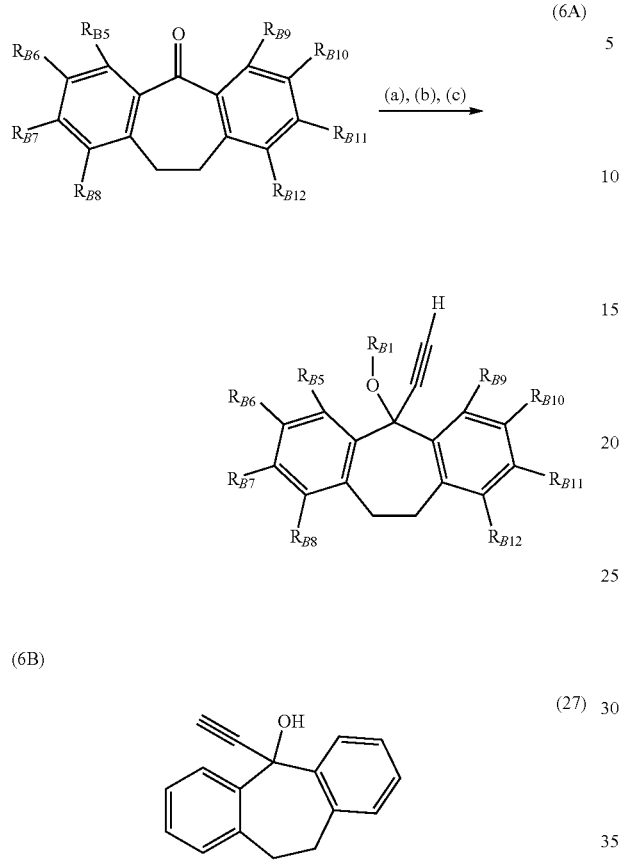

(a) n-BuLi/Trimethylsilylacetylene, THF, 0° C; THF, rt then reflux;
(b) quench with H' or electrophile R$_{B1}$—X; (c) 0.1M NaOH, MeOH, rt, 6 h.

Scheme 6A depicts a method by which compounds of Formula (III) can be prepared. A ketone derivative can be treated with an anionic carbon nucleophile (e.g., lithium trimethylsilylacetylide formed in step (a)). The resulting alkoxide can be trapped using a protic quench or by the addition of an electrophilic reagent. Finally, the trimethylsilyl group can be deprotected using basic conditions. If desired, the alkyne group can be further manipulated (e.g., subjected to hydrogenation conditions to afford the corresponding alkene or alkyl group or treated with a metal catalyst/and organic electrophile in cross-coupling reactions). Scheme 6B shows Compound (27), which can be prepared using these conditions.

Compounds of Formula (III) (e.g., (III-A) and (III-B) and compound (27)), or any pharmaceutically acceptable salt or solvate thereof, or any stereoisomer thereof, can also be used as described herein (e.g., in pharmaceutical compositions, as inhibitors of necroptosis, in methods of treatment, and in kits). Additional exemplary compounds useful in, for example, the methods, compositions, and kits of the invention, include but are not limited to those shown in Table 5. Other compounds of Formula (III) include Compounds (35)-(36), (39)-(40), and (42)-(47) shown in Table 6. In some embodiments, Formula (III) does not include any of Compounds (27)-(33), (35)-(36), (39)-(40), or (42)-(47).

TABLE 5

| Compound | Structure |
|---|---|
| (28) | 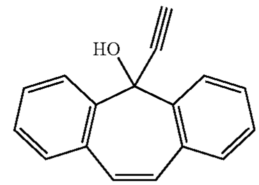 [SMILES: C#CC1(O)c2ccccc2C=Cc2ccccc21] |
| (29) | 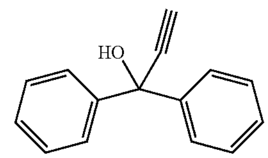 [SMILES: C#CC(O)(c1ccccc1)c1ccccc1] |
| (30) | 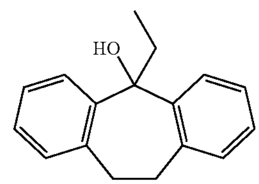 [SMILES: CCC1(O)c2ccccc2CCc2ccccc21] |
| (31) | 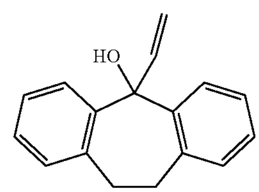 [SMILES: C=CC1(O)c2ccccc2CCc2ccccc21] |
| (32) | 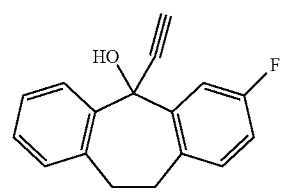 [SMILES: C#CC1(O)c2ccccc2CCc2ccc(F)cc21] |
| (33) | 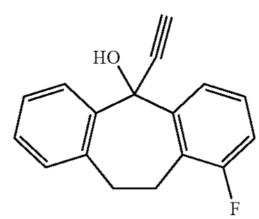 [SMILES: C#CC1(O)c2ccccc2CCc2c(F)cccc21] |

TABLE 6

| Compound | Structure |
|---|---|
| (34) | 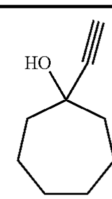 |

TABLE 6-continued
| Compound | Structure |
|---|---|
| (35) | 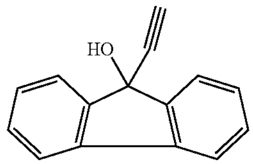 [SMILES: C#CC1(O)c2ccccc2-c2ccccc21] |
| (36) | 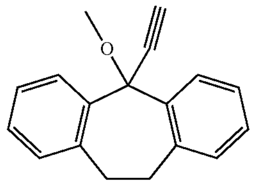 [SMILES: C#CC1(OC)c2ccccc2CCc2ccccc21] |
| (37) | 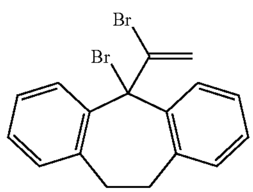 [SMILES: C=C(Br)C1(Br)c2ccccc2CCc2ccccc21] |
| (38) | 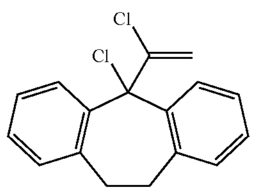 [SMILES: C=C(Cl)C1(Cl)c2ccccc2CCc2ccccc21] |
| (39) | 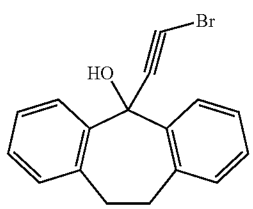 [SMILES: OC1(C#CBr)c2ccccc2CCc2ccccc21] |
| (40) | 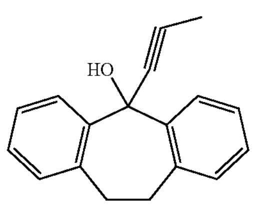 [SMILES: CC#CC1(O)c2ccccc2CCc2ccccc21] |
| (41) | 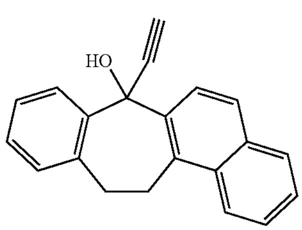 [SMILES: C#CC1(O)c2ccccc2CCc2c1ccc1ccccc21] |
| (42) | 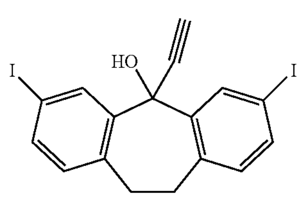 [SMILES: C#CC1(O)c2cc(I)ccc2CCc2ccc(I)cc21] |
| (43) | |
| (44) | |
| (45) | |
| (46) | |
| (47) | |
Compounds of Formula (IV)
Still other compounds can be described according to Formula (IV)
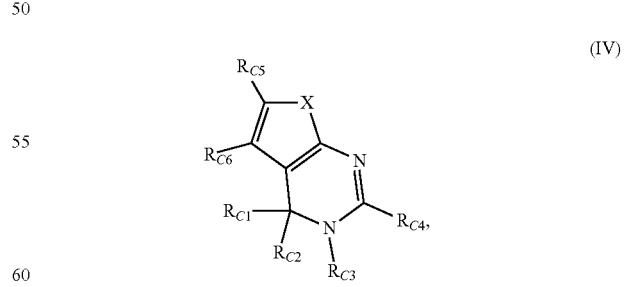
(IV)
where
each $R_{C1}$, $R_{C2}$, and $R_{C3}$ is selected, independently, from H, optionally substituted $C_{1-6}$ alkyl, —Y—$R_{C7}$, or $R_{C1}$ and $R_{C2}$ combine to form a (=O) or a (=S) group, or $R_{C1}$ and $R_{C3}$ combine to form a carbon-nitrogen double bond;

R$_{C4}$ is selected from H, halogen, —CN, optionally substituted C$_{1-6}$ alkyl, optionally substituted C$_{3-10}$ cycloalkyl, optionally substituted heterocyclyl, optionally substituted aryl, optionally substituted heteroaryl, or —C(=O)ZR$_{C8}$, each R$_{C5}$ and R$_{C6}$ is selected, independently, from H, optionally substituted C$_{1-6}$ alkyl, or R$_{C1}$ and R$_{C2}$ combine to form an optionally substituted C$_{3-10}$ cycloalkyl, optionally substituted heterocyclyl, optionally substituted aryl, or optionally substituted heteroaryl;

each R$_{C7}$, R$_{C8}$, R$_{C9}$, R$_{C10}$, R$_{C11}$, and R$_{C12}$ is selected, independently, from H, optionally substituted C$_{1-6}$ alkyl, optionally substituted C$_{3-10}$ cycloalkyl, optionally substituted heterocyclyl, optionally substituted aryl, or optionally substituted heteroaryl;

X is —CR$_{C11}$=CR$_{C12}$—, O, S, or NR$_{C9}$;

Y is, independently, a single bond, (CR$_{C8}$R$_{C9}$)$_n$, O, S, or NR$_{C10}$;

Z is a single bond, O, S, or NR$_{C10}$;

or any pharmaceutically acceptable salt or solvate thereof, or any stereoisomer thereof.

In some embodiments of Formula (IV), when X is S, R$_{C1}$ and R$_{C2}$ combine to form a (=O) group, R$_{C4}$ is H, and R$_{C5}$ and R$_{C6}$ combine to form unsubstituted cyclopentyl, R$_{C3}$ is not —CH$_2$—R$_{C7}$, where R$_{C7}$ is unsubstituted phenyl, unsubstituted naphthyl, unsubstituted 8-quinolyl, unsubstituted 2-oxoquinolyl, or phenyl having 1 or 2 substituents selected from F, OMe, Me, CN, or Cl. In other embodiments of Formula (IV), when X is S, R$_{C1}$ and R$_{C2}$ combine to form a (=O) group, R$_{C4}$ is H, and R$_{C5}$ and R$_{C6}$ are each Me, R$_{C3}$ is not —CH$_2$—R$_{C7}$, where R$_{C7}$ is unsubstituted phenyl. In other embodiments of Formula (IV), when X is CH=CH, R$_{C1}$ and R$_{C2}$ combine to form a (=O) group, R$_{e4}$, R$_{C5}$ and R$_{C6}$ are H, R$_{C3}$ is not —CH$_2$(4-halophenyl).

Select compounds of Formula (IV) can also be described by Formula (IV-A)

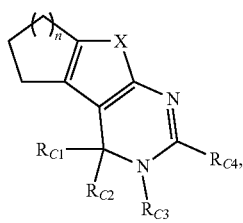

(IV-A)

where X, R$_{C1}$, R$_{C2}$, R$_{C3}$, and R$_{C4}$ are as defined for Formula (IV) and n is an integer between 0-3, or any pharmaceutically acceptable salt or solvate thereof, or any stereoisomer thereof.

Scheme 7

(7A)

(7B)

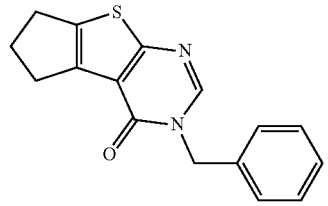

(48)

a) NaH, electrophile, THF, 0° C.

Scheme 7A depicts a method by which compounds of Formula (IV) (e.g., compounds of Formula (IV-A)) can be prepared. A heterocyclic derivative can be deprotonated using a base such as NaH and subsequently treated with an electrophile (e.g., an alkyl halide such as benzyl bromide, an acid chloride, or an acid anhydride) to afford a compound of Formula (IV) such as Compound (48) shown in Scheme 7B.

Compounds of Formula (IV) (e.g., (IV-A) and Compound (48)), or any pharmaceutically acceptable salt or solvate thereof, or any stereoisomer thereof, can also be used as described herein (e.g., in pharmaceutical compositions, as inhibitors of necroptosis, in methods of treatment, and in kits). Additional exemplary compounds useful in, for example, the methods, compositions, and kits of the invention, include but are not limited to those shown in Table 7. In some embodiments, Formula (IV) does not include any of Compounds (48)-(57).

TABLE 7

| Compound | Structure |
| --- | --- |
| (49) | 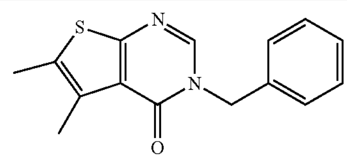 [SMILES: Cc1sc2ncn(Cc3ccccc3)c(=O)c2c1C] |
| (50) | 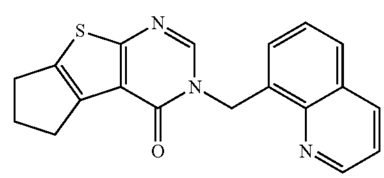 [SMILES: O=c1c2c3c(sc2ncn1Cc1cccc2cccnc12)CCC3] |
| (51) | 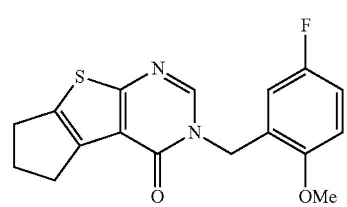 [SMILES: COc1ccc(F)cc1Cn1cnc2sc3c(c2c1=O)CCC3] |
| (52) | 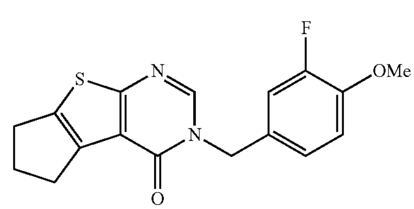 [SMILES: COc1ccc(Cn2cnc3sc4c(c3c2=O)CCC4)cc1F] |

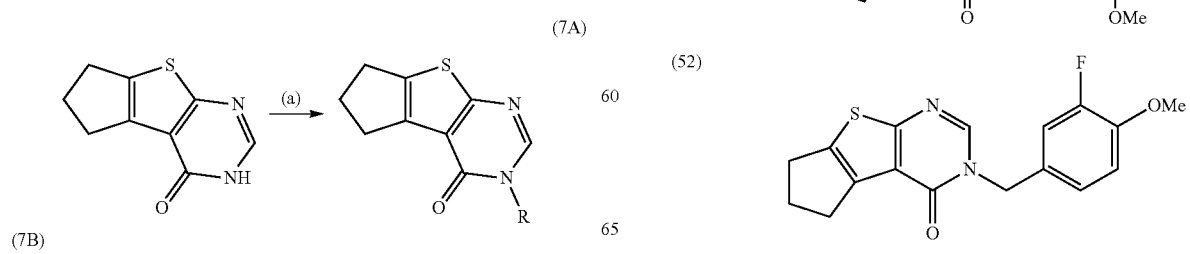

TABLE 7-continued

| Compound | Structure |
|---|---|
| (53) | 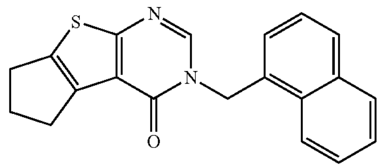 [SMILES: O=c1c2c3c(sc2ncn1Cc1cccc2ccccc12)CCC3] |
| (54) | 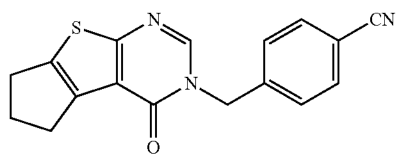 [SMILES: N#Cc1ccc(Cn2cnc3sc4c(c3c2=O)CCC4)cc1] |
| (55) | 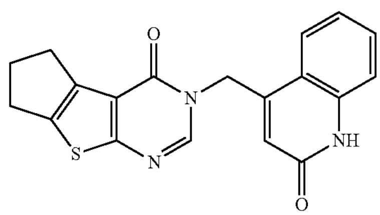 [SMILES: O=c1cc(Cn2cnc3sc4c(c3c2=O)CCC4)c2ccccc2[nH]1] |
| (56) | 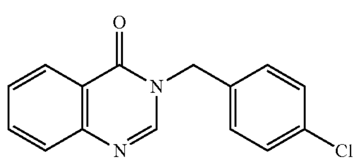 [SMILES: O=c1c2ccccc2ncn1Cc1ccc(Cl)cc1] |
| (57) | 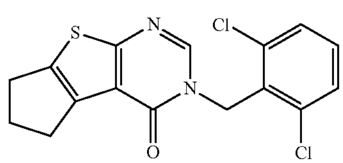 [SMILES: O=c1c2c3c(sc2ncn1Cc1c(Cl)cccc1Cl)CCC3] |

Compounds of Formula (V)

Other compounds of the invention can be described by Formula (V)

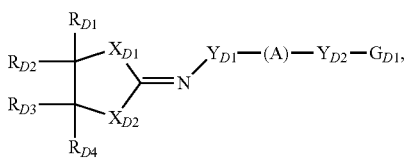
(V)

where each $X_{D1}$ and $X_{D2}$ is selected, independently, from O, S, $NR_{D5}$, or $CR_{D6}R_{D7}$;

$Y_{D1}$ is selected from a covalent bond, —C(=O)—, —S(=O)—, or —S(=O)$_2$—;

$Y_{D2}$ is selected from a covalent bond, —C(=O)—, —OC(=O)—, —NR$_{D8}$C(=O)—, —S(=O)—, —S(=O)$_2$—, —OS(=O)—, —OS(=O)$_2$—, —NR$_{D8}$S(=O)—, —NR$_{D8}$S(=O)$_2$—, or —C(=S)—;

A is selected from optionally substituted aryl or optionally substituted heteroaryl;

$G_{D1}$ is selected from H, optionally substituted $C_{1-6}$ alkyl, optionally substituted $C_{3-10}$ cycloalkyl, optionally substituted heterocyclyl, optionally substituted aryl, optionally substituted heteroaryl, $OR_{D9}$, or $NR_{D9}R_{D10}$;

each $R_{D1}$, $R_{D2}$, $R_{D3}$, $R_{D4}$, $R_{D6}$, $R_{D7}$, is selected, independently, from H, halogen, CN, NC, N$_3$, NO$_2$, $OR_{D11}$, $SR_{D11}$, $NR_{D11}R_{D12}$, —COR$_{D13}$, —CO$_2$R$_{D13}$, —CONR$_{D13}$R$_{D14}$, optionally substituted $C_{1-6}$ alkyl, optionally substituted $C_{3-10}$ cycloalkyl, optionally substituted heterocyclyl, optionally substituted aryl, or optionally substituted heteroaryl, or $R_{D1}$ and $R_{D4}$, or $R_{D1}$ and $R_{D5}$, or $R_{D1}$ and $R_{D6}$, or $R_{D3}$ and $R_{D5}$, or $R_{D3}$ and $R_{D6}$ combine to form a double bond;

each $R_{D5}$, $R_{D8}$, $R_{D9}$, $R_{D10}$, $R_{D13}$, $R_{D14}$, $R_{D15}$, and $R_{D16}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl, or $R_{D9}$ and $R_{D10}$ combine to form a heterocyclyl;

each $R_{D11}$ and $R_{D12}$ is selected, independently, from H, optionally substituted $C_{1-6}$ alkyl, optionally substituted $C_{3-10}$ cycloalkyl, optionally substituted heterocyclyl, optionally substituted aryl, optionally substituted heteroaryl, —COR$_{D15}$—CO$_2$R$_{D15}$, —CONR$_{D15}$R$_{D16}$, —S(=O)R$_{D15}$, —S(O)OR$_{D15}$, —S(=O)NR$_{D15}$R$_{D16}$, —S(=O)$_2$R$_{D15}$, —S(=O)$_2$OR$_{D15}$, —S(=O)$_2$NR$_{D15}$R$_{D16}$;

where $Y_{D1}$ and $Y_{D2}$ are each covalently bound to a carbon center in A;

or any pharmaceutically acceptable salt or solvate thereof, or any stereoisomer thereof.

Still other compounds of Formula (V) can be described by Formula (V-A)

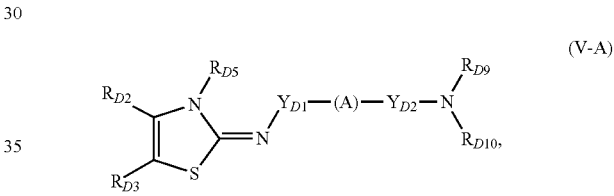
(V-A)

where each $Y_{D1}$ and $Y_{D2}$ is selected, independently, from —C(=O)— or —S(=O)$_2$—;

A is phenyl having 0, 1, 2, 3, or 4 additional substituents;

$R_{D2}$ and $R_{D3}$ are selected, independently from H, halogen, CN, NC, N$_3$, NO$_2$, —COR$_{D13}$, —CO$_2$R$_{D13}$, —CONR$_{D13}$R$_{D14}$, optionally substituted $C_{1-6}$ alkyl, optionally substituted $C_{3-10}$ cycloalkyl, optionally substituted heterocyclyl, optionally substituted aryl, or optionally substituted heteroaryl;

each $R_{D5}$, $R_{D9}$, $R_{D10}$, $R_{D13}$, and $R_{D14}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl, or $R_{D9}$ and $R_{D10}$ combine to form a heterocyclyl; or by Formula (V-B)

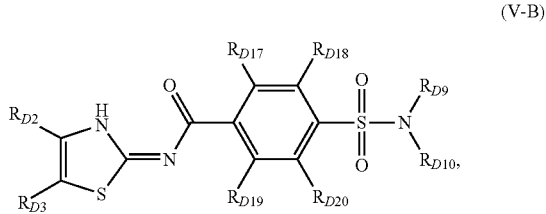
(V-B)

where each $R_{D2}$, $R_{D3}$, $R_{D17}$, $R_{D18}$, $R_{D19}$, and $R_{D20}$ is selected, independently from H, halogen, CN, NC, $N_3$, $NO_2$, —$COR_{D13}$, —$CO_2R_{D13}$, —$CONR_{D13}R_{D14}$, optionally substituted $C_{1-6}$ alkyl, optionally substituted aryl, or optionally substituted heteroaryl; and each $R_{D9}$ and $R_{D10}$ is selected, independently, from H, optionally substituted $C_{1-6}$ alkyl, optionally substituted $C_{3-10}$ cycloalkyl, or optionally substituted aryl, or $R_{D9}$ and $R_{D10}$ combine to form a heterocyclyl; or any pharmaceutically acceptable salt or solvate thereof, or any stereoisomer thereof.

In some embodiments of Formula (V), when $R_{D1}$ and $R_{D4}$ combine to form a double bond, $R_{D2}$ and $R_{D3}$ are H, $X_{D1}$ is NH, $X_{D2}$ is S, $Y_{D1}$ is —(C=O)—, $Y_{D2}$ is —(SO$_2$)—, $G_{D1}$ is —N(Et)$_2$, and A is phenyl having no additional substituents, $Y_{D1}$ and $Y_{D2}$ are not para to each other.

Scheme 8

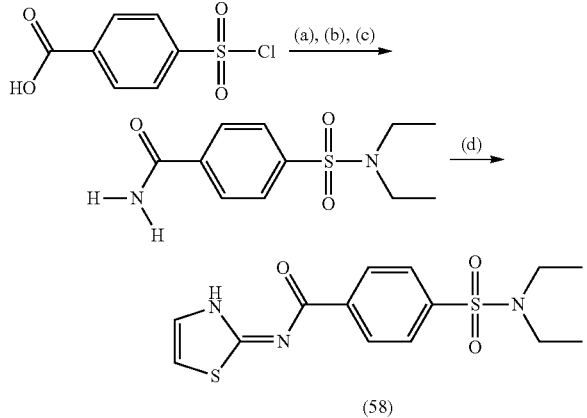

(58)

(a) Et$_2$NH, NaOH, H$_2$O, 3. 5 h then acidify; (b) H$_2$SO$_4$, MeOH, reflux; (c) NH$_3$ in MeOH. rt; (d) 3H-Thiazol-2-one, TiCl$_4$, Et$_2$O, Hexane, -30° C.

Compounds of Formula (V) (e.g., compounds of Formula (V-A) or (V-B)) can be prepared, for example, by treating an aryl or heteroaryl compound that has two electrophilic groups successively with nucleophilic reagents to afford the desired compound. For example, as shown in Scheme 8 and using procedures adapted from *Heterocyclic Communications*, 12(6): 453-456 (2006) and Organic *Synthesis, Collective Vol.* 6, page 818, the difunctional benzene derivative 4-CO$_2$Hphenylsulfonyl chloride can be treated with a nucleophile such as diethylamine to afford the corresponding sulfonamide. This compound can then be esterified prior to treatment with a second nucleophile (e.g., methanolic ammonia). Finally, the compound afforded by step (c) can then be condensed with a carbonyl-containing compound to afford compounds of Formula (V) such as Compound (58).

Compounds of Formula (V) (e.g., (V-A) and (V-B) and compound (34)), or any pharmaceutically acceptable salt or solvate thereof, or any stereoisomer thereof, can also be used as described herein (e.g., in pharmaceutical compositions, as inhibitors of necroptosis, in methods of treatment, and in kits). In some embodiments, Formulas (V), (V-A), and (V-B) do not include Compounds (58).

Compounds of Formula (VI)

Still other compounds of the invention can be described by Formula (VI)

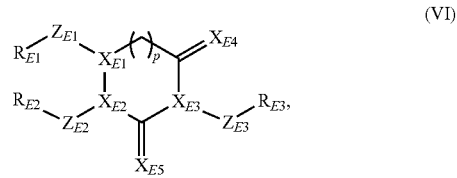

where each $X_{E1}$ and $X_{E3}$ is selected, independently, from N or $CR_{E4}$;

each $X_{E4}$ and $X_{E5}$ is selected, independently, from O, S, or $NR_{E5}$;

$X_{E2}$ is selected from O, S, or N;

each $Z_{E1}$, $Z_{E2}$, and $Z_{E3}$ is selected, independently, from a single bond, —(CR$_{E6}$R$_{E7}$)$_n$—, —C(=O)—, or —S(=O)$_2$—, or $Z_{E1}$—$R_{E1}$ and $Z_{E2}$—$R_{E2}$ combine to form a double bond;

each $R_{E1}$, $R_{E2}$, $R_{E3}$, $R_{E4}$, $R_{E5}$, $R_{E6}$, and $R_{E7}$ is selected, independently, from H, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl;

p is 0 or 1; and n is an integer between 1-6; and where when $X_{E2}$ is O or S, $Z_{E2}$—$R_{E2}$ is not present;

or any pharmaceutically acceptable salt or solvate thereof, or any stereoisomer thereof.

In some embodiments, each $R_{E1}$, $R_{E2}$, $R_{E3}$, $R_{E4}$, $R_{E5}$, $R_{E6}$, and $R_{E7}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl In some embodiments, $R_{E3}$ is selected from substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl.

In some embodiments of Formula (VI), when p is 0, $X_{E1}$ is CH, —$Z_{E1}$—$R_{E1}$ is —CH$_2$(indol-3-yl), $X_{E4}$ and $X_{E5}$ are 0, and $X_{E2}$—$Z_{E2}$—$R_{E2}$ is NH, $X_{E3}$—$Z_{E3}$—$R_{E3}$ is not —NCH$_2$(p-ClC$_6$H$_4$) or —NCH$_2$CH$_2$O(p-FC$_6$H$_4$).

In other embodiments, when $X_{E1}$—$Z_{E1}$—$R_{E1}$ is NH, $X_{E2}$—$Z_{E2}$ is CH—CH$_2$, $R_{E2}$ is unsubstituted 3-indolyl, p is 0, $X_{E4}$ is S, $X_{E5}$ is O, $X_{E3}$ is N, and $Z_{E3}$ is CH$_2$, $R_{E3}$ is not —CH$_2$CH$_2$(4-morpholine).

In still other embodiments, when $X_{E1}$—$Z_{H}$—$R_{E1}$ is NH, $X_{E2}$—$Z_{E2}$ is CH—CH$_2$, $R_{E2}$ is unsubstituted or substituted 3-indolyl, p is 0 or 1, both $X_{E4}$ and $X_{E5}$ are O or $X_{E4}$ is S and $X_{E5}$ is O, $X_{E3}$ is N, and $Z_{E3}$ is CH$_2$, $R_{E3}$ is not H, unsubstituted $C_{1-6}$ alkyl, or —CH$_2$CH=CH$_2$.

In any of the compounds of Formula (VI) described herein (e.g., any compound having a structure according to Formulas (VI), (VI-A), (VI-B), (VI-C), or (VI-D)), the $R_{E3}$ group can be unsubstituted. In some embodiments, a substituted $R_{E3}$ group includes 1, 2, 3, 4, or 5 substituents selected from, for example, $C_{1-6}$ alkyl, $C_{2-6}$ alkenyl, $C_{2-6}$ alkynyl, cycloalkyl, cycloalkenyl, heterocyclyl, aryl, heteroaryl, azido(—N$_3$), alkoxy (—OR'), amido (—NR'C(=O)R" or —C(=O)NRR'), amino (—NRR'), carbamoyl (—OC (=O)NR'R" or —NRC(=O)OR'), hydroxy (—OH), or isocyano (—NC), where each R or R' is selected, independently, from H, $C_{1-6}$ alkyl, $C_{2-6}$ alkenyl, $C_{2-6}$ alkynyl, cycloalkyl, heterocyclyl, aryl, or heteroaryl. In other embodiments, the substituted $R_{E3}$ group includes 1, 2, 3, or 4 substituents that are electron donating groups (e.g., hydroxy, $C_{1-6}$ alkoxy, $C_{1-6}$ alkyl, and amino groups).

Certain compounds of Formula (VI) may be described by Formula (VI-A) or Formula (VI-B)

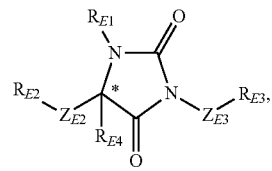

(VI-A)

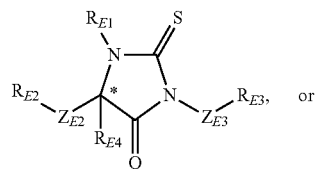

(VI-B-1)

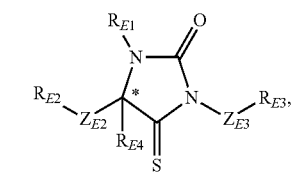

(VI-B-2)

wherein each $Z_{E2}$ and $Z_{E3}$ is selected, independently, from a single bond, —(CR$_{E6}$R$_{E7}$)$_n$—, —C(=O)—, or $R_{E1}$ and $Z_{E2}$—$R_{E2}$ combine to form a double bond;

each $R_{E1}$, $R_{E2}$, $R_{E3}$, and $R_{E4}$ is selected, independently, from H, optionally substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl;

each $R_{E6}$ and $R_{E7}$ is selected, independently, from H or optionally substituted $C_{1-6}$ alkyl; and n is an integer between 1-6;

or any pharmaceutically acceptable salt or solvate thereof, or any stereoisomer thereof.

In some embodiments, each $R_{E1}$, $R_{E2}$, $R_{E3}$, and $R_{E4}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl.

In some embodiments, $R_{E3}$ is selected from substituted $C_{1-6}$ alkyl, optionally substituted $C_{2-6}$ alkenyl, optionally substituted $C_{2-6}$ alkynyl, optionally substituted $C_{3-10}$ cycloalkyl, optionally substituted heterocyclyl, optionally substituted aryl, or optionally substituted heteroaryl.

In some embodiments of Formula (VI-A), when $R_{E1}$ and $R_{E4}$ are H, $Z_{E2}$ and $Z_{E3}$ are each $CH_2$, and $R_{E2}$ is unsubstituted 3-indolyl, $R_{E3}$ is not 4-chlorophenyl.

In certain embodiments, the compounds of Formula (VI) are described by the following formula:

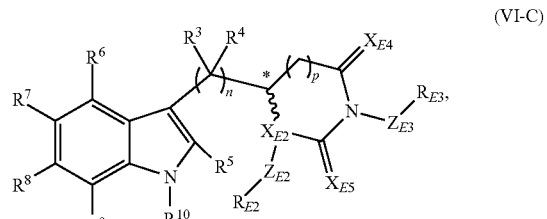

(VI-C)

where each $X_{E4}$ and $X_{E5}$ is, independently, O or S;

$X_{E2}$ is O or N;

each $Z_{E2}$ and $Z_{E3}$ is selected, independently, from a single bond or —(CR$_{E6}$R$_{E7}$)$_n$—;

each $R_{E2}$ and $R_{E3}$ is, independently, H, optionally substituted $C_{1-6}$ alkyl, optionally substituted $C_{3-10}$ cycloalkyl, optionally substituted $C_{2-6}$ alkenyl, optionally substituted $C_{2-6}$ alkynyl, optionally substituted aryl, optionally substituted heterocyclyl, or optionally substituted heteroaryl;

each $R^3$ and $R^4$ is, independently, H, halogen, or optionally substituted $C_{1-6}$ alkyl;

each $R^5$, $R^6$, $R^7$, $R^8$, and $R^9$ is selected, independently, from H, halogen, CN, $NO_2$, $OR^{13}$, $NR^{13}R^{14}$, $COR^{15}$, $CO_2R^{15}$, optionally substituted $C_{1-6}$ alkyl, or optionally substituted aryl;

$R^{10}$ is selected from H, halogen, CN, $NO_2$, $OR^{13}$, $NR^{13}R^{14}$, $COR^{15}$, $CO_2R^{15}$, optionally substituted $C_{1-6}$ alkyl, optionally substituted aryl, optionally substituted alkenyl, or optionally substituted alkynyl;

each $R^{13}$ and $R^{14}$ is selected, independently, from H, $COR^{16}$, $CO_2R^{16}$, optionally substituted $C_{1-6}$ alkyl, optionally substituted $C_{3-10}$ cycloalkyl, optionally substituted heterocyclyl, optionally substituted aryl, or optionally substituted heteroaryl; and each $R^{11}$, $R^{12}$, $R^{15}$, and $R^{16}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl; and where, independently, n is 0, 1, 2, 3, 4, or 5, and p is 0 or 1;

or any pharmaceutically acceptable salt or solvate thereof, or stereoisomer thereof.

In some embodiments, p is 0.

In some embodiments, $R_{E3}$ is selected from substituted $C_{1-6}$ alkyl, optionally substituted $C_{3-10}$ cycloalkyl, optionally substituted $C_{2-6}$ alkenyl, optionally substituted $C_{2-6}$ alkynyl, optionally substituted aryl, optionally substituted heterocyclyl, or optionally substituted heteroaryl.

Select compounds of Formula (VI-C) can also be described by Formula (VI-D):

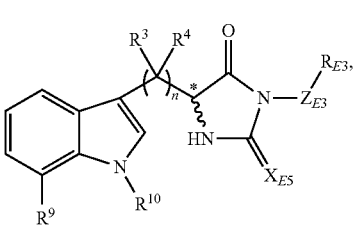

(VI-D)

where $X_{E5}$ is O or S;

—$Z_{E3}$—$R_{E3}$ is optionally substituted $C_{1-4}$ alkaryl;

each $R^3$, $R^4$, and $R^{10}$ is, independently, H or optionally substituted $C_{1-6}$ alkyl;

$R^9$ is H, halogen, CN, $NO_2$, $OR^{13}$, $NR^{13}R^{14}$, $COR^{15}$, $CO_2R^{15}$, or optionally substituted $C_{1-6}$ alkyl;

each $R^{13}$ and $R^{14}$ is selected, independently, from H, $COR^{16}$, $CO_2R^{16}$, optionally substituted $C_{1-6}$ alkyl, optionally substituted $C_{3-10}$ cycloalkyl, optionally substituted heterocyclyl, optionally substituted aryl, or optionally substituted heteroaryl; and each $R^{11}$, $R^{12}$, $R^{15}$, and $R^{16}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl; and where n is 1 or 2;

or any pharmaceutically acceptable salt or solvate thereof, or stereoisomer thereof.

In some embodiments, the compound has a structure according to the following formula:

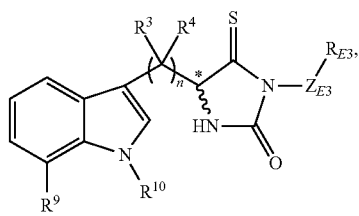

(VI-E)

or any pharmaceutically acceptable salt or solvate thereof, or stereoisomer thereof, where n, $Z_{E3}$, $R_{E3}$, $R^3$, $R^4$, $R^9$, and $R^{10}$ are as defined for Formula (IV-D).

In the compounds of the invention, the sp³-hybridized carbon to which G is attached (e.g., the chiral center marked with an asterisk in any of Formulas (VI-A), (VI-B-1), (VI-B-2), (VI-C), (VI-D), or (VI-E)) can have the (R)- or the (S)-configuration. For example, compounds of the invention include

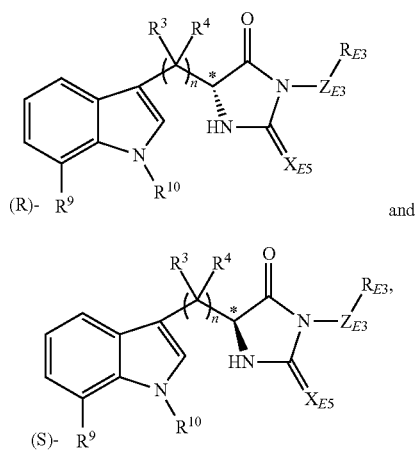

or any pharmaceutically acceptable salt or solvate thereof.

In any embodiment of Formulas (VI-C), (VI-D), or (VI-E), n=1 and $R^3$ and $R^4$ are each H. In another embodiment, $R^{10}$ is H or $CH_3$. In still other embodiments, $R^9$ is H, halogen, optionally substituted $C_{1-6}$ alkyl, OH, or —O-(optionally substituted $C_{1-6}$ alkyl).

In any embodiment of Formulas (VI-C), (VI-D), or (VI-E), —$Z_{E3}$—$R_{E3}$ is optionally substituted benzyl. In one embodiment, —$Z_{E3}$—$R_{E3}$ is unsubstituted benzyl. In another embodiment, —$Z_{E3}$—$R_{E3}$ is benzyl having 1, 2, 3, 4, or 5 substituents. In some embodiments, the substituents are selected from the group consisting of $C_{1-6}$ alkyl, $C_{2-6}$ alkenyl, $C_{2-6}$ alkynyl, cycloalkyl, cycloalkenyl, heterocyclyl, aryl, heteroaryl, azido(—$N_3$), alkoxy (—OR'), amido (—NR'C(=O)R" or —C(=O)NRR'), amino (—NRR'), carbamoyl (—OC(=O)NR'R" or —NRC(=O)OR'), hydroxy (—OH), and isocyano (—NC), as described herein. In a further embodiment, —$Z_{E3}$—$R_{E3}$ is $CH_2$— (p-$XC_6H_4$), where X is halogen. In some embodiments, X is F or Cl.

In any of the embodiments described herein, one or both of —$Z_{E3}$ and $R_{E3}$ do not include substituents selected from the group consisting of: halogen (e.g., F, Cl, Br, or I); nitro (—$NO_2$), cyano (—CN), acyloxy(—OC(=O)R'), acyl (—C(=O)R'), carboxylic acid (—$CO_2H$), carboxylic ester (—$CO_2R'$), sulfonate (—$S(=O)_2OR$), sulfonamide (—$S(=O)_2NRR'$ or —$NRS(=O)_2R'$), or sulfonyl (—$S(=O)_2R$), where each R or R' is selected, independently, from H, $C_{1-6}$ alkyl, $C_{2-6}$ alkenyl, $C_{2-6}$ alkynyl, cycloalkyl, heterocyclyl, aryl, or heteroaryl, as described herein.

Scheme 9

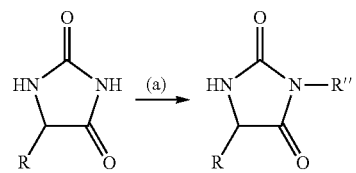

(9A)

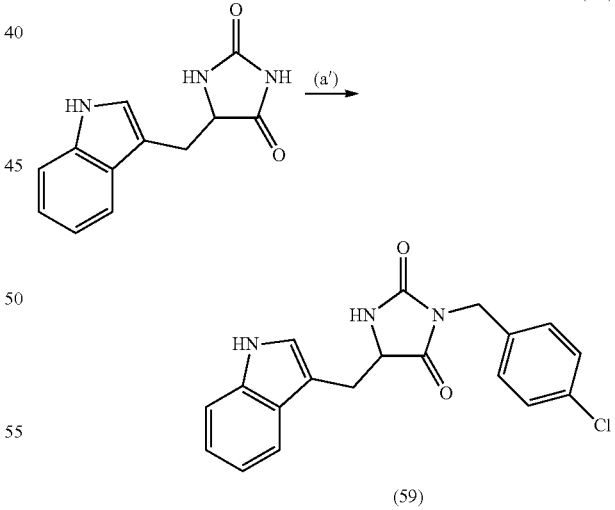

(9B)

(59)

(a) electrophile R"—X, KOH, EtOH, $H_2O$, 100° C, 12 h;

(a') electrophile = 4-chlorobenzylbromide

Compounds of Formula (VI) (e.g., compounds of Formulas (VI-A), (VI-B), (VI-C), or (VI-D)) can be prepared, for example, by treating hydantoin compound that has, for example, a substituent R at the 5-position with a base followed by trapping with an electrophilic reagent (Scheme 9A). For example, Scheme 9B shows that the synthesis of Compound (59) can be achieved by the use of 4-chlorobenzylbromide as the electrophile.

In some embodiments, Formula (VI) (e.g., compounds of Formulas (VI-A), (VI-B), (VI-C), or (VI-D)) does not include any of the compounds or formulas disclosed in U.S. Pat. Nos. 6,756,394 and 7,253,201, in U.S. Patent Publication No. 20050119260, and in pending U.S. application Ser. Nos. 12/077,320 and 12/086,792, each of which is hereby incorporated by reference.

Compounds of Formula (VI) (e.g., (VI-A)-(VI-D) and compound (59)), or any pharmaceutically acceptable salt or solvate thereof, or any stereoisomer thereof, can also be used as described herein (e.g., in pharmaceutical compositions, as inhibitors of necroptosis, in methods of treatment, and in kits).

In some embodiments, Formula (VI) does not include compound (59).

Compounds of Formula (VII)

Still other compounds can be described according to Formula (VII)

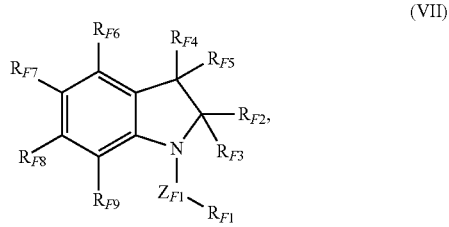

(VII)

where $Z_{F1}$ is selected from a single bond, —$(CR_{F10}R_{F11})_n$—, —C(=O)—, —S(=O)—, or —S(=O)$_2$—;

each $R_{F1}$, $R_{F2}$, $R_{F4}$, $R_{F10}$, $R_{F11}$, $R_{F12}$, and $R_{F13}$, is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl, or $R_{F2}$ and $R_{F4}$ combine to form a carbon-carbon double bond;

each $R_{F3}$ and $R_{F5}$ is selected, independently, from H, halogen, CN, $CO_2R_{F12}$, optionally substituted $C_{1-6}$ alkyl, optionally substituted $C_{3-10}$ cycloalkyl, optionally substituted heterocyclyl, optionally substituted aryl, or optionally substituted heteroaryl;

each $R_{F6}$, $R_{F7}$, $R_{F8}$, and $R_{F9}$ is selected, independently, from H, halogen, CN, NC, $N_3$, $NO_2$, $OR_{F12}$, $SR_{F12}$, $NR_{F12}R_{F13}$, —$COR_{F12}$, —$CO_2$ $_{F12}$, —$CONR_{F12}R_{F13}$, optionally substituted $C_{1-6}$ alkyl, optionally substituted $C_{3-10}$ cycloalkyl, optionally substituted heterocyclyl, optionally substituted aryl, or optionally substituted heteroaryl; and where n is an integer between 1-6;

or any pharmaceutically acceptable salt or solvate thereof, or any stereoisomer thereof.

Certain compounds of Formula (VII) can also be described by Formula (VII-A)

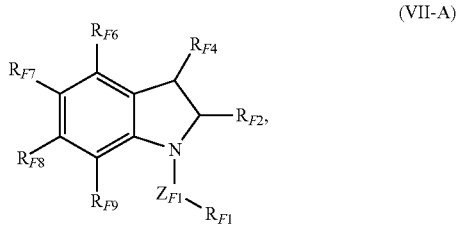

(VII-A)

where $Z_{F1}$ is selected from a single bond, —$(CH_2)$—, —C(=O)—, or —S(=O)$_2$—;

$R_{F1}$ is selected from H, optionally substituted $C_{3-10}$ cycloalkyl, optionally substituted heterocyclyl, optionally substituted aryl, or optionally substituted heteroaryl;

$R_{F2}$ and $R_{F4}$ are each H, or $R_{F2}$ and $R_{F4}$ combine to form a carbon-carbon double bond;

each $R_{F6}$, $R_{F7}$, $R_{F8}$, and $R_{F9}$ is selected, independently, from H, halogen, CN, NC, $N_3$, $NO_2$, $OR_{F12}$, $SR_{F12}$, $NR_{F12}R_{F13}$, —$COR_{F12}$, —$CO_2$ $_{F12}$, —$CONR_{F12}R_{F13}$, optionally substituted $C_{1-6}$ alkyl, optionally substituted $C_{3-10}$ cycloalkyl, optionally substituted heterocyclyl, optionally substituted aryl, or optionally substituted heteroaryl; and each $R_{F12}$ and $R_{F13}$, is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl;

or any pharmaceutically acceptable salt or solvate thereof, or any stereoisomer thereof.

In some embodiments of Formula (VII-A), when $R_{F2}$, $R_{F4}$, $R_{F6}$, $R_{F7}$, $R_{F8}$, and $R_{F9}$ are each H and $Z_{F1}$ is —C(=O)—, $R_{F1}$ is not -(unsubstituted 1,4-benzodioxane) or —$CH_2$—(O-(unsubstituted phenyl)).

Scheme 10

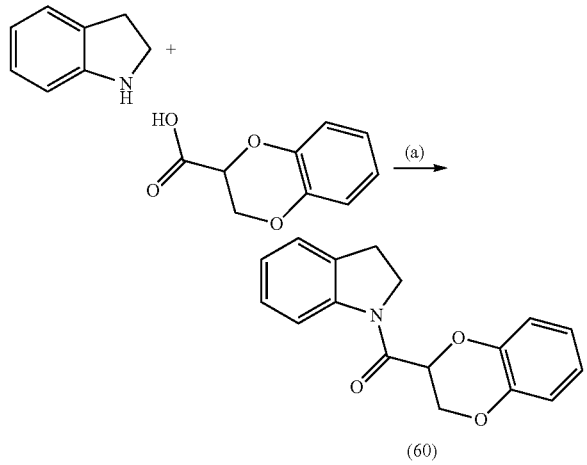

(60)

(a) Diethyl azodicarboxylate (DEAD), PPh$_3$, THF, rt.

Scheme 10 provides a method by which compounds of Formula (VII) such as Compound (60) can be prepared. For example, a nucleophilic compound such as indoline can be treated with an electrophile (e.g., a compound containing a carboxylic acid) in the presence of an optional promoter such as DEAD/PPh$_3$ to afford the requisite compound. Another compound of Formula (VIII) is Compound (61) (Scheme 11).

Scheme 11

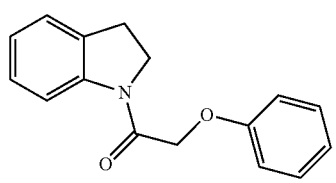

(61)

Compounds of Formula (VII) (e.g., (VII-A) and compound (60)), or any pharmaceutically acceptable salt or solvate thereof, or any stereoisomer thereof, can also be used as described herein (e.g., in pharmaceutical compositions, as inhibitors of necroptosis, in methods of treatment, and in kits). In some embodiments, Formulas (VII) and (VII-A) do not include compounds (60) or (61).

Compounds of Formula (VIII)

Still other compounds useful in the invention are described by Formula (VIII):

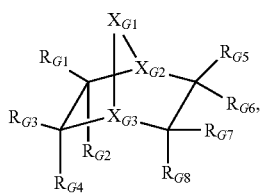
(VIII)

where $X_{G1}$ is selected from —O—, —N—, or —$(CR_{G9}R_{G10})_n$—;

$X_{G2}$ and $X_{G3}$ are selected, independently, from N or $CR_{G11}$;

each $R_{G1}$, $R_{G2}$, $R_{G3}$, $R_{G4}$, $R_{G5}$, $R_{G6}$, $R_{G7}$, $R_{G8}$, $R_{G9}$, $R_{G10}$, and $R_{G11}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl, or $R_{G1}$ and $R_{G2}$, or $R_{G3}$ and $R_{G4}$, or $R_{G5}$ and $R_{G6}$, or $R_{G7}$ and $R_{G8}$ combine to form an optionally substituted cycloalkyl or heterocyclyl; and n is 1 or 2;

or any pharmaceutically acceptable salt or solvate thereof, or any stereoisomer thereof.

Select compounds of Formula (VIII) can also be described by Formula (VIII-A):

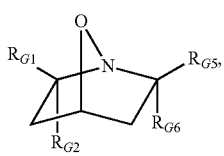
(VIII-A)

wherein each $R_{G1}$, $R_{G2}$, $R_{G5}$, and $R_{G6}$ is selected, independently, from H, optionally substituted $C_{1-6}$ alkyl, optionally substituted $C_{3-10}$ cycloalkyl, optionally substituted heterocyclyl, optionally substituted aryl, or optionally substituted heteroaryl, or $R_{G1}$ and $R_{G2}$, or $R_{G5}$ and $R_{G6}$ combine to form an optionally substituted cycloalkyl or heterocyclyl, or any pharmaceutically acceptable salt or solvate thereof, or any stereoisomer thereof.

In some embodiments of Formula (VIII-A), when $R_{G1}$ is unsubstituted phenyl and $R_{G2}$ is H, $R_{G5}$ and $R_{G6}$ do not combine to form unsubstituted cyclopentyl, Methods by which compounds of Formula (VIII) (e.g., compounds of Formula (VIII-A) can be prepared are known in the art. For example, Compound (62) shown in Scheme 12, can be prepared according to methods described in *Synthesis*, pages 771-783 (2002).

Scheme 12

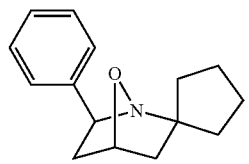
(62)

Compounds of Formula (VIII) (e.g., (VIII-A) and compound (62)), or any pharmaceutically acceptable salt or solvate thereof, or any stereoisomer thereof, can also be used as described herein (e.g., in pharmaceutical compositions, as inhibitors of necroptosis, in methods of treatment, and in kits).

In some embodiments, Formulas (VIII) and (VIII-A) do not include compound (62).

Additional Inhibitors of Necroptosis

Other compounds useful in the compositions, kits, and methods of the invention are described in U.S. Pat. Nos. 6,756,394 and 7,253,201, in U.S. Patent Publication No. 20050119260, and in pending U.S. application Ser. Nos. 12/077,320 and 12/086,792, each of which is hereby incorporated by reference. In addition to the compounds described by Formulas (I)-(VIII), other inhibitors of necroptosis include, but are not limited to, the structures depicted in Table 8, or any pharmaceutically acceptable salt or solvate thereof, or any stereoisomer thereof.

TABLE 8

| Compound | Structure |
|---|---|
| (63) | 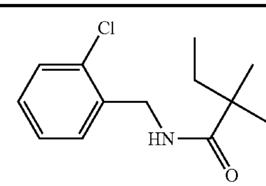 |
| (64) | 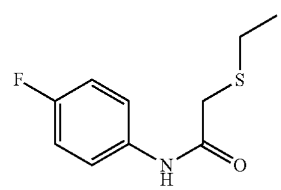 |
| (65) | 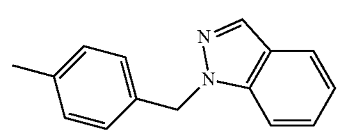 [SMILES: Cc1ccc(Cn2ncc3ccccc32)cc1] |
| (66) | 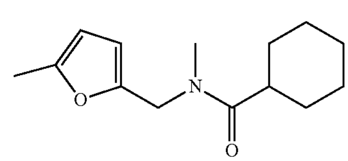 [SMILES: Cc1ccc(CN(C)C(=O)C2CCCCC2)o1] |
| (67) | 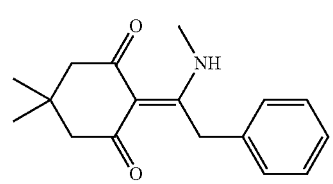 [SMILES: CNC(Cc1ccccc1)=C1C(=O)CC(C)(C)CC1=O] |

TABLE 8-continued

| Compound | Structure |
|---|---|
| (68) | *[chemical structure]* |
| (69) | *[chemical structure]* |
| (70) | *[chemical structure]* |

Pharmaceutical Compositions

The necrostatins described herein (e.g., compounds of Formulas (I)-(VIII) or any of compounds (1)-(7), (13)-(26), (27)-(33), (48)-(57), or (58)-(70)) can be formulated into pharmaceutical compositions for administration to human subjects in a biologically compatible form suitable for administration in vivo. Accordingly, the present invention provides a pharmaceutical composition comprising a compound of the invention in admixture with a pharmaceutically acceptable excipient. Conventional procedures and ingredients for the selection and preparation of suitable formulations are described, for example, in Remington's Pharmaceutical Sciences (2003-20$^{th}$ edition) and in The United States Pharmacopeia: The National Formulary (USP 24 NF19), published in 1999.

The compounds may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

Pharmaceutically Acceptable Excipients

Pharmaceutically acceptable excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

Oral Administration

Any of the compounds described herein (e.g., compounds of Formulas (I)-(VIII) or any of compounds (1)-(7), (13)-(26), (27)-(33), (48)-(57), or (58)-(70)) may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

Parenteral Administration

A compound may also be administered parenterally. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Nasal Administration

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Buccal or Sublingual Administration

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal alone or in combination with pharmaceutically acceptable carriers, as noted above, the proportion of which is determined by the solubility and chemical nature of the compound, chosen route of administration, and standard pharmaceutical practice.

Dosage Amounts

The amount of active ingredient (e.g., a compound of Formulas (I)-(VIII) or any of compounds (1)-(7), (13)-(26), (27)-(33), (48)-(57), or (58)-(70)) in the compositions of the invention can be varied. One skilled in the art will appreciate that the exact individual dosages may be adjusted somewhat depending upon a variety of factors, including the protein being administered, the time of administration, the route of administration, the nature of the formulation, the rate of excretion, the nature of the subject's conditions, and the age, weight, health, and gender of the patient. Generally, dosage levels of between 0.1 µg/kg to 100 mg/kg of body weight are administered daily as a single dose or divided into multiple doses. Desirably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

Therapeutic Uses and Screening Methods

The compounds disclosed herein (e.g., compounds of Formulas (I)-(VIII) or any of compounds (1)-(7), (13)-(26), (27)-(33), (48)-(57), or (58)-(70)) can be used to treat disorders where necroptosis is likely to play a substantial role (e.g., cerebral ischemia, traumatic brain injury, a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, or any condition in which alteration in cell proliferation, differentiation or intracellular signaling is a causative factor). Compounds of the invention can also be used in screening methods to identify targets of necroptosis and to identify additional inhibitors of necroptosis, as well as in assay development.

Compounds disclosed herein can be evaluated for their pharmacological properties in animal models of disease. The compounds identified to decrease necrosis or necroptosis may be structurally modified and subsequently used to decrease necrosis or necroptosis, or to treat a subject with a condition in which necrosis or necroptosis occurs. The methods used to generate structural derivatives of the small molecules that decrease necrosis or necroptosis are readily known to those skilled in the fields of organic and medicinal chemistry.

Therapy according to the invention may be performed alone or in conjunction with another therapy, for example in combination with apoptosis inhibitors, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, as well as how the patient responds to the treatment. Additionally, a person having a greater risk of developing a condition may receive prophylactic treatment to inhibit or delay symptoms of the disease.

In some embodiments, the compounds and methods of the invention can be used to treat any of the following disorders where necroptosis is likely to play a substantial role: a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, and any condition in which alteration in cell proliferation, differentiation or intracellular signaling is a causative factor.

Conditions Caused by Alteration in Cell Proliferation, Differentiation, or Intracellular Signalling Conditions in which alteration in cell proliferation, differentiation or intracellular signaling is a causative factor include cancer and infection, e.g., by viruses (e.g., acute, latent and persistent), bacteria, fungi, or other microbes.

Exemplary viruses are human immunodeficiency virus (HIV), Epstein-Barr virus (EBV), cytomegalovirus (CMV)5 human herpesviruses (HHV), herpes simplex viruses (HSV), human T-Cell leukemia viruses (HTLV)5 Varicella-Zoster virus (VZV), measles virus, papoviruses (JC and BK), hepatitis viruses, adenovirus, parvoviruses, and human papillomaviruses. Exemplary diseases caused by viral infection include, but are not limited to, chicken pox, Cytomegalovirus infections, genital herpes, Hepatitis B and C, influenza, and shingles.

Exemplary bacteria include, but are not limited to *Campylobacter jejuni, Enterobacter* species, *Enterococcus faecium, Enterococcus faecalis, Escherichia coli* (e.g., *E. coli* O157:H7), Group A streptococci, *Haemophilus influenzae, Helicobacter pylori, listeria, Mycobacterium tuberculosis, Pseudomonas aeruginosa, S. pneumoniae, Salmonella, Shigella, Staphylococcus aureus,* and *Staphylococcus epidermidis*. Exemplary diseases caused by bacterial infection include, but are not limited to, anthrax, cholera, diphtheria, foodborne illnesses, leprosy, meningitis, peptic ulcer disease, pneumonia, sepsis, tetanus, tuberculosis, typhoid fever, and urinary tract infection.

Neurodegenerative Diseases

Exemplary neurodegenerative diseases are Alzheimer's disease, Huntington's disease, Parkinson's disease, amyotrophic lateral sclerosis, HIV-associated dementia, cerebral ischemia, amyotropic lateral sclerosis, multiple sclerosis, Lewy body disease, Menke's disease, Wilson's disease, Creutzfeldt-Jakob disease, and Fahr disease. Exemplary muscular dystrophies or related diseases are Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease. Muscle wasting can be associated with cancer, AIDS, congestive heart failure, and chronic obstructive pulmonary disease, as well as include necrotizing myopathy of intensive care.

Compounds and methods of the invention can additionally be used to boost the immune system, whether or not the patient being treated has an immunocompromising condition. For example, the compounds described herein can be used in a method to strengthen the immune system during immunization, e.g., by functioning as an adjuvant, or by being combined with an adjuvant.

Kits

Any of the compounds or pharmaceutical compositions of the invention (e.g., those that include a compound of Formulas (I)-(VIII) or any of compounds (1)-(7), (13)-(26), (27)-(33), (48)-(57), or (58)-(70)) can be used together with a set of instructions, i.e., to form a kit. The kit may include instructions for use of the compounds of the invention in a screening method or as a therapy as described herein.

The following non-limiting examples are illustrative of the present invention.

EXAMPLES

Example 1

Determination of Necroptosis Inhibitory Activity

Evaluation of necroptosis inhibitory activity was performed using a FADD-deficient variant of human Jurkat T cells or with L929 cells treated with TNF-α as previously described (Degterev et al., Nat. Chem. Biol. 1:112 (2005) and Jagtap et al., J. Med. Chem. 50: 1886 (2007)). Utilizing these conditions the cells efficiently underwent necroptosis. For $EC_{50}$ value determinations, cells were treated with 10 ng/mL of human TNF-α in the presence of increasing concentration of test compounds for 24 hours followed by ATP-based viability assessment.

ATP-based viability assessment: Briefly, necroptosis activity was performed using a FADD-deficient variant of human Jurkat T cells or L929 cells treated with TNF-α. For $EC_{50}$ value determinations, cells (500,000 cells/mL, 100 μL per well in a 96-well plate) were treated with 10 ng/mL of human TNF-α in the presence of increasing concentration of test compounds for 24 hours at 37° C. in a humidified incubator with 5% $CO_2$ followed by ATP-based viability assessment. Stock solutions (30 mM) in DMSO were initially prepared and then diluted with DMSO to give testing solutions, which were added to each test well. The final DMSO concentration was 0.5%. Eleven compound test concentrations (0.030-100 μM) were used. Each concentration was done in duplicate.

Cell viability assessments were performed using a commercial luminescent ATP-based assay kit (CellTiter-Glo, Promega, Madison, Wis.) according to the manufacturer's instructions. Briefly, 40 μL of the cell lysis/ATP detection reagent was added to each well. Plates were incubated on a rocking platform for 10 minutes at room temperature and luminescence was measured using a Wallac Victor 3 plate-reader (Perkin Elmer, Wellesley, Mass.). Cell viability was expressed as a ratio of the signal in the well treated with TNF-α and compound to the signal in the well treated with compound alone. This was done to account for nonspecific toxicity, which in most cases was <10%. $EC_{50}$ values were calculated using nonlinear regression analysis of sigmoid dose-response (variable slope) curves from plots of log [I] verses viability values.

Results obtained using these procedures are shown in Table 9.

TABLE 9

| Compound no. | Structure | $EC_{50}$ Fadd −/− Jurkat | $EC_{50}$ L929 | $LD_{50}$ Fadd −/− Jurkat |
|---|---|---|---|---|
| (1) | 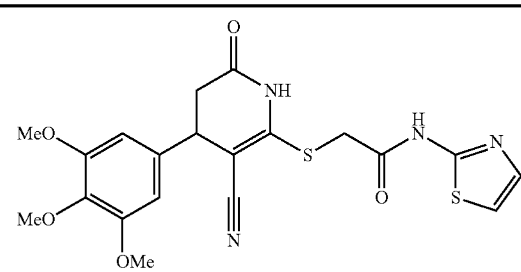 | 0.4769 | 0.1971 | >2000 |
| (2) | 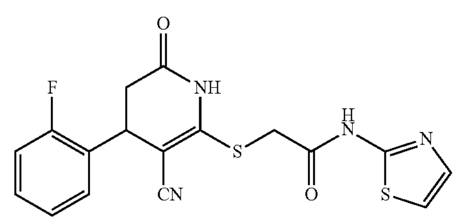 [SMILES: N#CC1=C(SCC(=O)Nc2nccs2)NC(=O)CC1c1ccccc1F] | 0.7690 | — | — |
| (3) | 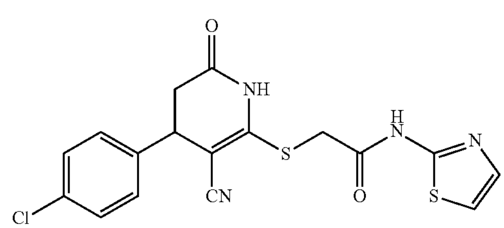 [SMILES: N#CC1=C(SCC(=O)Nc2nccs2)NC(=O)CC1c1ccc(Cl)cc1] | 0.8232 | — | — |

TABLE 9-continued

| Compound no. | Structure | EC$_{50}$ Fadd -/- Jurkat | EC$_{50}$ L929 | LD$_{50}$ Fadd -/- Jurkat |
|---|---|---|---|---|
| (4) | 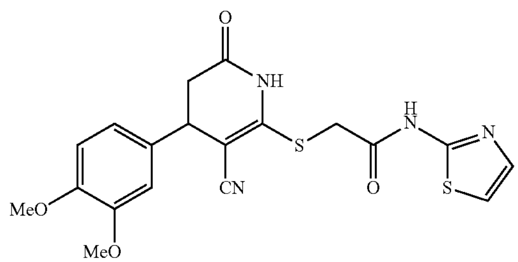 [SMILES: COc1ccc(C2CC(=O)NC(SCC(=O)Nc3nccs3)=C2C#N)cc1OC] | 0.3540 | — | — |
| (5) | 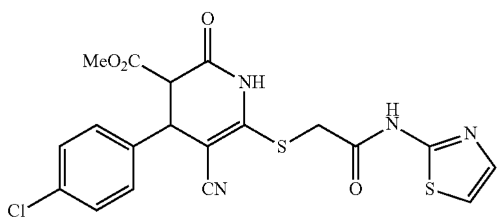 [SMILES: COC(=O)C1C(=O)NC(SCC(=O)Nc2nccs2)=C(C#N)C1c1ccc(Cl)cc1] | 24.98 | — | — |
| (6) | 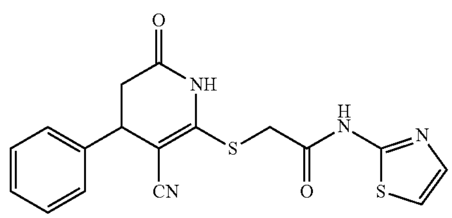 [SMILES: N#CC1=C(SCC(=O)Nc2nccs2)NC(=O)CC1c1ccccc1] | Partial activity | — | — |
| (7) | 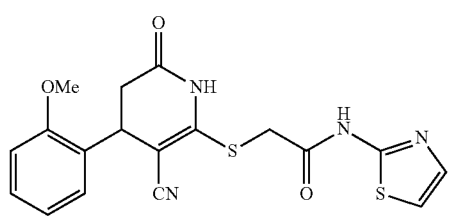 [SMILES: COc1ccccc1C1CC(=O)NC(SCC(=O)Nc2nccs2)=C1C#N] | 2.379 | — | — |
| (8) | 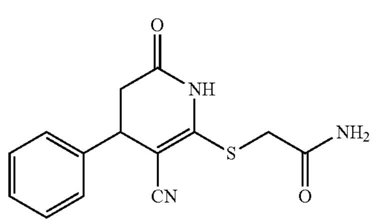 [SMILES: N#CC1=C(SCC(N)=O)NC(=O)CC1c1ccccc1] | inactive | | |
| (9) | 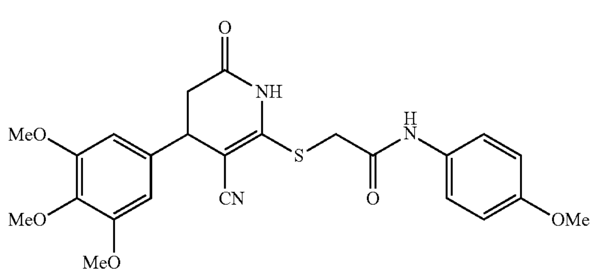 [SMILES: COc1ccc(NC(=O)CSC2=C(C#N)C(c3cc(OC)c(OC)c(OC)c3)CC(=O)N2)cc1] | inactive | | |

TABLE 9-continued

| Compound no. | Structure | EC$_{50}$ Fadd −/− Jurkat | EC$_{50}$ L929 | LD$_{50}$ Fadd −/− Jurkat |
|---|---|---|---|---|
| (10) | 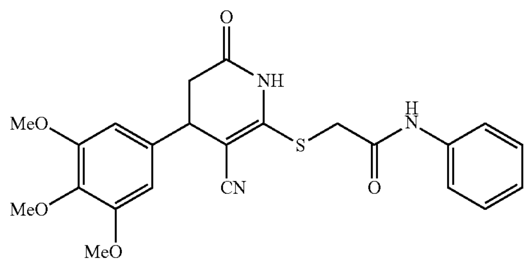 [SMILES: COc1cc(C2CC(=O)NC(SCC(=O)Nc3ccccc3)=C2C#N)cc(OC)c1OC] | inactive | | |
| (11) | 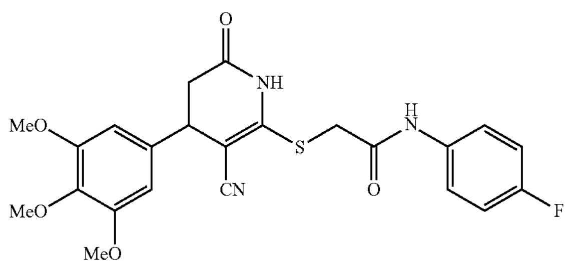 [SMILES: COc1cc(C2CC(=O)NC(SCC(=O)Nc3ccc(F)cc3)=C2C#N)cc(OC)c1OC] | inactive | | |
| (12) | 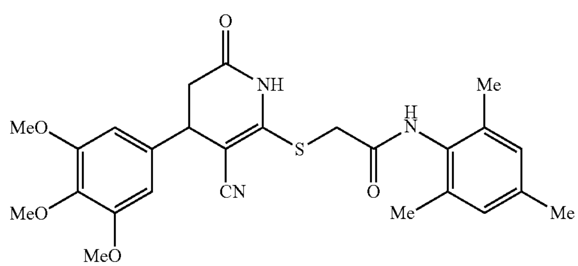 [SMILES: COc1cc(C2CC(=O)NC(SCC(=O)Nc3c(C)cc(C)cc3C)=C2C#N)cc(OC)c1OC] | inactive | | |
| (13) | 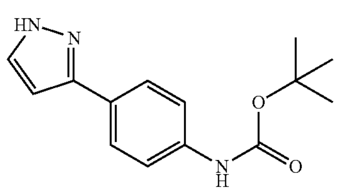 [SMILES: CC(C)(C)OC(=O)Nc1ccc(-c2cc[nH]n2)cc1] | 5.379 | 0.89 | 539.4 |
| (14) | 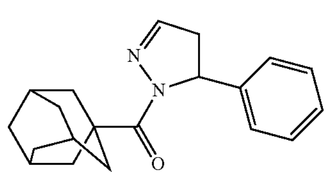 [SMILES: O=C(N1N=CCC1c1ccccc1)C12CC3CC(CC(C3)C1)C2] | 0.4101 | 4.202 | 396.9 |
| (15) | 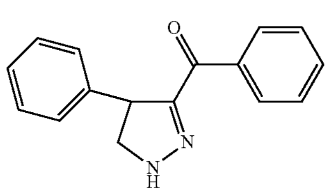 [SMILES: O=C(C1=NNCC1c1ccccc1)c1ccccc1] | 0.3688 | 4.02 | 799.5 |

TABLE 9-continued

| Compound no. | Structure | EC$_{50}$ Fadd -/- Jurkat | EC$_{50}$ L929 | LD$_{50}$ Fadd -/- Jurkat |
| --- | --- | --- | --- | --- |
| (16) | 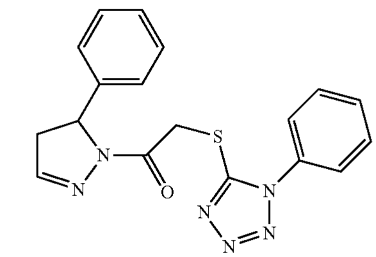 [SMILES: O=C(CSc1nnnn1-c1ccccc1)N1N=CCC1c1ccccc1] | 0.6289 | 72.97 | 247.7 |
| (17) | 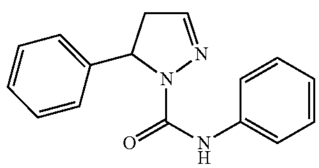 [SMILES: O=C(Nc1ccccc1)N1N=CCC1c1ccccc1] | inconclusive | — | — |
| (18) | 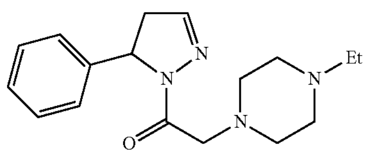 [SMILES: CCN1CCN(CC(=O)N2N=CCC2c2ccccc2)CC1] | 0.4101 | — | — |
| (19) | 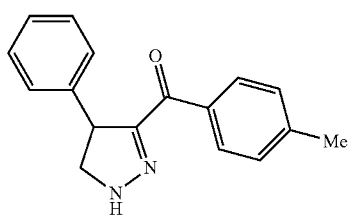 [SMILES: Cc1ccc(C(=O)C2=NNCC2c2ccccc2)cc1] | 0.3688 | — | — |
| (20) | 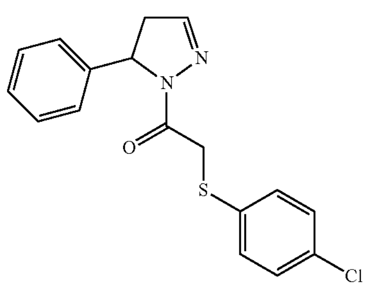 [SMILES: O=C(CSc1ccc(Cl)cc1)N1N=CCC1c1ccccc1] | 3.211 | — | — |
| (21) | 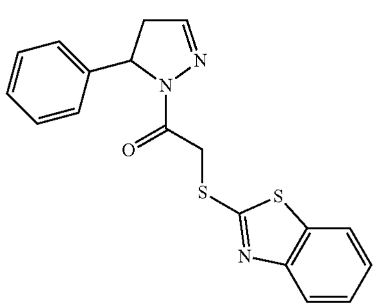 [SMILES: O=C(CSc1nc2ccccc2s1)N1N=CCC1c1ccccc1] | 1.557 | — | — |

TABLE 9-continued

| Compound no. | Structure | EC$_{50}$ Fadd -/- Jurkat | EC$_{50}$ L929 | LD$_{50}$ Fadd -/- Jurkat |
|---|---|---|---|---|
| (22) | 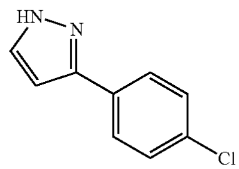 [SMILES: Clc1ccc(-c2cc[nH]n2)cc1] | Inactive | | |
| (23) | 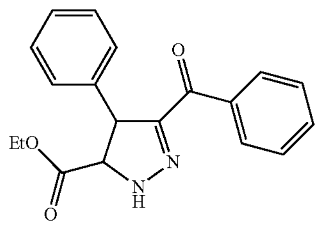 [SMILES: CCOC(=O)C1NN=C(C(=O)c2ccccc2)C1c1ccccc1] | Inactive | | |
| (24) | 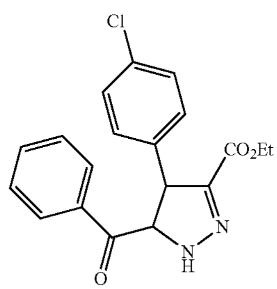 [SMILES: CCOC(=O)C1=NNC(C(=O)c2ccccc2)C1c1ccc(Cl)cc1] | Inactive | | |
| (25) | 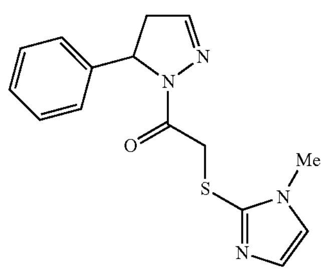 [SMILES: Cn1ccnc1SCC(=O)N1N=CCC1c1ccccc1] | Inactive | | |
| (26) | 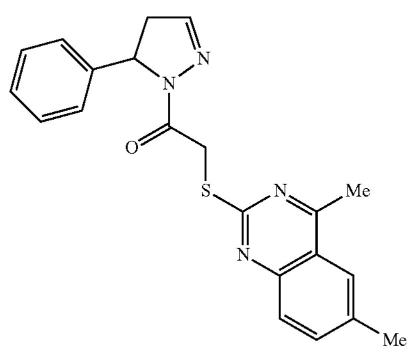 [SMILES: Cc1ccc2nc(SCC(=O)N3N=CCC3c3ccccc3)nc(C)c2c1] | Inactive | | |
| (27) | 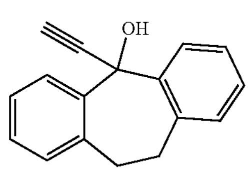 [SMILES: C#CC1(O)c2ccccc2CCc2ccccc21] | 3.227 | 0.659 | 541.3 |

TABLE 9-continued

| Compound no. | Structure | EC$_{50}$ Fadd −/− Jurkat | EC$_{50}$ L929 | LD$_{50}$ Fadd −/− Jurkat |
|---|---|---|---|---|
| (28) | 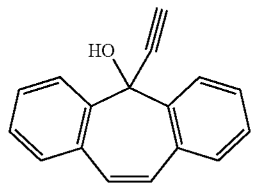 [SMILES: C#CC1(O)c2ccccc2C=Cc2ccccc21] | 2.98 | — | — |
| (29) | 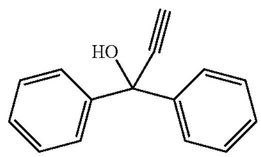 [SMILES: C#CC(O)(c1ccccc1)c1ccccc1] | 31.78 | — | — |
| (30) | 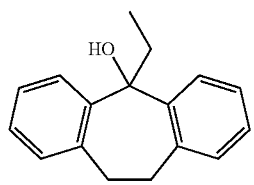 [SMILES: CCC1(O)c2ccccc2CCc2ccccc21] | 5.833 | — | — |
| (31) | 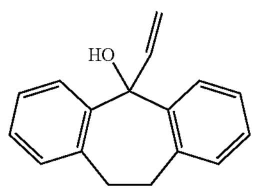 [SMILES: C=CC1(O)c2ccccc2CCc2ccccc21] | 2.954 | — | — |
| (32) | 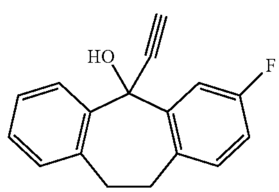 [SMILES: C#CC1(O)c2ccccc2CCc2ccc(F)cc21] | 2.002 | — | — |
| (33) | 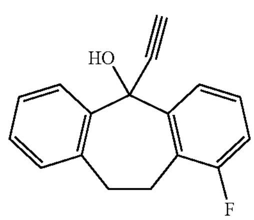 [SMILES: C#CC1(O)c2ccccc2CCc2c(F)cccc21] | 4.788 | — | — |
| (34) | 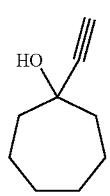 | Inactive | | |
| (35) | 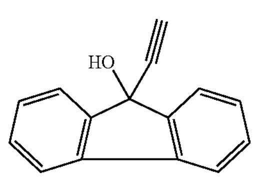 [SMILES: C#CC1(O)c2ccccc2-c2ccccc21] | Inactive | | |

TABLE 9-continued

| Compound no. | Structure | EC$_{50}$ Fadd -/- Jurkat | EC$_{50}$ L929 | LD$_{50}$ Fadd -/- Jurkat |
|---|---|---|---|---|
| (36) | 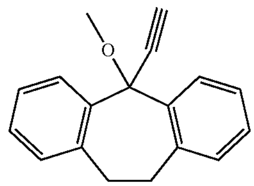 [SMILES: C#CC1(OC)c2ccccc2CCc2ccccc21] | Inactive | | |
| (37) | 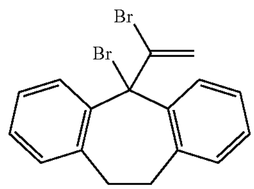 [SMILES: C=C(Br)C1(Br)c2ccccc2CCc2ccccc21] | Inactive | | |
| (38) | 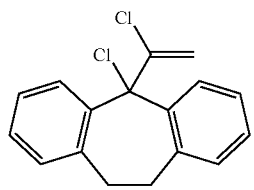 [SMILES: C=C(Cl)C1(Cl)c2ccccc2CCc2ccccc21] | Inactive | | |
| (39) | 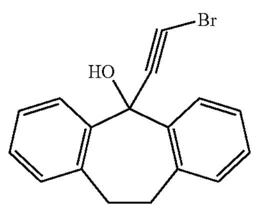 [SMILES: OC1(C#CBr)c2ccccc2CCc2ccccc21] | Inactive | | |
| (40) | 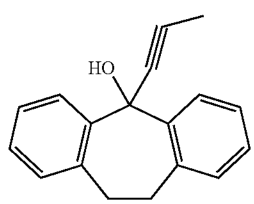 [SMILES: CC#CC1(O)c2ccccc2CCc2ccccc21] | Inactive | | |
| (41) | 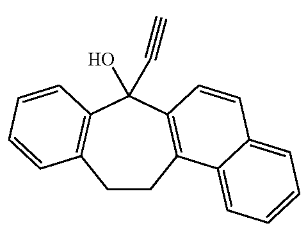 [SMILES: C#CC1(O)c2ccccc2CCc2c1ccc1ccccc21] | Inactive | | |
| (42) | 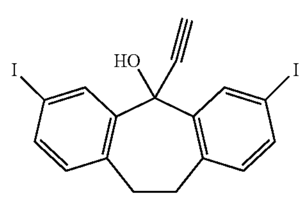 [SMILES: C#CC1(O)c2cc(I)ccc2CCc2ccc(I)cc21] | Inactive | | |

TABLE 9-continued

| Compound no. | Structure | EC$_{50}$ Fadd –/– Jurkat | EC$_{50}$ L929 | LD$_{50}$ Fadd –/– Jurkat |
|---|---|---|---|---|
| (43) | 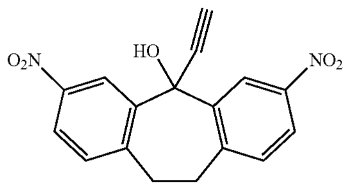 [SMILES: C#CC1(O)c2cc([N+](=O)[O-])ccc2CCc2ccc([N+](=O)[O-])cc21] | Inactive | | |
| (44) | 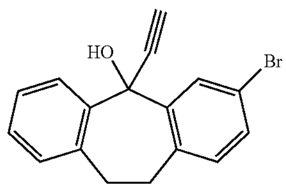 [SMILES: C#CC1(O)c2ccccc2CCc2ccc(Br)cc21] | Inactive | | |
| (45) | 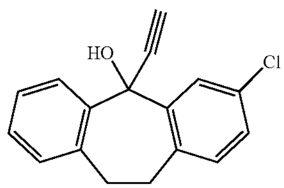 [SMILES: C#CC1(O)c2ccccc2CCc2ccc(Cl)cc21] | Inactive | | |
| (46) | 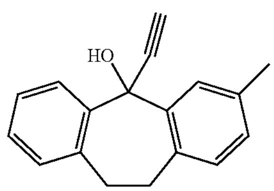 [SMILES: C#CC1(O)c2ccccc2CCc2ccc(C)cc21] | Inactive | | |
| (47) | 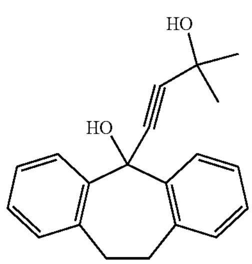 [SMILES: CC(C)(O)C#CC1(O)c2ccccc2CCc2ccccc21] | Inactive | | |
| (48) | 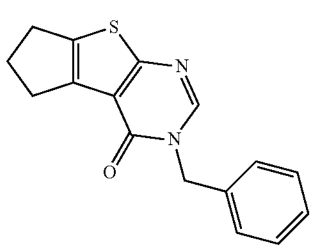 [SMILES: O=c1c2c3c(sc2ncn1Cc1ccccc1)CCC3] | 0.2161 | 8.66 | 188.9 |
| (49) | 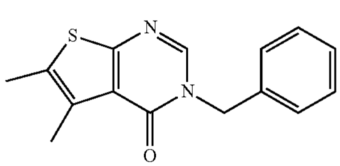 [SMILES: Cc1sc2ncn(Cc3ccccc3)c(=O)c2c1C] | 3.803 | — | — |

TABLE 9-continued
| Compound no. | Structure | EC$_{50}$ Fadd −/− Jurkat | EC$_{50}$ L929 | LD$_{50}$ Fadd −/− Jurkat |
|---|---|---|---|---|
| (50) | 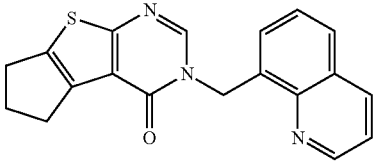 [SMILES: O=c1c2c3c(sc2ncn1Cc1cccc2cccnc12)CCC3] | >30 | — | — |
| (51) | 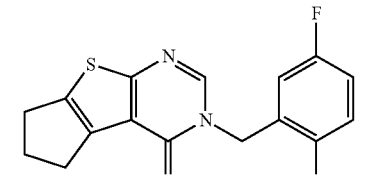 | 10.88 | — | — |
| (52) | 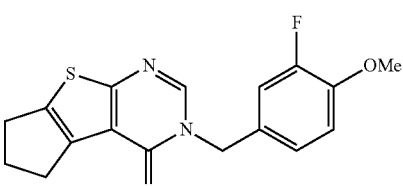 | 3.046 | — | — |
| (53) | 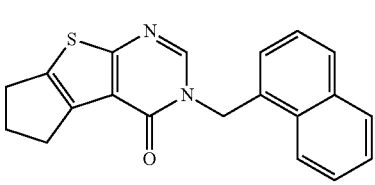 | >30 | — | — |
| (54) | 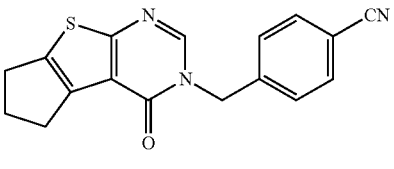 [SMILES: N#Cc1ccc(Cn2cnc3sc4c(c3c2=O)CCC4)cc1] | 0.8606 | — | — |
| (55) | 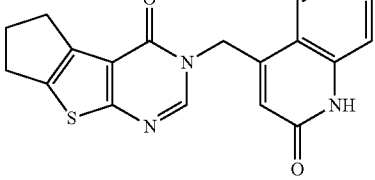 | >30 | — | — |
| (56) | 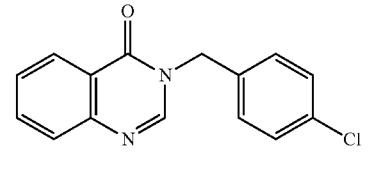 [SMILES: O=c1c2ccccc2ncn1Cc1ccc(Cl)cc1] | >30 | — | — |
| (57) | 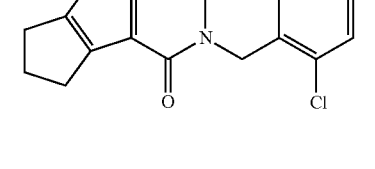 | 0.9363 | — | — |

TABLE 9-continued

| Compound no. | Structure | EC$_{50}$ Fadd -/- Jurkat | EC$_{50}$ L929 | LD$_{50}$ Fadd -/- Jurkat |
|---|---|---|---|---|
| (58) | 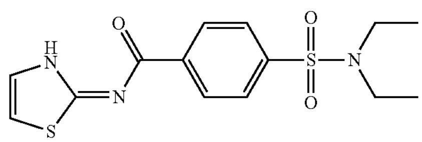 [SMILES: CCN(CC)S(=O)(=O)c1ccc(C(=O)/N=c2\[nH]ccs2)cc1] | 8.958 | 1.11 | >2000 |
| (59) | 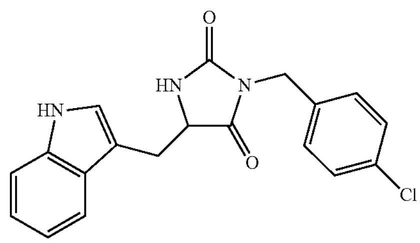 [SMILES: O=C1NC(Cc2c[nH]c3ccccc23)C(=O)N1Cc1ccc(Cl)cc1] | 0.3431 | 7.458 | 115.7 |
| (60) | 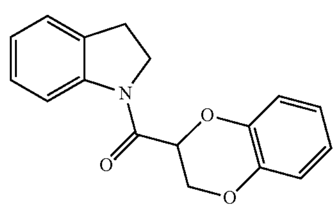 [SMILES: O=C(C1COc2ccccc2O1)N1CCc2ccccc21] | 0.6289 | 23.04 | 356.5 |
| (61) | 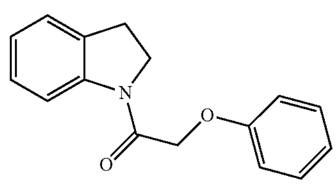 [SMILES: O=C(COc1ccccc1)N1CCc2ccccc21] | Inactive | | |
| (62) | 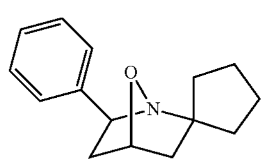 [SMILES: c1ccc(C2CC3CC4(CCCC4)N2O3)cc1] | 0.6683 | 10.09 | 754 |
| (63) | 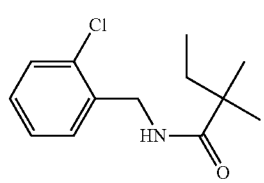 [SMILES: CCC(C)(C)C(=O)NCc1ccccc1Cl] | 2.364 | 13.7 | 1364 |
| (64) | 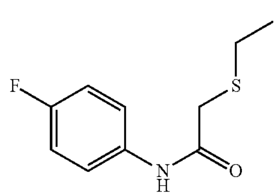 | 14.14 | Inactive | 1788 |

TABLE 9-continued

| Compound no. | Structure | EC$_{50}$ Fadd -/- Jurkat | EC$_{50}$ L929 | LD$_{50}$ Fadd -/- Jurkat |
|---|---|---|---|---|
| (65) | 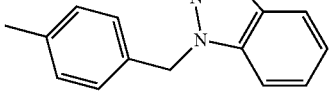 | 3.621 | Inactive | 138.6 |
| (66) | 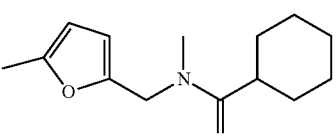 | 2.616 | 47.12 | 256.8 |
| (67) | 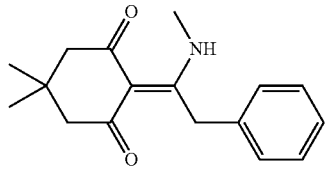 [SMILES: CNC(Cc1ccccc1)=C1C(=O)CC(C)(C)CC1=O] | 2.245 | 10.02 | 697.8 |
| (68) | 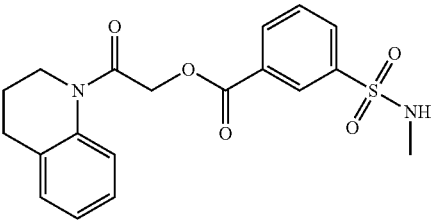 [SMILES: CNS(=O)(=O)c1cccc(C(=O)OCC(=O)N2CCCc3ccccc32)c1] | 1.633 | Inactive | 252.3 |
| (69) | 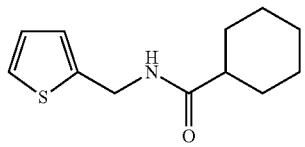 [SMILES: O=C(NCc1cccs1)C1CCCCC1] | 7.724 | Inactive | 1571 |
| (70) | 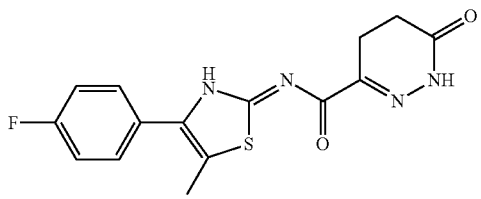 [SMILES: Cc1s/c(=N\C(=O)C2=NNC(=O)CC2)[nH]c1-c1ccc(F)cc1] | 0.9077 | Inactive | >2000 |

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound having the following structure:

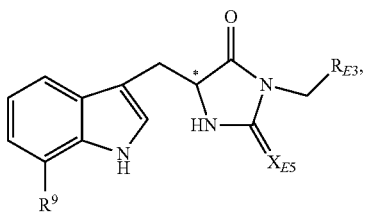

wherein:

$X_{E5}$ is O or S;

$R_{E3}$ is optionally substituted $C_{3-10}$ cycloalkyl, optionally substituted heterocyclyl, optionally substituted aryl, or optionally substituted heteroaryl;

$R^9$ is halogen, CN, $NO_2$, $OR^{13}$, $NR^{13}R^{14}$, $COR^{15}$, $CO_2R^{15}$, or optionally substituted $C_{1-6}$ alkyl;

each $R^{13}$ and $R^{14}$ is, independently, H, $COR^{16}$, $CO_2R^{16}$, optionally substituted $C_{1-6}$ alkyl, optionally substituted $C_{3-10}$ cycloalkyl, optionally substituted heterocyclyl, optionally substituted aryl, or optionally substituted heteroaryl; and each $R^{15}$ and $R^{16}$ is, independently, H, optionally substituted $C_{1-6}$ alkyl, optionally substituted $C_{3-10}$ cycloalkyl, optionally substituted heterocyclyl, optionally substituted aryl, or optionally substituted heteroaryl;

or any pharmaceutically acceptable salt or solvate thereof, or any stereoisomer thereof.

2. The compound of claim 1, wherein said compound has a structure according to the following formula:

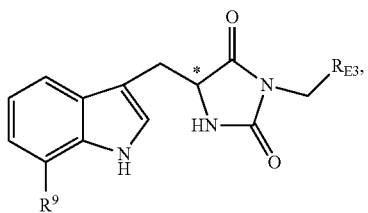

(VI-D-3)

wherein
  $R_{E3}$ is optionally substituted aryl or optionally substituted heteroaryl; and
  $R^9$ is halogen;
  or any pharmaceutically acceptable salt or solvate thereof, or any stereoisomer thereof.

3. The compound of claim 2, wherein $R_{E3}$ is unsubstituted $C_{3-10}$ cycloalkyl, unsubstituted heterocyclyl, unsubstituted aryl, or unsubstituted heteroaryl;
  or any pharmaceutically acceptable salt or solvate thereof, or any stereoisomer thereof.

4. The compound of claim 3, wherein $R_{E3}$ is unsubstituted aryl or heteroaryl,
  or any pharmaceutically acceptable salt or solvate thereof, or any stereoisomer thereof.

5. The compound of claim 2, wherein $R_{E3}$ is substituted $C_{3-10}$ cycloalkyl, substituted heterocyclyl, substituted aryl, or substituted heteroaryl;
  or any pharmaceutically acceptable salt or solvate thereof, or any stereoisomer thereof.

6. The compound of claim 5, wherein $R_{E3}$ is substituted aryl or substituted heteroaryl,
  or any pharmaceutically acceptable salt or solvate thereof, or any stereoisomer thereof.

7. The compound of claim 6, wherein $R_{E3}$ is substituted phenyl,
  or any pharmaceutically acceptable salt or solvate thereof, or any stereoisomer thereof.

8. The compound of claim 7, wherein said substituted phenyl is substituted with at least one halogen,
  or any pharmaceutically acceptable salt or solvate thereof, or any stereoisomer thereof.

9. The compound of claim 7, wherein said substituted phenyl is substituted with 1, 2, 3, 4, or 5 substituents selected, independently, from the group consisting of: $C_{1-6}$ alkyl, $C_{2-6}$ alkenyl, $C_{2-6}$ alkynyl, cycloalkyl, cycloalkenyl, heterocyclyl, aryl, heteroaryl, —$N_3$, —OR', —NR'C(=O)R'', —C(=O)NRR', —NRR', —OC(=O)NR'R'', —NRC(=O)OR', —OH, and —NC, wherein each R or R' is selected, independently, from H, $C_{1-6}$ alkyl, $C_{2-6}$ alkenyl, $C_{2-6}$ alkynyl, cycloalkyl, heterocyclyl, aryl, or heteroaryl,
  or any pharmaceutically acceptable salt or solvate thereof, or any stereoisomer thereof.

10. The compound of claim 2, wherein the stereocenter marked by the asterisk has the (R)-configuration,
  or any pharmaceutically acceptable salt or solvate thereof, or any stereoisomer thereof.

11. The compound of claim 2, wherein the stereocenter marked by the asterisk has the (S)-configuration,
  or any pharmaceutically acceptable salt or solvate thereof, or any stereoisomer thereof.

12. A pharmaceutical composition comprising the compound of claim 1 or any pharmaceutically acceptable salt or solvate thereof, or any stereoisomer thereof, and a pharmaceutically acceptable excipient.

13. The compound of claim 1, wherein said compound has a structure according to the following formula:

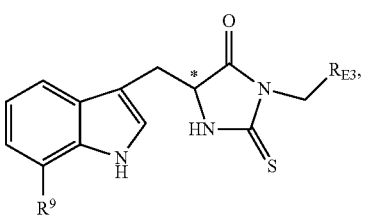

(VI-D-4)

wherein
  $R_{E3}$ is optionally substituted aryl or optionally substituted heteroaryl; and
  $R^9$ is halogen;
  or any pharmaceutically acceptable salt or solvate thereof, or any stereoisomer thereof.

14. The compound of claim 13, wherein $R_{E3}$ is unsubstituted $C_{3-10}$ cycloalkyl, unsubstituted heterocyclyl, unsubstituted aryl, or unsubstituted heteroaryl;
  or any pharmaceutically acceptable salt or solvate thereof, or any stereoisomer thereof.

15. The compound of claim 14, wherein $R_{E3}$ is unsubstituted aryl or heteroaryl,
  or any pharmaceutically acceptable salt or solvate thereof, or any stereoisomer thereof.

16. The compound of claim 13, wherein $R_{E3}$ is substituted $C_{3-10}$ cycloalkyl, substituted heterocyclyl, substituted aryl, or substituted heteroaryl;
  or any pharmaceutically acceptable salt or solvate thereof, or any stereoisomer thereof.

17. The compound of claim 16, wherein $R_{E3}$ is substituted aryl or substituted heteroaryl,
  or any pharmaceutically acceptable salt or solvate thereof, or any stereoisomer thereof.

18. The compound of claim 17, wherein $R_{E3}$ is substituted phenyl,
  or any pharmaceutically acceptable salt or solvate thereof, or any stereoisomer thereof.

19. The compound of claim 18, wherein said substituted phenyl is substituted with at least one halogen,
  or any pharmaceutically acceptable salt or solvate thereof, or any stereoisomer thereof.

20. The compound of claim 18, wherein said substituted phenyl is substituted with 1, 2, 3, 4, or 5 substituents selected, independently, from the group consisting of: $C_{1-6}$ alkyl, $C_{2-6}$ alkenyl, $C_{2-6}$ alkynyl, cycloalkyl, cycloalkenyl, heterocyclyl, aryl, heteroaryl, —N$_3$, —OR', —NR'C(=O)R", —C(=O)NRR', —NRR', —OC(=O)NR'R", —NRC(=O)OR', —OH, and —NC, wherein each R or R' is selected, independently, from H, C$_{1-6}$ alkyl, C$_{2-6}$ alkenyl, C$_{2-6}$ alkynyl, cycloalkyl, heterocyclyl, aryl, or heteroaryl, or any pharmaceutically acceptable salt or solvate thereof, or any stereoisomer thereof.

21. The compound of claim 13, wherein the stereocenter marked by the asterisk has the (R)-configuration, or any pharmaceutically acceptable salt or solvate thereof, or any stereoisomer thereof.

22. The compound of claim 13, wherein the stereocenter marked by the asterisk has the (S)-configuration, or any pharmaceutically acceptable salt or solvate thereof, or any stereoisomer thereof.

23. A pharmaceutical composition comprising the compound of claim 2 or any pharmaceutically acceptable salt or solvate thereof, or any stereoisomer thereof, and a pharmaceutically acceptable excipient.

24. A pharmaceutical composition comprising the compound of claim 13 or any pharmaceutically acceptable salt or solvate thereof, or any stereoisomer thereof, and a pharmaceutically acceptable excipient.

25. A method of treating a condition in a subject, said method comprising administering the compound of claim 1 or any pharmaceutically acceptable salt or solvate thereof, or any stereoisomer thereof, to said subject in a dosage sufficient to decrease necroptosis.

26. The method of claim 25, wherein said condition is a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, or any condition in which alteration in cell proliferation, differentiation or intracellular signaling is a causative factor.

27. A method of treating a condition in a subject, said method comprising administering the compound of claim 2 or any pharmaceutically acceptable salt or solvate thereof, or any stereoisomer thereof, to said subject in a dosage sufficient to decrease necroptosis.

28. The method of claim 27, wherein said condition is a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, or any condition in which alteration in cell proliferation, differentiation or intracellular signaling is a causative factor.

29. A method of treating a condition in a subject, said method comprising administering the compound of claim 13 or any pharmaceutically acceptable salt or solvate thereof, or any stereoisomer thereof, to said subject in a dosage sufficient to decrease necroptosis.

30. The method of claim 29, wherein said condition is a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, myocardial infarction, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, or any condition in which alteration in cell proliferation, differentiation or intracellular signaling is a causative factor.

* * * * *